United States Patent
Abbott et al.

(10) Patent No.: US 11,590,472 B2
(45) Date of Patent: Feb. 28, 2023

(54) METHODS AND COMPOSITIONS FOR ON-DEMAND RELEASE OF $ClO_2$ GAS FROM UV-ACTIVATED CHLORITE ION

(71) Applicants: Wisconsin Alumni Research Foundation, Madison, WI (US); Bemis Company, Inc., Neenah, WI (US)

(72) Inventors: Nicholas Abbott, Madison, WI (US); Rishabh Jain, Appleton, WI (US); Kevin Nelson, Neenah, WI (US); David Busche, Neenah, WI (US); David Lynn, Middleton, WI (US)

(73) Assignees: Wisconsin Alumni Research Foundation, Madison, WI (US); Bemis Company, Inc., Neenah, WI (US)

( * ) Notice: Subject to any disclaimer, the term of this patent is extended or adjusted under 35 U.S.C. 154(b) by 958 days.

(21) Appl. No.: 15/753,312

(22) PCT Filed: Aug. 18, 2016

(86) PCT No.: PCT/US2016/047603
§ 371 (c)(1),
(2) Date: Feb. 17, 2018

(87) PCT Pub. No.: WO2017/031345
PCT Pub. Date: Feb. 23, 2017

(65) Prior Publication Data
US 2018/0243456 A1    Aug. 30, 2018

Related U.S. Application Data

(60) Provisional application No. 62/206,464, filed on Aug. 18, 2015.

(51) Int. Cl.
*C01B 11/02* (2006.01)
*B01J 19/12* (2006.01)
(Continued)

(52) U.S. Cl.
CPC .............. *B01J 19/123* (2013.01); *A23B 7/144* (2013.01); *A61L 2/20* (2013.01); *B32B 1/02* (2013.01);
(Continued)

(58) Field of Classification Search
CPC ........ A61L 2/20; A61L 2202/11; B32B 27/08; B32B 15/082; B32B 15/085; B32B 15/20;
(Continued)

(56) References Cited

U.S. PATENT DOCUMENTS

| | | |
|---|---|---|
| 3,754,079 A | 8/1973 | Callerame |
| 4,456,511 A | 6/1984 | Fisher |

(Continued)

FOREIGN PATENT DOCUMENTS

| | | |
|---|---|---|
| CN | 1355768 A | 6/2002 |
| CN | 101195477 A | 6/2008 |

(Continued)

OTHER PUBLICATIONS

Dehydration, Hawley's Condensed Chemical Dictionary, R.J. Lewis ed., Mar. 15, 2007 (Year: 2007).*

(Continued)

*Primary Examiner* — Nicholas A Smith
(74) *Attorney, Agent, or Firm* — Mueting Raasch Group

(57) ABSTRACT

Compositions and methods for generating $ClO_2$ gas are disclosed. A composition that includes a chlorite salt is activated by exposure to ultraviolet light. After an optional storage period, the composition is then exposed to moisture, resulting in the generation of $ClO_2$ gas. Exemplary compositions include polymers in which the chlorite salt is dispersed. The polymers may be used to form films that can be used to package, e.g., food products, pharmaceutical products, medical devices, and/or laboratory devices. Upon exposure to ultraviolet light and moisture, the packaging (Continued)

releases controlled quantities of ClO$_2$ gas, which may disinfect and/or deodorize the packaged device or product.

17 Claims, 17 Drawing Sheets

(51) Int. Cl.

| | | |
|---|---|---|
| C08L 23/12 | (2006.01) | |
| C08K 3/24 | (2006.01) | |
| B32B 27/18 | (2006.01) | |
| B32B 27/30 | (2006.01) | |
| B32B 27/32 | (2006.01) | |
| B32B 7/12 | (2006.01) | |
| B32B 27/36 | (2006.01) | |
| B32B 27/28 | (2006.01) | |
| B32B 27/34 | (2006.01) | |
| B32B 15/08 | (2006.01) | |
| B65D 1/00 | (2006.01) | |
| A61L 2/20 | (2006.01) | |
| B32B 1/02 | (2006.01) | |
| B32B 15/082 | (2006.01) | |
| B32B 15/085 | (2006.01) | |
| B32B 15/20 | (2006.01) | |
| B32B 27/08 | (2006.01) | |
| B32B 27/20 | (2006.01) | |
| B65D 65/40 | (2006.01) | |
| B65D 81/24 | (2006.01) | |
| A23B 7/144 | (2006.01) | |

(52) U.S. Cl.
CPC ............... *B32B 7/12* (2013.01); *B32B 15/08* (2013.01); *B32B 15/082* (2013.01); *B32B 15/085* (2013.01); *B32B 15/20* (2013.01); *B32B 27/08* (2013.01); *B32B 27/18* (2013.01); *B32B 27/20* (2013.01); *B32B 27/28* (2013.01); *B32B 27/30* (2013.01); *B32B 27/304* (2013.01); *B32B 27/306* (2013.01); *B32B 27/32* (2013.01); *B32B 27/322* (2013.01); *B32B 27/34* (2013.01); *B32B 27/36* (2013.01); *B65D 1/00* (2013.01); *B65D 65/40* (2013.01); *B65D 81/24* (2013.01); *C01B 11/024* (2013.01); *C08K 3/24* (2013.01); *C08L 23/12* (2013.01); *A61L 2202/11* (2013.01); *B01J 2219/0879* (2013.01); *B01J 2219/1203* (2013.01); *B32B 2255/10* (2013.01); *B32B 2255/20* (2013.01); *B32B 2255/205* (2013.01); *B32B 2264/10* (2013.01); *B32B 2307/40* (2013.01); *B32B 2307/50* (2013.01); *B32B 2307/71* (2013.01); *B32B 2307/7242* (2013.01); *B32B 2307/7244* (2013.01); *B32B 2307/7246* (2013.01); *B32B 2307/732* (2013.01); *B32B 2307/748* (2013.01); *B32B 2315/00* (2013.01); *B32B 2323/10* (2013.01); *B32B 2405/00* (2013.01); *B32B 2439/06* (2013.01); *B32B 2439/46* (2013.01); *B32B 2439/70* (2013.01); *B32B 2439/80* (2013.01); *C08L 2203/16* (2013.01)

(58) Field of Classification Search
CPC ....... B32B 27/20; B32B 27/306; B32B 27/32; B32B 27/18; B32B 7/02; B32B 7/12; B32B 27/28; B32B 27/30; B32B 27/304; B32B 27/322; B32B 27/34; B32B 27/36; B32B 2315/00; B32B 2323/10; B32B 2405/00; B32B 2255/10; B32B 2255/20; B32B 2307/7246; B32B 2307/732; B32B 2307/748; B32B 2439/06; B32B 2439/46; B32B 2439/70; B32B 2439/80; B32B 15/08; B32B 1/02; B32B 2307/7242; B32B 2307/71; B32B 2264/10; B32B 2307/40; B32B 2307/50; B32B 2255/205; B32B 2307/7244; B01J 19/123; B01J 2219/0879; B01J 2219/1203; C01B 11/024; C08K 3/24; A23B 7/144; C08L 23/12; C08L 2203/16; B65D 65/40; B65D 81/24
USPC ........................................ 204/157.48, 157.5
See application file for complete search history.

(56) References Cited

U.S. PATENT DOCUMENTS

| | | | |
|---|---|---|---|
| 4,585,482 A | 4/1986 | Tice et al. | |
| 4,874,489 A * | 10/1989 | Callerame | B01J 19/123 204/157.44 |
| 5,360,528 A | 11/1994 | Oh et al. | |
| 5,360,609 A | 11/1994 | Wellinghoff | |
| 5,631,300 A | 5/1997 | Wellinghoff | |
| 5,695,814 A | 12/1997 | Wellinghoff et al. | |
| 5,719,100 A * | 2/1998 | Zahradnik | A01N 59/00 210/501 |
| 5,888,528 A | 3/1999 | Wellinghoff et al. | |
| 5,922,776 A | 7/1999 | Wellinghoff et al. | |
| 5,965,264 A | 10/1999 | Barenberg et al. | |
| 5,980,826 A | 11/1999 | Barenberg et al. | |
| 6,231,830 B1 * | 5/2001 | Madray | A61K 8/22 252/187.21 |
| 6,554,887 B1 | 4/2003 | Inglis | |
| 6,605,304 B1 | 8/2003 | Wellinghoff et al. | |
| 6,767,509 B1 | 7/2004 | Griesbach et al. | |
| 7,273,567 B1 | 9/2007 | Wellinghoff et al. | |
| 7,449,194 B2 | 11/2008 | Lelah et al. | |
| 7,695,692 B2 | 4/2010 | Sanderson | |
| 8,652,411 B2 | 2/2014 | Taguchi et al. | |
| 2005/0079124 A1 * | 4/2005 | Sanderson | B01J 19/123 422/186 |
| 2005/0106380 A1 | 5/2005 | Gray et al. | |
| 2006/0006361 A1 * | 1/2006 | Callerame | C01B 11/022 252/182.11 |
| 2006/0068029 A1 * | 3/2006 | Mason | A01N 59/00 424/661 |
| 2006/0178445 A1 * | 8/2006 | Mcintyre | A01N 59/00 523/122 |
| 2008/0026029 A1 | 1/2008 | Wellinghoff et al. | |
| 2008/0299066 A1 * | 12/2008 | Wellinghoff | A01N 3/02 204/157.15 |
| 2009/0008238 A1 * | 1/2009 | Williams | A61L 2/20 204/157.48 |
| 2012/0164025 A1 | 6/2012 | Stockley, III et al. | |
| 2014/0311094 A1 | 10/2014 | Thompson et al. | |
| 2014/0348702 A1 * | 11/2014 | Wofford | A61L 2/088 422/186.3 |
| 2015/0024211 A1 * | 1/2015 | Miratsu | C08K 3/24 428/412 |
| 2017/0157904 A1 | 6/2017 | Abbott et al. | |
| 2018/0235246 A1 | 8/2018 | Abbott et al. | |
| 2018/0243456 A1 | 8/2018 | Abbott et al. | |

FOREIGN PATENT DOCUMENTS

| | | |
|---|---|---|
| CN | 102834350 A | 12/2019 |
| EP | 0 611 162 A1 | 11/1994 |
| EP | 1 198 412 B1 | 12/2008 |
| WO | WO 00/69775 A1 | 11/2000 |
| WO | WO 2010/045280 A2 | 4/2010 |
| WO | WO 2016/069864 A2 | 5/2016 |
| WO | WO 2017/031349 A1 | 2/2017 |

(56) References Cited

FOREIGN PATENT DOCUMENTS

| WO | WO 2017/031351 A1 | 2/2017 |
|----|-------------------|--------|
| ZA | 2001/9124 B | 11/2001 |

OTHER PUBLICATIONS

U.S. Appl. No. 62/206,464, filed Aug. 18, 2015, Wisconsin Alumni Research Foundation.
U.S. Appl. No. 15/433,510, filed Feb. 15, 2017, Abbott et al..
U.S. Appl. No. 15/753,314, filed Aug. 18, 2016, Abbott et al..
PCT/US2016/047608, Aug. 18, 2016, Abbott et al.
PCT/US2016/047612, Aug. 18, 2016, Abbott et al.
International Patent Application No. PCT/US2016/047603, filed Aug. 18, 2016; International Search Report / Written Opinion dated Nov. 3, 2016, 11 pages.
International Patent Application No. PCT/US201 6/047603, filed Aug. 18, 2016; International Preliminary Report on Patentability dated Mar. 1, 2018; 7 pages.
International Patent Application No. PCT/US2016/047608, filed Aug. 18, 2016; International Search Report / Written Opinion dated Nov. 15, 2016; 12 pages.
International Patent Application No. PCT/US2016/047608, filed Aug. 18, 2016; International Preliminary Report on Patentability dated Mar. 1, 2018; 8 pages.
International Patent Application No. PCT/US2016/047612, filed Aug. 18, 2016; International Search Report / Written Opinion dated Nov. 11, 2016, 12 pages.
International Patent Application No. PCT/US2016/047612, filed Aug. 18, 2016; International Preliminary Report on Patentability dated Mar. 1, 2018, 8 pages.
Aieta et al. "Determination of chlorine dioxide, chlorine, chlorite, and chlorate in water" 1984 *American Water Works Association* pp. 64-70.
Appendini et al. "Review of antimicrobial food packaging" 2002 *Innovative Food Science & Emerging Technologies* vol. (3):pp. 113-126.
Burton et al. "Effect of gaseous chlorine dioxide on indoor microbial contaminants" 2008 *Journal of the Air & Waste Management Association* vol. (58):pp. 647-656.
Buxton et al. Radiation chemistry and photochemistry of oxychlorine ions. Part 1, 2, and 3—1972 *Journal of the Chemical Society, Faraday Transactions 1: Physical Chemistry in Condensed Phases* vol. (68):pp. 947-977.
Cosson et al., "Photodecomposition of Chlorine Dioxide and Sodium Chlorite in Aqueous Solution by Irradiation with Ultraviolet Light" 1994 *Industrial and Engineering Chemistry Research*, vol. (33):pp. 1468-1475.
Diffey "Sources and measurement of ultraviolet radiation" 2002 *Methods* vol. (28):pp. 4-13.
Gagnon et al. "Disinfectant efficacy of chlorite and chlorine dioxide in drinking waterbiofilms" 2005 *Water Research* 1809-1817.
Gibbs et al. "Gaseous chlorine dioxide as an alternative for bedbug control" 2012 *Infection Control and Hospital Epidemiology* vol. (33):pp. 495-499.
Gómez-López et al. "Chlorine dioxide for minimally processed produce preservation: a review" 2009 *Trends in Food Science &Technology* vol. (20):pp. 17-26.
Gordon et al. "The chemistry of chlorine dioxide" 1972 *Progress in Inorganic Chemistry* vol. (15) pp. 201-286.
Han "Antimicrobial food packaging" 2003 *Novel food packaging techniques* pp. 50-70.
Hirneisen et al. "Viral Inactivation in Foods: A Review of Traditional and Novel Food-Processing Technologies" 2010 *Comprehensive Reviews in Food Science and Food Safety* vol. (9):pp. 3-20.
Jang et al. "Measurement of chlorine dioxide penetration in dairy process pipe biofilms during disinfection" 2006 Applied *Microbiology and Biotechnology* vol. (72).pp. 368-376.
Kaczur et al. "Chlorine oxygen acids and salts, chlorous acid, chlorites, and chlorine dioxide" 2000 *Kirk-Othmer Encyclopedia of Chemical Technology*.
Karpel et al. "Photodecomposition of chlorine dioxide and chlorite by u. v.—irradiation—Part II. Kinetic study" 1992 *Water Research* vol. (26):pp. 1665-1672.
Lee et al. "Efficacy of chlorine dioxide gas as a sanitizer of lettuce leaves" 2004 *Journal of Food Protection®* vol. (67):pp. 1371-1376.
Ruiz, R.P. "Karl Fischer Titration" 2001 *Current Protocols in Food Analytical Chemistry*, pp. A1.2.1-A1.2.4.
Scholz, E. Chapter 3 "Titration Techniques," *Karl Fischer titration: determination of water* 1984 Springer-Verlag, pp. 15-25.
Sy et al. "Evaluation of gaseous chlorine dioxide as a sanitizer for killing *Salmonella, Escherichia coli* O157: H7, Listeria monocytogenes, and yeasts and molds on fresh and fresh-cut produce" 2005 *Journal of Food Protection®* vol. (68):pp. 1176-1187.
Vogt et al. "Chlorine Oxides and Chlorine Oxygen Acids" 2005 *Ullmann's Encyclopedia of Industrial Chemistry*. Wiley-VCH Verlag GmbH & Co.KGaA.
Volk et al. "Implementation of chlorine dioxide disinfection: Effects of the treatment change on drinking water quality in a full-scale distribution system" 2002 *Journal of Environmental Engineering and Science* vol. (1):pp. 323-330.
Weaver-Meyers et al. "Controlling mold on library materials with chlorine dioxide: an eight-year case study" 1998 *The Journal of academic librarlanship* vol. (24):pp. 455-458.
Whitney et al. "Inactivation of Bacillus anthracis spores" *2003 Emerging infectious diseases* vol. (9):p. 623-627.
Wilson et al. "Effect of chlorine dioxide gas on fungi and mycotoxins associated with sick building syndrome" 2005 *Applied and Environmental Microbiology* vol. (71):pp. 5399-5403.

\* cited by examiner

METHODS AND COMPOSITIONS FOR ON-DEMAND RELEASE OF CLO₂ GAS FROM UV-ACTIVATED CHLORITE ION

CROSS-REFERENCE TO RELATED APPLICATIONS

This application is the § 371 U.S. National Stage of International Application No. PCT/US2016/047603, filed Aug. 18, 2016, which claims the benefit of U.S. Provisional Patent Application No. 62/206,464, filed Aug. 18, 2015, which application is hereby incorporated herein by reference to the extent that it does not conflict with the present disclosure.

FIELD

This disclosure relates generally to the controlled release of a disinfectant gas. In particular, the disclosure is directed to compositions and methods for the on-demand release of $ClO_2$ gas from UV-activated chlorite salts in the presence of moisture.

BACKGROUND

Chlorine dioxide ($ClO_2$) is a powerful oxidizing agent and disinfectant. It is used today primarily in bleaching processes in the paper pulp industry and as a disinfectant for water treatment. It has also been shown to be useful as a broad spectrum biocide in various applications such as food processing, fungus and mold fumigation, biofilm treatment and even in the killing of bedbugs and hardy anthrax spores.

Accordingly, it may be desirable to produce compositions that can release chlorine dioxide to inhibit microbial growth. However, control of production of gaseous $ClO_2$ can be difficult.

Wellinghoff et al. have devised polymer packaging films which release $ClO_2$ when the films come in contact with moisture. See, for example, U.S. Pat. Nos. 5,360,609 and 5,360,528. In systems described in, for example, U.S. Pat. No. 5,360,609, a mixture of an acid-releasing compound, such as an acid anhydride, and chlorite in different phases (hydrophobic and hydrophilic) can produce $ClO_2$ when the acid releasing compound is hydrolyzed to produce an acid, which reacts with chlorite. Notably, this system produces $ClO_2$ upon contact with moisture from any source, and thus the timing of $ClO_2$ production can be difficult to control.

Wellinghoff et al. have also devised a polymeric composition containing chlorite anion and an energy-activated catalyst, such as a photo-activated catalyst, that triggers the production of $ClO_2$ upon exposure to light, such as visible light. See, for example, U.S. Patent Publication No. 2008/0299066. The timing of $ClO_2$ production in this system is difficult to control because $ClO_2$ is produced whenever the polymer is exposed to light, including inadvertent exposure to ambient visible light.

It would be desirable to provide improved methods and compositions for more controlled release of $ClO_2$ gas that can be practically applied to large scale commercial applications, such as in packaging for food and medical products, and other applications.

SUMMARY

The inventors have developed methods by which compositions containing chlorite ions, such as chlorite salts, generate $ClO_2$ gas, a highly effective disinfectant. The compositions are exposed to ultraviolet (UV) light and are exposed to moisture resulting in the generation of chlorine dioxide gas. The compositions may be substantially free of an energy-activated catalyst and substantially free of an acid-releasing compound, yet still generate chlorine dioxide gas when exposed to moisture and to UV light.

The compositions can be exposed to the UV light prior to or concurrent with exposure to moisture. The compositions may generate chlorine dioxide gas if a delay of seconds, minutes, hours or even days occurs between exposing the composition to UV light and exposing the composition to moisture. In embodiments where the composition is previously exposed to UV light, chlorine gas is generated upon exposing the compositions to moisture.

When the compositions are substantially free of an energy-activated catalyst and are substantially free of an acid-releasing compound, the compositions can generate chlorine dioxide upon being subjected to a two-stage gas generating protocol comprising a step of exposing the compositions to UV light and another step of exposing the compositions to water. However, the compositions do not generate a significant amount of chlorine dioxide when exposed to UV light alone (in the absence of moisture) and do not generate a significant amount of chlorine dioxide when exposed to moisture alone (in the absence of prior or concurrent UV light).

By requiring two steps, UV light and moisture, rather than a single step, light alone or moisture alone, the compositions described herein provide for more controlled release of chlorine dioxide than previously described chlorine dioxide-releasing compositions, such as those described by Wellinghoff et al. In addition, by requiring the use of UV light, rather than visible light activated photocatalysts, such as those described by Wellinghoff et al., the compositions described herein do not release significant amounts of chlorine dioxide when exposed to ambient visible light. Accordingly, the compositions described herein can be manufactured and stored under typical lighting conditions, as opposed to in the dark, as well as manufactured and stored in humid conditions, without premature generation of chlorine dioxide. As such, the ability of the compositions described herein to release significant or effective amounts of chlorine dioxide at a desired time can be enhanced relative to previously described chlorine-generating compositions that include one or both of an acid-releasing compound and an energy-activated catalyst.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals.

FIG. 5A, wavelength is 312 nm. FIG. 5B, wavelength is 365 nm.

Figure 1:
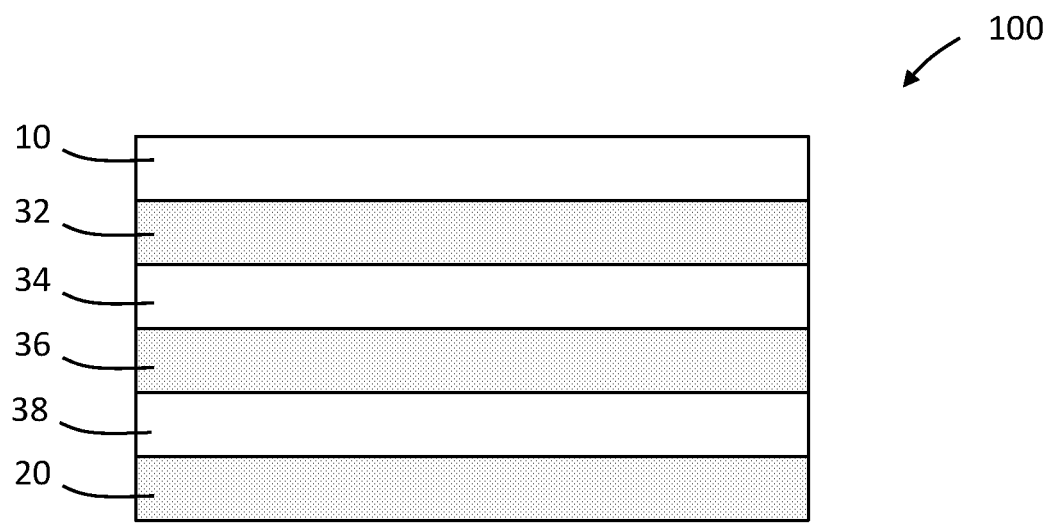
FIG. 1 is a schematic sectional view of an embodiment of a multilayer packaging films.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

The inventors have developed methods and compositions for on-demand generation of $ClO_2$ gas. The compositions comprise chlorite ions, for example in the form of chlorite salts, and generate $ClO_2$ gas following exposure to UV radiation and exposure to water, but do not generate a significant amount of $ClO_2$ gas after exposure to UV light without exposure to water when dry and do not generate a significant amount of $ClO_2$ gas after exposure to water without exposure to UV light. In some embodiments, the compositions generate an amount of $ClO_2$ gas for a sufficient amount of time to one or both of deodorize and disinfect a product in proximity to the composition.

The compositions described herein may be first exposed to ultraviolet light. After an optional storage period, the compositions may then be exposed to moisture resulting in the generation of $ClO_2$ gas. Alternatively, the compositions may generate $ClO_2$ gas by being first exposed to moisture, and subsequently by exposure to UV light such that the moisture is immediately present upon exposure of the composition to the UV light, or by simultaneously being exposed to moisture and UV light. The amount of $ClO_2$ generated can be regulated by, for example, varying the wavelength and exposure time and intensity of the ultraviolet light, the amount of water vapor (moisture) present, the concentration of chlorite salts in the composition, or the length of the storage period.

A two-stage gas generation protocol is used to generate $ClO_2$ gas. The first stage exposes the composition to ultraviolet light and the second stage exposes the composition to moisture. As used herein, the term "two-stage gas generation protocol" means two distinct unit operations done to a common target (i.e., a chlorite ion). The unit operations may be performed simultaneously or sequentially. The unit operations are distinct from one another in type. One or both of the unit operations may occur a single time or may be repeated in whole or in part. The unit operations can be completed sequentially with no time separation or can be separated by an intervening period of time.

A unit operation that repeats or is interrupted is considered a single unit operation. For example, multiple bursts of UV radiation is considered to be a single unit operation for purposes of the present disclosure.

A first unit operation can be exposure of a target to ultraviolet light followed by a second unit operation of exposure of the target to moisture. Alternatively, a first unit operation can be exposure of a target to moisture followed by a second unit operation of exposure of the target to ultraviolet light.

In contrast to a two-stage gas generation protocol described herein, a "single-stage gas generation protocol" uses a single unit operation to generate $ClO_2$ gas. For example, the single unit operation can be exposure to electromagnetic radiation or exposure to moisture. The single unit operation can be interrupted and restarted. Additionally, there may be a combination of single unit operations directed to alternate targets that occur simultaneously or in sequence. Such a combination of single unit operations is considered, for purposes of the present disclosure, to be multiple single-stage protocols. For example, a combination of first targets that react to electromagnetic radiation and second targets that react to moisture may be combined in a composition and processed simultaneously or sequentially through two distinct unit operations of electromagnetic radiation and exposure to moisture. This combination incorporates two single-stage gas generation protocols, not a two-stage gas generation protocol.

Single-stage gas generation protocols have been previously described to include compounds to facilitate the production of chlorine dioxide, such as an energy-activated catalyst or an acid-releasing compound. The compositions described herein are preferably substantially free of an energy-activated catalyst and an acid-releasing compound.

As used herein, an "energy-activated catalyst" is a compound that can catalyze the oxidation of $ClO_2^-$— to $ClO_2$ gas following activation of the catalyst compound by electromagnetic energy, such as visible light. Published U.S. Patent Application 2008/0299066A1 lists a number of compounds and classes of compounds as energy activated catalysts, some of which may be capable of catalyzing the oxidation of $ClO_2^-$— to $ClO_2$ gas following activation of the catalyst compound by electromagnetic energy. Published U.S. Patent Application 2008/0299066A1 lists metal oxides, metal sulfides, metal chalcogenites, metal phosphides, metal arsenides, non-metal semiconductors, photoactive homopolyanions, photoactive heteropolyanions, and polymeric semiconductors as examples of energy activated catalysts. The compositions described herein may be substantially free of those compounds that can catalyze the oxidation of $ClO_2^-$— to $ClO_2$ gas following activation of the catalyst compound by electromagnetic energy.

Published U.S. Patent Application 2008/0299066A1 discloses examples in which titanium dioxide is used as an energy activated catalyst to catalyze the oxidation of $ClO_2^-$— to $ClO_2$ gas. In some embodiments, the compositions described herein are substantially free of a metal oxide energy activated catalyst. In some embodiments, the compositions described herein are substantially free of titanium dioxide.

As used herein, an "acid-releasing compound" is a compound that, in the presence of moisture, can generate acid and hydronium ions, which hydronium ions can react with chlorite ions to form $ClO_2$ gas. U.S. Pat. No. 6,605,304 lists a number of acid releasing compounds for gas generation including carboxylic acids, esters, anhydrides, acyl halides, phosphoric acid, phosphate esters, trialkylsilyl phosphate esters, diallyl phosphates, sulfonic acid, sulfonic acid esters, sulfonic acid chlorides, phosphosilicates, phosphosilicic anhydrides, carboxylates of poly α-hydroxy alcohols such as sorbitan monostearate or sorbitol monostearate, phosphosiloxanes, and acid releasing waxes, such as propylene glycol monostearate acid releasing waxes. U.S. Pat. No. 6,605,304 also lists as acid-releasing compounds inorganic acid releasing agents, such as polyphosphates, including tetraalkyl ammonium polyphosphates, monobasic potassium phosphate, potassium polymetaphosphate, sodium metaphosphates, borophosphates, aluminophosphates, silicophosphates, sodium polyphosphates such as sodium tripolyphosphate, potassium tripolyphosphate, sodium-potassium phosphate, and salts containing hydrolyzable metal cations such as zinc. In some embodiments described herein, a composition for generating $ClO_2$ gas described herein is substantially-free of such compounds.

In some embodiments, the polymer in which the chlorite ion is dispersed is substantially free of an anhydride. In some such embodiments, the composition is substantially free of an alcohol, an amide, or an alcohol and an amide.

As used herein, a composition that is "substantially free of an acid-releasing compound" means that the composition includes a no acid-releasing compound or includes a quantity of acid-releasing compound that is not sufficient or not formulated to cause release of a significant amount of $ClO_2$ gas in the presence of moisture (in the absence of recently prior or concurrent UV irradiation) as compared to a two-stage gas generation protocol described herein. In some embodiments, the composition comprises 2% by weight or less of an acid-releasing compound. In some embodiments, the composition includes 1% by weight or less, or 0.5% by weight or less, of an acid-releasing compound. In some embodiments, the ratio (by weight) of acid-releasing compound to chlorite ion source, such as chlorite ion salt, in the composition is 1:10 or less. For example, the ratio of acid releasing compound to chlorite ion source may be 1:20 or less, such as 1:50 or less or 1:100 or less.

As used herein, a composition that is "substantially free of an energy-activated catalyst" means that the composition includes a no energy-activated catalyst or includes a quantity of energy-activated catalyst that is not sufficient or not formulated to cause release of a significant amount of $ClO_2$ gas upon exposure to UV light (in the absence of moisture) as compared to a two-stage gas generation protocol described herein. As used herein, the "absence of moisture" means having a moisture content of less than 500 ppm as measured by ASTM Method D6869-03(2011) Standard Test Method for Coulometric and Volumetric Determination of Moisture in Plastics Using the Karl Fischer Reaction (the Reaction of Iodine with Water). In many circumstances, placing the composition in a drying oven at 70° C. for 48 hours will result in a moisture content of less than 500 ppm. Whether the dried composition can produce a significant amount of chlorine dioxide upon exposure to UV radiation may then be tested as soon as practicable after removal from the oven to prevent the composition from sorbing moisture from the environment.

In some embodiments, the composition includes less than 10 weight percent of an energy-activated catalyst based on the total weight of the composition, such as less than 5 weight percent or less than 2 weight percent of an energy-activated catalyst based on the total weight of the composition. In some embodiments, the ratio (by weight) of energy-activated catalyst to chlorite ion source, such as chlorite ion salt, in the composition is 1:2 or less. For example, the ratio of energy-activated catalyst to chlorite ion source may be 1:5 or less, such as 1:10 or less or 1:20 or less. It should be understood that a small amount of a compound that may be considered an energy-activated catalyst can be present in the composition, for example to serve purposes other than generated $ClO_2$ gas, including for example, as a colorant, processing aid, catalyst residue, antiblocking agent and/or a slip agent.

In some embodiments, where a multilayer film or multilayer article includes a layer formed of the composition comprising chlorite ions, the weight percent and ratios of energy-activated catalyst and acid-releasing compound discussed above refers to the weight percent in the layer formed of the composition comprising chlorite ions rather than to the entire multilayer film or multilayer article. One or more layers of the film or article, other than the layer formed of the composition comprising chlorite ions, may include greater amounts of one or both of an energy-activated catalyst and an acid-releasing compound than the layer formed of the composition comprising chlorite ions. Of course one or more of layers of the film or article, other than the layer formed of the composition comprising chlorite ions, may also be substantially free of one or both of an energy-activated catalyst and an acid-releasing compound.

A composition that does not release a significant amount of $ClO_2$ gas when exposed to only one stage (and not two) of a two-stage gas generation protocol is, for purposes of the present disclosure, a composition that releases at least ten times less $ClO_2$ gas, when exposed to only the single stage (exposure to moisture but not UV light; or exposure to only UV light but not moisture), than an amount of $ClO_2$ released using a two-stage gas generation protocol. For example, the composition may release at least 20 times less, at least 50 times less, or at least 100 times less chlorine dioxide when exposed to a single stage gas generation protocol than when exposed to a two-stage gas generation protocol. In some cases, no $ClO_2$ gas is released in the presence of moisture or UV light alone.

In some embodiments, the composition generates less than 0.1 ppm $ClO_2$ gas in an interior volume in which the composition is disposed or for which an article comprising the compositions at least partially defines when the composition or article is exposed to only a single stage of a two-stage gas generation protocol. In some embodiments, the composition can generate 0.5 ppm $ClO_2$ gas in the interior volume when exposed to both stages (UV and moisture) of the two-stage gas generation protocol.

In some embodiments, a composition comprising chlorite ions capable of generating $ClO_2$ gas following a two-stage gas releasing protocol is substantially free of hydronium ions. As used herein, the term "substantially free of hydronium ions" means that the quantity of hydronium ions present in the composition is not sufficient to generate a significant amount of $ClO_2$ gas through exposure to moisture alone as taught by Wellinghoff et al., as compared to the $ClO_2$ gas generated through methods described herein.

The compositions described herein may include an amount of an acid-releasing compound or an energy-activated catalyst provided that the acid-releasing compound or energy-activated catalyst are not present in an amount or configuration that causes chlorine dioxide release in a significant amount during exposure a single-stage gas release protocol; namely, exposure to moisture or exposure to UV light, respectively.

In some embodiments described herein, a composition comprising chlorite ions releases $ClO_2$ gas after being exposed to a two-stage gas generation protocol comprising a first stage that includes exposing the composition to UV radiation and a second stage that includes exposing the composition to moisture. The composition does not generate a significant amount of $ClO_2$ gas if exposed to the first stage without being exposed to the second stage, and the composition does not generate a significant amount of $ClO_2$ gas if exposed to the second stage without being exposed to the first stage.

Subjecting a composition comprising chlorite ions to a two-stage gas generation protocol comprising a first stage including exposing the composition to UV light and a second stage that includes exposing the composition to moisture preferably results in release of an effective amount of $ClO_2$ gas release. As used herein, release of an "effective amount" of $ClO_2$ gas means that the amount of the $ClO_2$ gas released is effective to disinfect, deodorize, or disinfect and deodorize the composition comprising the chlorite ions or an article in close proximity, such as in contact with, the composition comprising the chlorite ions.

As used herein, "deodorize" means to remove or conceal an unpleasant smell. In many cases, the unpleasant smell may be caused by odor-causing bacteria, and killing of the bacteria may have a deodorizing effect. A composition described herein may release any suitable amount of $ClO_2$ gas to deodorize a food product, such as produce. For example, a film may release 2 parts per million (ppm) or greater $ClO_2$ into an interior volume defined by a package formed, at least in part, from the film. Typically, a composition may release 10 ppm or greater $ClO_2$ gas to deodorize produce. The concentration of chlorine dioxide may increase over time if the package is sealed, as additional chlorine dioxide is released from the film. The amount of $ClO_2$ gas needed to effectively deodorize produce will depend, in part, on the nature of the produce. In addition, the time that the produce is exposed to $ClO_2$ gas will affect the ability of the $ClO_2$ gas to deodorize the produce. In some embodiments, a composition releases an amount of $ClO_2$ gas for a time sufficient to expose the produce to 2 ppm·hours or greater of $ClO_2$ gas to deodorize the produce. For example, the composition may release 10 ppm·hours or more of $ClO_2$ gas, or 20 ppm·hours or more of $ClO_2$ gas to deodorize a produce.

As used herein, "disinfect" means to reduce the number of living bacteria. To determine whether produce is disinfected, produce that has undergone a disinfecting treatment, such as exposure to $ClO_2$ gas, can be compared to control produce that has not undergone the disinfecting treatment to determine whether bacterial burden has been reduced; and, if so, the produce will be considered to have been disinfected. Alternatively, the bacterial burden of a produce may be compared before and after treatment to determine whether the produce has been disinfected. A produce packaging film described herein may release any suitable amount of $ClO_2$ gas to disinfect produce disposed within packaging formed from the packaging film. For example, a film may release 10 parts per million (ppm) or greater $ClO_2$ gas into an interior volume defined by a package formed, at least in part, from the film. Typically, the film may release 50 ppm or greater $ClO_2$ gas to disinfect the produce. The amount of $ClO_2$ gas needed to effectively disinfect produce will depend, in part, on the nature of the produce. In addition, the time that the produce is exposed to $ClO_2$ gas will affect the ability of the $ClO_2$ gas to disinfect the produce. In some embodiments, the film releases an amount of $ClO_2$ gas for a time sufficient to expose the produce to 100 ppm·hours or greater of $ClO_2$ gas to disinfect the produce. For example, the film may release 150 ppm·hours or more of $ClO_2$ gas, or 200 ppm·hours or more of $ClO_2$ gas, to disinfect the produce.

As used herein, "sterilize" means to make free from bacteria or other living organisms. A multilayer medical device packaging film described herein may release any suitable amount of $ClO_2$ gas to sterilize a medical device disposed within a package formed by the film. For example, the film may release 200 parts per million (ppm) or greater $ClO_2$ gas into an interior volume defined by a package formed, at least in part, from the film. Typically, a composition may release 500 ppm or greater $ClO_2$ gas to sterilize the medical device. The amount of $ClO_2$ gas needed to effectively sterilize a medical device will depend, in part, on the nature of the device. In addition, the time that the medical device is exposed to $ClO_2$ gas will affect the ability of the $ClO_2$ gas to sterilize the device. In some embodiments, the film releases an amount of $ClO_2$ gas for a time sufficient to expose the medical device to 1000 ppm·hours or greater of $ClO_2$ gas to sterilize the device. For example, the film may release 1500 ppm·hours or more of $ClO_2$ gas, or 2000 ppm·hours or more of $ClO_2$ gas, to sterilize the medical device.

In some embodiments, the compositions described herein are substantially free of an amount of an acid-releasing compound capable of taking part in a reaction to yield an effective or significant amount of $ClO_2$ gas from the chlorite ions when the composition is exposed to moisture without being exposed to ultraviolet light, and are substantially free of an energy-activated catalyst capable of taking part in a reaction to yield an effective or significant amount of $ClO_2$ gas chlorite ions when the composition is exposed to ultraviolet light without being exposed moisture. That is, the composition does not contain the agent in question or contains the agent in question, but that the agent is arranged in the composition in such a way that it cannot take part in a reaction that produces an effective or significant amount of $ClO_2$ gas. For example, $TiO_2$ or other energy-activated catalysts may be present in the composition in a way that prevents contact with the reactants of the pathway by which $TiO_2$ facilitates the production of an effective or significant amount of $ClO_2$ gas. For example, if the composition comprises a multilayer film and one layer contains the chlorite ions and another layer comprises titanium dioxide, the titanium dioxide may not be capable of taking part in a reaction to yield an effective or significant amount of $ClO_2$ gas chlorite ions when the composition is exposed to ultraviolet light without being exposed moisture.

In some embodiments, the composition is substantially free of a metal oxide, such as $TiO_2$, that is capable of taking part in a reaction to yield an effective or significant amount of $ClO_2$ gas.

In some embodiments, the composition is substantially free of an organic acid-generating compound or acid that is capable of taking part in a reaction to yield a significant amount of $ClO_2$ gas.

In some embodiments, the composition capable of generating $ClO_2$ gas having a plurality of chlorite ions ($ClO_2^-$) dispersed therein is a solid.

In some embodiments, the composition capable of generating $ClO_2$ gas a plurality of chlorite ions ($ClO_2^-$) dispersed therein is a liquid.

In addition, the inventors demonstrate herein that method two-stage gas generation protocol can be used to generate $ClO_2$ gas from compositions containing polymers in which a chlorite salt is dispersed. The polymers may be used to form any suitable article, such as polymeric thin films, or layers or polymeric thin films, which can be used to package, for example, food products, pharmaceutical products, medical devices, and/or laboratory devices. Such packaging may be exposed to ultraviolet light and exposed to moisture to release controlled quantities of $ClO_2$ gas that can disinfect and/or deodorize an article disposed in a package formed by the film.

In some embodiments, a composition comprising chlorite ions capable of generating capable of generating $ClO_2$ gas after being exposed to a two-stage gas generation protocol is a coating composition or a layer coated on an article. The article may be a polymer, such a multilayer polymer film for packaging. Coatings may advantageously be applied to only a portion of a surface of the article or may be applied to an entire surface of the article. In some embodiments, the coating composition is water soluble or water dispersible.

The chlorite salt can also be introduced to the composition by using an inorganic support structure, such as, for example, alumina, silica, zeolite, clay and the like. In some embodiments, the inorganic support structure containing the chlorite salt is placed into a sachet. In other embodiments, the inorganic support structure containing the chlorite salt is placed in a polymer composition, in a composition for coating, or a coated layer.

Accordingly, in an aspect, this disclosure encompasses a composition capable of generating $ClO_2$ gas. The composition includes a plurality of chlorite ions ($ClO_2$) dispersed within a polymer. The composition is capable of generating more $ClO_2$ gas after being exposed to ultraviolet light than it is capable of generating after being exposed to visible light in the absence of ultraviolet light.

In some embodiments, after being exposed to ultraviolet light, the composition is activated so that it is capable of generating $ClO_2$ gas upon exposure to water. The activated composition may maintain such capability for at least one minute, at least one hour, at least one day, or at least two days. As used herein, a composition comprising chlorite ions is "activated" by UV light if the composition is capable of generating a significant amount of $ClO_2$ gas upon exposure to water relative to if the "activated" composition is not exposed to water.

In some embodiments, a chlorite salt is dispersed within a polymer, added to an inorganic support structure, included in a coating composition, or included in a coated layer. In some such embodiments, the chlorite salt is sodium chlorite, potassium chlorite, calcium chlorite, magnesium chlorite, lithium chlorite or ammonium chlorite. In some embodiments, the cation of the chlorate salt is an organic cation, and in some embodiments the cation of the chlorate salt is inorganic. In some embodiments, the chlorite salt is sodium chlorite. A "chlorite salt" as used herein is not limited to embodiments wherein the anion and cation form a solid crystal, but in fact encompass any form in which such salts are known to exist, including in aqueous or other solutions or dispersed within a polymeric matrix.

In some embodiments, the weight of the chlorite salt in the composition is at least 0.1% of the weight of the composition. In some embodiments, the weight of the weight of the chlorite salt in the composition is from about 10% to about 70% of the weight of the composition, such as from about 20% to about 60% of the weight of the composition.

In some embodiments, the chlorite salt is dispersed in a polymer, and the weight of the dispersed chlorite salt is at least 0.1% of the weight of the polymer and the dispersed chlorite salt together. In some embodiments, the weight of the dispersed chlorite salt is within the range of about 10% to about 70% of the weight of the polymer and the dispersed chlorite salt together. In some embodiments, the weight of the dispersed chlorite salt is within the range of about 20% to about 60% of the weight of the polymer and the dispersed chlorite salt together. In other embodiments, such as in packaging films, the weight of the dispersed chlorite salt is within the range of 0.1% to 15%, or 0.1% to 30%, of the weight of the polymer and the dispersed chlorite salt together. In other embodiments, the weight of the dispersed chlorite salt is within the range of about 1% to about 10%, or 1% to 20%, of the weight of the polymer and the dispersed chlorite salt together.

In some embodiments, the composition comprises a wavelength conversion component that emits a second wavelength of light that, in turn, generates $ClO_2$ gas when the wavelength conversion component is subjected to a different first wavelength of light. In some embodiments, the wavelength conversion component is an upconverting nanoparticle.

In some embodiments, the composition comprising chlorite ion dispersed in a polymer is in the form of a polymeric film. In some such embodiments, the polymeric film is a thin film having a thickness less than 25.4 microns. In some embodiments, the polymer is in the form of a polymeric sheet. In such embodiments, the polymeric sheet has a thickness of at least 25.4 microns. In some embodiments the thin film is a layer within a larger multilayer structure. In some embodiments, the thin film forms a monolayer structure. In some embodiments, more than one such thin film is included in a larger multilayer structure.

In some such embodiments, the thin film has a thickness in the range of about 100 nanometers to about 300 nanometers.

In some embodiments, the composition further includes one or more optically reflective layer(s) (i.e., light reflective layer(s)). In some such embodiments, the one or more optically reflective layer(s) is/are in contact with the polymeric film comprising the chlorite ion dispersed therein.

In some embodiments, the polymer comprising chlorite ion dispersed therein may be a UV-transparent polymer.

In some embodiments, the polymer comprising chlorite ion dispersed therein may be a melt processable polymer, an extrudable polymer, a polyethylene, a polypropylene, a polyolefin, an ethylene vinyl acetate copolymer, a polyvinyl chloride, an ionomer, a polyamide, a polyester, a polyvinyl alcohol, a polylactic acid, a polyvinylidene chloride, and mixtures and copolymers thereof.

In some embodiments, the polymer is a polyolefin homopolymer or copolymer. In such embodiments, the polymer is a polyethylene homopolymer or copolymer. In such embodiments, the polymer is an ethylene-based plastomer. In such embodiments, the polymer is an ethylene-based hexene plastomer. In other embodiments, the polymer is an ethylene vinyl acetate copolymer.

In another aspect, this disclosure encompasses packaging for an article. The article may be, for example, a food product, a pharmaceutical product, a laboratory device, or a medical device. Such packaging includes the compositions described above. In some embodiments, the disclosure encompasses a packaged article, such as a food product, pharmaceutical product, laboratory device or medical device, which includes the article packaged in such packaging.

In another aspect, this disclosure encompasses a laboratory device, a medical device, or any solid or other article where minimization of microbial burden is desired or necessary. The article includes a composition capable of generating $ClO_2$ gas, as described above. In some embodiments, the device or article is a rubber glove or catheter.

In another aspect, this disclosure encompasses a method for making a composition capable of generating $ClO_2$ gas. The method includes the step of dispersing a chlorite salt in a polymer, whereby a composition capable of generating $ClO_2$ gas is formed.

In some embodiments, this disclosure encompasses a method for disinfecting and/or deodorizing a food product, pharmaceutical product, laboratory device or medical device, comprising (a) positioning the product or device in or near a packaging article, wherein the packaging article comprises an interior surface, an exterior surface, and at least one layer comprising a composition capable of generating $ClO_2$ gas comprising a polymer having a plurality of chlorite ions ($ClO_2-$) dispersed therein; (b) performing a two-stage gas generation protocol to generate $ClO_2$ gas whereby the two-stage gas generation protocol comprises a first unit operation of exposing the at least one layer comprising a composition capable of generating $ClO_2$ gas to ultraviolet light and a second unit operation of exposure of the at least one layer comprising a composition capable of generating $ClO_2$ to moisture, whereby the composition releases $ClO_2$ gas. Operation of either the first unit or the second unit without the other does not result in the release of a significant amount of $ClO_2$ gas. In some embodiments, the packaging comprises a second layer. The first unit operation of exposing the at least one layer comprising a composition capable of generating $ClO_2$ gas to ultraviolet light may comprise laminating at least two layers of the packaging article together.

In another aspect, this disclosure encompasses a packaging article which includes an interior surface, an exterior surface and at least one layer comprising a composition capable of generating $ClO_2$ gas comprising a polymer having a plurality of chlorite ions ($ClO_2^-$) dispersed therein such that the composition generates $ClO_2$ gas after being exposed to a two-stage gas generation protocol comprising a first stage comprising exposure to ultraviolet light and a second stage comprising exposure to moisture. The composition does not generate a significant amount of $ClO_2$ gas when exposed to the first stage and not the second stage or when exposed to the second stage and not the first stage. The composition may further comprise a colorant, an opacifier, a flavorant, a perfume, an antiblocking agent, an antioxidant, an antistatic agent, an antifog agent, a slip agent, a process aid, a release agent or combinations thereof. In some embodiments, the composition comprises a chlorite salt. The chlorite salt may be selected from the group consisting of sodium chlorite, potassium chlorite, calcium chlorite, magnesium chlorite and ammonium chlorite. In some embodiments, the weight of the dispersed chlorite salt is within the range of 0.1% to 30%, or 1%-20%, of the total weight of the composition.

In some embodiments, packaging film includes a heat-seal layer that includes chlorite ion dispersed within the heat seal layer such that the heat-seal layer is capable of generating $ClO_2$ gas. The heat-seal layer forms the interior surface of the packaging film, when an article is packed within the film by heat sealing. The heat-seal layer may contact an article packaged within the film. If the article packaged in the film is a food product, the heat-seal layer may be a food contact layer. The packaging film may comprise one or more layers. The packaging film may comprise an oxygen barrier material. For purposes of the present disclosure, a packaging film includes a packaging sheet.

A packaging film comprising at least one layer comprising chlorite ions capable of generating $ClO_2$ gas when exposed to a two-stage gas generation protocol described herein may be used to form a bag, a pouch, a casing, a tray, a lidding film, an overwrap, a vacuum skin package, a shrink package, a thermoformed package or a vacuum package. The packaging film may be used to form a blister package, a label or a packaging insert.

In another aspect, this disclosure encompasses a method for disinfecting and/or deodorizing a food product, pharmaceutical product, laboratory device or medical device. The method includes the steps of positioning the food product, pharmaceutical product, laboratory device or medical device, in or near to a packaging article comprising at least one layer comprising a composition capable of generating $ClO_2$ gas as described above, and performing a two-stage gas generation protocol to generate $ClO_2$ gas whereby the two-stage gas generation protocol includes a first unit operation of exposing of the product or device to ultraviolet light followed by a second unit operation of exposure of the product or device to moisture, or alternatively, the two-stage gas generation protocol includes a first unit operation of exposing the product or device to moisture followed by a second unit operation of exposure of the product to ultraviolet light, or alternatively, the two-stage gas generation protocol includes a first unit operation of exposing the product or device to moisture simultaneously with a second unit operation of exposure of the product to ultraviolet light, whereby the packaging article releases $ClO_2$ gas that disinfects and/or deodorizes the product or device. The packaging article does not generate a significant amount of $ClO_2$ gas when exposed to the first stage and not the second stage or when exposed to the second stage and not the first stage. In other embodiments, a sachet is used to contain the compositions of the present invention. The sachet may comprise a chlorite salt or an inorganic support structure having a chlorite salt dispersed thereon and/or therein. The sachet can be placed in a package formed by a packaging article for releasing chloride dioxide upon exposure to a two-stage gas generation protocol. In other embodiments, a piece of a film, such as a strip of film, which contains a chlorite salt dispersed in a polymer matrix is placed in a package formed by a packaging article for releasing chloride dioxide upon exposure to a two-stage gas generation protocol.

In some embodiments, the step of exposing the composition or packaging to moisture is performed by contacting the packaging article with a humidified gas comprising water vapor. In some such embodiments, the humidified gas is heated above room temperature. In some such embodiments, the humidified gas includes steam. In some embodiments, ambient humidity can be used. In some embodiments, the water vapor is provided by the contents of the package. An exemplary example of the contents of the package that could provide the needed water vapor would be a food or food product.

In another aspect, this disclosure encompasses a method for generating $ClO_2$ gas. The method includes the steps of (a) exposing a composition including a plurality of chlorite ions ($ClO_2^-$) to ultraviolet (UV) light, and (b) subsequently exposing the composition to moisture whereby $ClO_2$ gas is generated. Alternatively, the method may include the steps of (a) exposing the composition including a plurality of chlorite ions ($ClO_2^-$) to moisture, and (b) subsequently exposing the composition to ultraviolet (UV) light, whereby $ClO_2$ gas is generated. Alternatively, the method may include the steps of (a) exposing the composition including a plurality of chlorite ions ($ClO_2^-$) to moisture, and (b) simultaneously exposing the composition to ultraviolet (UV) light, whereby $ClO_2$ gas is generated. The composition does not generate a significant amount of $ClO_2$ gas when exposed to step (a) and not step (b) or when exposed to step (b) and not step (a). In some embodiments, the composition includes a chlorite salt. In some such embodiments, the chlorite salt is sodium chlorite, potassium chlorite, calcium chlorite, magnesium chlorite, lithium chlorite or ammonium chlorite. In some such embodiments, the chlorite salt is sodium chlorite.

In some embodiments, the UV light has a wavelength in the range of about 200 nm to 400 nm. In some such embodiments, the UV light has a wavelength in the range of about 230 nm to 320 nm. In some such embodiments, the UV light has a wavelength in the range of about 240 nm to 280 nm.

In some embodiments, the composition is exposed to moisture by contacting the composition with humidified gas. The humidified gas may have any suitable relative humidity. For example, the relative humidity of the humidified gas may be within the range of about 1% to 100%. In some such embodiments, the relative humidity of the humidified gas is within the range of about 20% to 100%. In some such embodiments, the relative humidity of the humidified gas is within the range of about 60% to 100%. In some such embodiments, the relative humidity of the humidified gas is within the range of about 75% to 100%.

In some embodiments, the composition is exposed to UV light for a period of time that is greater than 10 milliseconds. In some such embodiments, the composition is exposed to UV light for a period of time that is greater than 10 seconds. In some such embodiments, the composition is exposed to UV light for a period of time that is greater than ten minutes.

In some embodiments, the steps of (a) exposing the composition including a plurality of chlorite ions to UV light, and (b) subsequently contacting the composition with water vapor, are separated by an intervening storage time. In some such embodiments, the intervening storage time is within the range of about one minute to about two days. In some such embodiments, the storage time is within the range of about one hour to about one day In some embodiments, the method further includes the step of drying the composition including a plurality of chlorite ions before exposing the composition to UV light. In some such embodiments, the step of drying the composition is performed by contacting the composition with a dry gas or subjecting the composition to a drying oven.

In some embodiments, the method further includes the step of heating the composition.

In some embodiments, the step of exposing the composition to ultraviolet light may be repeated one or more times, as can the step of subsequently contacting the composition with moisture to generate $ClO_2$ gas.

Compositions Comprising Chlorite Ions

The chlorite ions may be present in the compositions in the form of a salt. The compositions may include any suitable chlorite salt. Chlorite salts include both a chlorite anion and a cation. The cation can be an inorganic cation or an organic cation. For example, the cation may be any cation known in the art to be capable of forming a chlorite salt, including, without limitation, an alkali metal ion, and alkaline earth ion, a transition metal ion, a protonated primary amine, a protonated secondary amine, a protonated tertiary amine, a quaternary amine, or mixtures thereof.

The compositions may include one or more chlorite salts.

The compositions may include any suitable amount of chlorite salt. The amount of chlorite salt can be varied to help control the amount of $ClO_2$ that is generated. In non-limiting examples, the weight percent of the chlorite salt is, for example, 0.1%, 1%, 5%, 10%, 15%, 20%, 25%, 30%, 35%, 40%, 45%, 50%, 55%, 60%, 65% or 70% of the weight of the composition, or any amount in between. In some embodiments, the lower range of the weight of the chlorite salt may be, for example, 0.1%, 1%, 5%, 10%, 15%, 20%, 25%, 30%, 35%, 40%, 45%, 50%, 55%, 60%, or 65% of the weight of the composition, while the upper range of the weight of the chlorite salt may be 15%, 20%, 25%, 30%, 35%, 40%, 45%, 50%, 55%, 60%, 65%, or 70% of the weight of the composition. The disclosure encompasses all weight percentage ranges that are defined by any combination of these lower and upper bounds.

The compositions comprising chlorite ions may be free of an energy-activated catalyst and free of an acid-releasing compound capable of reacting with chlorite in the presence of water to generate $ClO_2$ gas.

The compositions may be substantially free of an energy-activated catalyst that is capable of taking part in a reaction to yield an effective or significant amount of $ClO_2$ gas and may be substantially free of an acid-releasing compound that is capable of taking part in a reaction to yield an effective or significant amount of $ClO_2$ gas.

The compositions may comprise an amount of one or both of an energy activated catalyst and an acid-releasing compound that is not sufficient to cause generation of a significant amount of $ClO_2$ gas upon exposure to UV radiation without exposure to water, in the case of an energy-activated catalyst, or upon exposure to water without exposure to UV radiation, in the case of an acid-releasing compound.

The compositions may comprise an amount of one or both of an energy activated catalyst and an acid-releasing compound that is not sufficient to cause generation of an effective amount of $ClO_2$ gas upon exposure to UV radiation without exposure to water, in the case of an energy-activated catalyst, or upon exposure to water without exposure to UV radiation, in the case of an acid-releasing compound.

In some embodiments, the compositions include less than 10 weight percent of a metal oxide, such as titanium dioxide, based on total weight of the composition. In certain particular embodiments, the amount of metal oxide in the composition is less than 5 weight percent, or less than 2 weight percent, based on total weight of the composition.

In some embodiments, the compositions may comprise a weight ratio of chlorite salt to metal oxide, such as titanium dioxide, of 3:1 or greater, such as 4:1, 5:1. 6:1, or 9:1 or greater, or any weight ratio encompassed within the foregoing ranges.

In some embodiments, the compositions comprise a polymer and the chlorite ion dispersed in the polymer. The composition may comprise any suitable polymer. The compositions may be used to form, or be in the form of, polymer films or may be formed into, or be in the form of, polymeric articles capable of releasing $ClO_2$ gas. The polymeric compositions may be coating compositions or coated layers.

The compositions may include any polymer known the art to be capable of forming thin films and/or to be used in packaging. Non-limiting examples of such polymers include a polyethylene, a polypropylene, a polyolefin, an ethylene vinyl acetate copolymer, a polyvinyl chloride, an ionomer, a polyamide, a polyester, a polyvinyl alcohol, a polylactic acid, a polyvinylidene chloride, and mixtures and copolymers thereof.

Inorganic Support

In some embodiments, the composition comprises a chlorite ion (for example, in the form of a chlorite salt) and an inorganic support. Any suitable inorganic support may be used. Examples of suitable inorganic supports include alumina, silica, zeolite, clay and the like. In some embodiments, the composition comprising the inorganic support structure and the chlorite salt is placed into a sachet. In some embodiments, the composition comprising the inorganic support and the chlorite salt is added to a polymer composition.

Coating

In some embodiments, a coating composition or a coated layer comprises the composition comprising the chlorite ions for generation of $ClO_2$ gas upon exposure to a two-stage gas generation protocol. Chlorite ions, such as in the form of one or more chlorite salt, may be disposed in any suitable coating composition and coated on any suitable article in any suitable manner.

In some embodiments, the coating composition may comprise one or more chlorite salt, one or more other suitable coating components, and one or more suitable solvents or diluents. In some embodiments, the one or more coating components are water soluble.

Suitable coating components may include materials that retain the chlorite ions on the article after the article is coated on the article. In some embodiments, the coating composition comprises a polymer or resin compatible with the article to be coated. Upon drying or curing of the coating, the coating preferably adheres to the article.

The coating composition may be applied in any suitable manner. For example, the article to be coated may be dipped in the coating composition or the coating composition may be sprayed, rolled, printed, or otherwise deposited on a surface of the article. The coating may be applied across an entire surface of the article or may be applied to one or more portions of the article. In some embodiments, the coating is pattern coated to coat certain portions of a surface of an article and to leave certain portions of the article uncoated.

Packaging Film

A packaging film may comprise a composition comprising a polymer and chlorite ions dispersed therein, as described herein. In some embodiments, the composition comprising the polymer and the chlorite ions forms a monolayer packaging film. In some embodiments, the composition comprising the polymer and the chlorite ions forms one or more layer of a multilayer packaging film.

In some embodiments where the film is a multilayer medical packaging film, the film comprises a barrier layer. In some embodiments where the film is a multilayer produce packaging film, the film does not comprise a barrier layer.

In many embodiments, the inner-most layer of the packaging film comprises the chlorite ions. In some embodiments, the chlorite ion-containing layer is proximate to the inner-most layer of the film and the inner-most layer of the film allows transmission of chlorine dioxide through the inner-most layer. Upon exposure of the chlorite ion-containing layer to UV radiation and moisture, $ClO_2$ gas can be released to contact an article, such as a medical device or produce, in a package produced by the packaging film. The amount of chlorite ion present in the packaging, the time and amount of exposure of the packaging to UV light and the time and amount of moisture to which the packaging is exposed can affect the amount of $ClO_2$ gas generated, and thus can affect the extent to which an article is deodorized or disinfected or whether the article is sterilized.

The packaging film may comprise any suitable number of layers. For example, the packaging film may comprise one or more of a sealing layer, a barrier layer, an abuse-resistant outer layer, an intermediate layer, a tie layer, and the like. The film may comprise one or more chlorite ion-containing layers.

Chlorite Ion Containing Layer

The chlorite ion-containing layer comprises a plurality of chlorite ions and a polymer composition. The chlorite ions may be present in the layer in the form of a salt. The layer may include any suitable chlorite salt. Chlorite salts include both a chlorite anion and a cation. The cation can be an inorganic cation or an organic cation. For example, the cation may be any cation known in the art to be capable of forming a chlorite salt, including, without limitation, an alkali metal ion, and alkaline earth ion, a transition metal ion, a protonated primary amine, a protonated secondary amine, a protonated tertiary amine, a quaternary amine, or mixtures thereof. In some embodiments, the chlorite salt is selected from sodium chlorite and potassium chlorite. The chlorite ion-containing layer may include one or more chlorite salts. For example, the chlorite ion-containing layer may include sodium chlorite and potassium chlorite.

The chlorite ion-containing layer may include any suitable amount of chlorite salt. The amount of chlorite salt can be varied to help control the amount of $ClO_2$ that is generated. In non-limiting examples, the weight percent of the chlorite salt is, for example, 0.1%, 1%, 5%, 10%, 15%, 20%, 25%, 30%, 35%, 40%, 45%, 50%, 55%, 60%, 65% or 70% of the weight of the composition, or any amount in between. In some embodiments, the lower range of the weight of the chlorite salt may be, for example, 0.1%, 1%, 5%, 10%, 15%, 20%, 25%, 30%, 35%, 40%, 45%, 50%, 55%, 60%, or 65% of the weight of the composition, while the upper range of the weight of the chlorite salt may be 15%, 20%, 25%, 30%, 35%, 40%, 45%, 50%, 55%, 60%, 65%, or 70% of the weight of the composition. The disclosure encompasses all weight percentage ranges that are defined by any combination of these lower and upper bounds.

The chlorite ion-containing layer may comprise any suitable polymer. In some embodiments, the layer comprises one or more of polyethylene, ethylene vinyl acetate, ethylene alpha-olefins, or polypropylene.

The chlorite ion-containing layer may be present in any suitable form. For example, the layer may be in the form of a coating layer or a film layer. If the chlorite ion-containing layer is in the form of a film layer, the film layer may be co-extruded, laminated or otherwise associated with one or more other layer of the film.

The chlorite ion-containing layer may have any suitable thickness. In some embodiments, the layer has a thickness of 25 micrometers or more when the chlorite ion-containing layer is in the form of a film layer. A chlorite ion-containing film layer may have any suitable amount of chlorite ion in the layer, such as those amounts discussed above. In some embodiments, the chlorite ion-containing film layer comprises a chlorite salt in an amount within a range from 0.1 weight percent to 25 weight percent relative to the total weight of the layer. For example, the chlorite ion-containing film layer may comprise a chlorite salt in an amount within a range from 5 weight percent to 20 weight percent relative to the total weight of the layer.

In some embodiments, a coating comprising chlorite ions is disposed on a substrate layer to form the chlorite ion-containing layer on the substrate layer. The coating may be disposed across an entire surface of the substrate layer or can be disposed across one or more portions of the substrate layer. The coating comprising chlorite ions may be advantageously applied to certain portions of the substrate layer to direct the generation of $ClO_2$ gas only to areas where generation of $ClO_2$ gas is desired. Such directed coating and gas generation, can provide cost savings relative to coatings applied across an entire surface, including across areas for which gas generation is not needed or desired.

Any suitable coating composition may be used to coat the substrate layer. For example, the coating composition may comprise one or more chlorite salt, one or more other suitable coating components, and one or more suitable solvents or diluents. In some embodiments, the one or more coating components are water soluble or water dispersible.

Suitable coating components may include materials that retain the chlorite ions on the substrate layer after the article is coated on the substrate layer. In some embodiments, the coating composition comprises a polymer or resin compatible with the substrate layer to be coated. Upon drying or curing of the coating, the coating preferably adheres to the substrate layer.

The coating composition may comprise any suitable polymer. In some embodiments, the coating composition comprises one or more of polyethylene, ethylene vinyl acetate, ethylene alpha-olefins, or polypropylene.

The coating compositions may include any suitable amount of chlorite ion, such as the amounts discussed above. In some embodiments, the chlorite ions are present in a salt, and the salt is present in an amount within a range from 0.1 weight percent to 30 weight percent relative to the total weight of the chlorine dioxide-producing layer. For example, the salt may present in an amount within a range from 10 weight percent to 20 weight percent relative to the total weight of the chlorite ion-containing layer.

The coating composition may be applied in any suitable manner. For example, the substrate layer to be coated may be dipped in the coating composition or the coating composition may be sprayed, rolled, printed, or otherwise deposited on a surface of the substrate layer. In some embodiments, the coating is pattern coated to coat certain portions of a surface of the substrate layer and to leave certain portions of the substrate layer uncoated.

Heat Sealing Layers

The films described herein may comprise a heat sealing layer. The terms "heat seal layer" and "sealing layer" are used interchangeably and refer to a layer capable of fusion bonding by conventional indirect heating means which generate sufficient heat on at least one film contact surface for conduction to the contiguous film contact surface and formation of a bond interface therebetween without loss of the film integrity. The bond interface between contiguous inner layers preferably has sufficient physical strength to withstand the packaging process and subsequent handling.

In some embodiments, the heat seal layer comprises a polyolefin. "Polyolefin" is used herein broadly to include polymers such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. Polyolefins may be made by a variety of processes well known in the art including batch and continuous processes using single, staged or sequential reactors, slurry, solution and fluidized bed processes and one or more catalysts including for example, heterogeneous and homogeneous systems and Ziegler, Phillips, metallocene, single site and constrained geometry catalysts to produce polymers having different combinations of properties. Such polymers may be highly branched or substantially linear and the branching, dispersity and average molecular weight and may vary depending upon the parameters and processes chosen for their manufacture in accordance with the teachings of the polymer arts.

In some embodiments, the heat seal layer comprises a cyclic olefin copolymer (COC), such as an ethylene norbornene copolymer.

In some embodiments, the heat seal layer comprises one or more of polyethylene, ethylene vinyl acetate, ethylene alpha-olefins, or polypropylene.

In some embodiments, the sealing layer comprises a blend of polymers to obtain suitable or desired properties.

In various embodiments, the sealing layer can facilitate formation of hermetically sealed packages when heat sealed.

In some embodiments, the sealing layer is the chlorite ion-containing layer that is capable of generating $ClO_2$ gas upon exposing the film to UV light and moisture. The sealing layer can form the inner-most layer of a package and can thus advantageously place the chlorite ions for generating $ClO_2$ gas in close proximity to an article packaged in the film or to be packaged in the film. The sealing layer may comprise any suitable amount of chlorite ion. However, increasing amounts of chlorite ion, for example in the form of chlorite salt, may interfere with the ability of the layer to seal. Typically, the heat seal layer will comprise less than about 70% by weight chlorite salt, such as 50% or less, 30% or less, 20% or less, or 10% or less. In some embodiments, the heat seal layer comprises a chlorite salt in an amount within a range from 0.1 weight percent to 25 weight percent relative to the total weight of the layer. For example, the heat seal layer comprises a chlorite salt in an amount within a range from 5 weight percent to 20 weight percent relative to the total weight of the layer.

A sealing layer may have any suitable thickness. In some embodiments, a sealing layer has a thickness of 25 micrometers or greater.

If chlorite ions are dispersed in a sealing layer or another layer, the polymer or polymers forming the layer are preferably transparent to UV radiation (e.g., at least 50% of UV light can be transmitted through the polymers forming the sealing layer). However, if the polymer is not particularly transparent to UV light, the intensity of the UV radiation to which the layer is exposed can be increased to expose the chlorite ions to sufficient UV radiation. In addition or alternatively, the thickness of the layer may be decreased to enhance the percentage of the thickness of the layer thorough which sufficient radiation penetrates and/or the concentration of the chlorite ions in the layer can be increased.

In some embodiments, a coating comprising chlorite ions is disposed on the heat seal layer to form the chlorite ion-containing layer on the heat seal layer. The coating may be disposed across an entire inner surface of the sealing layer or can be disposed across one or more portions of the sealing layer. For example, the coating may be applied to a portion of the sealing layer that is not involved in heat sealing. Accordingly, the presence of the chlorite ions, for example in the form of chlorite salts, will not adversely affect the heat sealability of the heat seal layer.

Barrier Layers

A packaging film as described herein may include one or more barrier layer. If included, a barrier layer preferably functions both as a gas barrier layer, and as a moisture barrier layer, although these functions may be provided by separate layers. A gas barrier layer is preferably an oxygen barrier layer, and is preferably a core layer positioned between and protected by surface layers. For example, an oxygen barrier layer can be in contact with a first surface layer and an adhesive layer or may be sandwiched between two tie layers, two surface layers, or a tie layer and a surface layer.

A gas barrier, such as a chlorine dioxide barrier or an oxygen barrier, is preferably selected to provide sufficiently diminished permeability of gases to protect a medical device disposed in the sealed packaging from undesirable deterioration or, for example, oxidative processes. For example, a film may comprise an oxygen barrier having an oxygen permeability that is low enough to prevent oxidation of medical devices to be packaged in the film. In some embodiments, a multilayer packaging film will have an oxygen transmission rate ($O_2TR$) of less than 150 $cm^3/m^2/24$ hours at 1 atmosphere and 23° C., such as less than 10 $cm^3/m^2$ per 24 hours at 1 atmosphere. To protect oxygen sensitive articles from deterioration from oxygen contact over time, the films may have an $O_2TR$ of less than 1, such as less than 0.1, less than 0.01, or less than 0.001 $cm^3/m^2$ per 24 hours at 1 atmosphere and 23° C.

A moisture barrier is preferably selected to provide a moisture permeability sufficiently diminished to protect an article disposed in the sealed packaging from undesirable deterioration. For example, a film may comprise a water barrier having a moisture permeability that is low enough to prevent deleterious effects upon packaged articles such as medical devices. A preferred film according to various embodiments will have a water vapor transmission rate (WVTR) of less than 15 $g/m^2$ per 24 hours at 38° C. and 90% RH. In some embodiments, a film has a WVTR of less than 1, less than 0.1, or less than 0.01 $g/m^2$ per 24 hours at 38° C. and 90% RH.

A barrier layer can comprise any suitable material and may be any suitable thickness. A gas barrier layer can comprise polyvinyl alcohol (PVOH), ethylene vinyl alcohol (EVOH), polyvinylidene chloride (PVDC), polyamide, polyester, polyalkylene carbonate, polyacrylonitrile, a nanocomposite, a metallized film such as aluminum vapor deposited on a polyolefin, etc., as known to those of skill in the art. Suitable moisture barrier layers include aluminum foil, PVDC, fluoropolymers like polychlorotrifluoroethylene (PCTFE), polyolefins such as HDPE, LLDPE and cyclic olefin copolymers (COC), and metallized films such as aluminum vapor deposited on a polyolefin, etc., as known to those of skill in the art. It is desirable that the thicknesses of the barrier layers be selected to provide the desired combination of the performance properties sought e.g. with respect to oxygen permeability, water vapor permeability, delamination resistance, etc.

A bulk layer may be provided to provide additional functionality such as stiffness or heat sealability or to improve machinability, cost, flexibility, barrier properties, etc. Preferred bulk layers comprise one or more polyolefins such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification. The bulk layer may be of any suitable thickness or may even be omitted for use in certain applications.

If a film comprises a moisture barrier, care may need to be taken to ensure that the chlorine dioxide producing layer (e.g., a chlorite ion-containing sealing layer or coating layer) of the film is capable of being exposed to sufficient moisture to release $ClO_2$ gas. In some embodiments, the atmosphere of the packaging manufacturing line can be controlled to ensure that the chlorite-containing layer is exposed to sufficient moisture. In some embodiments, the packaging may be in the form of a three-sided bag with the article (e.g., food product, pharmaceutical product, medical device, or other product) disposed in the bag prior to final sealing of the fourth side to seal the product in the bag. While the product is in the three-sided bag, moist gas such as a stream of nitrogen containing steam or heated water may be used to flush the bag and to provide sufficient moisture for generation of $ClO_2$ gas prior to final sealing. In some embodiments, the packaging films may be stored in a high moisture environment prior to being brought on-line for packaging.

Abuse-Resistant Outer Layer

The films described herein may include an outer layer. Since it is seen by the user/consumer, in both monolayer and multilayer embodiments, the exterior surface of the film preferably has desirable optical properties and may have high gloss. Also, it preferably withstands contact with sharp objects and provides abrasion resistance, and for these reasons it is often termed the abuse resistant layer. This exterior abuse-resistant layer may or may not also be used as a heat sealable layer and thus may comprise one or more suitable heat seal polymers such as polyethylene or polypropylene. As the exterior surface layer of the film, this layer most often is also the exterior layer of any package, bag, pouch or other container made from the film, and is therefore subject to handling and abuse e.g. from equipment during packaging, and from rubbing against other packages and shipping containers and storage shelves during transport and storage.

The exterior surface layer should be easy to machine (i.e. be easy to feed through and be manipulated by machines e.g. for conveying, packaging, printing or as part of the film or bag manufacturing process). Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may be resistance to burn through e.g. by impulse sealers or may be used as a heat sealing surface in certain package embodiments e.g. using overlap seals.

Suitable exterior surface layers may comprise: paper, oriented polyester, amorphous polyester, polyamide, polyolefin, cast or oriented nylon, polypropylene, or copolymers, or blends thereof. Oriented films of this or any other layer may be either uni-axially or bi-axially oriented. The exterior layer thickness is typically 0.5 to 2.0 mils. Thinner layers may be less effective for abuse resistance, however thicker layers, though more expensive, may advantageously be used to produce films having unique highly desirable puncture resistance and/or abuse resistance properties.

In some embodiments, the abuse layer is transparent to UV light.

Intermediate Layers

A packaging film described herein may include an intermediate layer. An intermediate layer is any layer between the exterior layer and the interior layer and may include oxygen barrier layers, tie layers or layers having functional attributes useful for the film structure or its intended uses. Intermediate layers may be used to improve, impart or otherwise modify a multitude of characteristics: e.g. printability for trap printed structures, machinability, tensile properties, flexibility, stiffness, modulus, designed delamination, easy opening features, tear properties, strength, elongation, optical, moisture barrier, oxygen or other gas barrier, radiation selection or barrier e.g. to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof. Suitable polyolefins may include: polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification, LDPE, HDPE, LLDPE, EAO, ionomer, ethylene methacrylic acif (EMA), ethylene acrylic acid (EAA), modified polyolefins e.g. anhydride grafted ethylene polymers, etc.

Tie Layers

A film as described herein may comprise one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. In some embodiments, adhesive layers comprise materials found in both the first and second layers. The adhesive layer may suitably be less than 10% and preferably between 2% and 10% of the overall thickness of the multilayer film.

Multilayer films can comprise any suitable number of tie or adhesive layers of any suitable composition. Various adhesive layers are formulated and positioned to provide a desired level of adhesive between specific layers of the film according to the composition of the layers contacted by the tie layers.

The interior, exterior, intermediate or tie layers may be formed of any suitable thermoplastic materials, for example, polyamides, polystyrenes, styrenic copolymers e.g. styrene-butadiene copolymer, polyolefins, and in particular members of the polyethylene family such as LLDPE, VLDPE, HDPE, LDPE, COC, ethylene vinyl ester copolymer or ethylene alkyl acrylate copolymer, polypropylenes, ethylene-propylene copolymers, ionomers, polybutylenes, alpha-olefin polymers, polyesters, polyurethanes, polyacrylamides, anhydride-modified polymers, acrylate-modified polymers, polylactic acid polymers, or various blends of two or more of these materials.

Optional Additives to Layers

Various additives may be included in the polymers utilized in one or more of the exterior, interior and intermediate or tie layers of packaging comprising the same. For example, a layer may be coated with an anti-block powder. Also, conventional anti-oxidants, antiblock additives, polymeric plasticizers, acid, moisture or gas (such as oxygen) scavengers, slip agents, colorants, dyes, pigments, organoleptic agents may be added to one or more film layers of the film or it may be free from such added ingredients Reflective Layers The packaging films may include one of more layers that reflect UV light. Examples of suitable materials for such layers include metallic oils or depositions like vacuum metallized or sputtered layers. The reflective layer could be applied as a coating where reflective particles such as metallic flakes are dispersed in a polymeric binder. The film may be configured such that the chlorite ion-containing layer is positioned between the reflective layer and the UV source when the film is exposed to UV radiation. In some such embodiments, the one or more reflective layer(s) is/are in contact with the polymeric film. The reflective layers may be optically engineered to maximize yield, by increasing UV exposure of the chlorite salts dispersed within the film (e.g., dispersed within a sealing layer or a coating disposed on the sealing layer).

In cases where the polymers or additives of one or more layers of the film are not transparent to UV light (e.g., block transmission of more than 50% of UV light) or reflect UV light, care may need to be taken to ensure that the chlorite ion-containing layer (e.g., seal layer or coating disposed on seal layer) can be exposed to sufficient amounts of UV radiation to generate $ClO_2$ gas upon subjecting the film to a two-stage gas generation protocol. In some embodiments, a packaging film is subjected to UV radiation prior to final sealing of the packaging to ensure that the chlorite ion-containing layer is subjected to sufficient UV radiation to generate $ClO_2$ gas upon subjecting the film to a two-stage gas generation protocol. For example, the packaging manufacturing line can be equipped with an appropriate UV emitting source to allow in-line UV irradiation of the chlorite ion-containing layer.

Methods of Manufacture

The packaging films described herein may be made in any suitable manner, such as by conventional processes. Processes to produce flexible films may include e.g. cast or blown film processes, or extruding processes.

Packages may be formed from films in any suitable manner. In some embodiments, the packages are formed by heat sealing a film to itself or another suitable film. In some embodiments, packages such as pouches are thermoformed from the films. In some embodiments, films are heat sealed across an opening of a container.

Film Thickness

A packaging film described herein may have any suitable thickness. In some embodiments, the packaging film has a total thickness of less than about 50 mils, more preferably the film has a total thickness of from about 1.0 to 10 mils (25-250 microns ($\mu$), such as from about 1 to 5 mils, or from about 2 to 3.5 mils. For example, entire multilayer films or any single layer of a multilayer film can have any suitable thicknesses, including 1, 2, 3, 4, 5, 6, 7, 8, 9, 10 or 50 mils, or any increment of 0.1 or 0.01 mil therebetween.

In some embodiments, the packaging films are as thick as 50 mils (1270 microns) or higher, or as thin as 1 mil (25.4 microns) or less. In various embodiments, the packaging films have a thickness of between about 2-4 mil (51-102 microns).

Tearing Aid or Tear Initiator

The packaged articles that include an article disposed within sealed packaging may include a tearing aid or tear initiator such as a notch. Examples of tearing aids or tear initiators include notches, slits, perforations, surface roughened portions, etc. Such tear initiators may be used on one or more edges of a package such as a pouch.

Advantageously the tear initiator may be used with scoring e.g. mechanical or laser scoring of one or more layers, preferably the other abuse resistance layer, to create a tear directing line which facilitates opening.

Examples of Embodiments of Multilayer Films—Produce Packaging Films

In some embodiments, a multilayer produce film comprises a first layer, and a chlorine dioxide-producing layer. The chlorine dioxide-producing layer comprises a polymer composition and a plurality of chlorite ions. The chlorine dioxide-producing layer is substantially free of an energy-activated catalyst and is substantially free of an acid-releasing compound. In some embodiments, the plurality of chlorite ions are present in a salt selected from the group consisting of sodium chlorite, potassium chlorite, and mixtures thereof. In some embodiments, the film has an oxygen transmission rate of at least 775 $cm^3/m^2/24$ hours (50 $cm^3/100$ $m^2/24$ hours), such as an oxygen transmission rate of at least 3100 $cm^3/m^2/24$ hours (200 $cm^3/100$ $m^2/24$ hours). In some embodiments, the first layer is an abuse-resistant layer, wherein the abuse-resistant layer is UV-light transparent.

In some embodiments, the chlorine dioxide-producing layer is a coating having a thickness less than 15 In some embodiments, the coating comprises at least one of polyethylene, ethylene vinyl acetate, ethylene alpha-olefins, or polypropylene. In some embodiments, the coating comprises a chlorite salt in an amount within a range from 0.1 weight percent to 20 weight percent relative to the total weight of the chlorine dioxide-producing layer. For example, the coating comprises a chlorite salt in an amount within a range from 1 weight percent to 15 weight percent relative to the total weight of the chlorine dioxide-producing layer.

In some embodiments, the chlorine-dioxide layer may be a film layer and has a thickness of at least 25 $\mu$m. In such embodiments, the polymer composition may comprise at least one of polyethylene, ethylene vinyl acetate, ethylene alpha-olefins, or polypropylene. The plurality of chlorite ions may be present in a salt, and the salt may be present in an amount within a range from 0.1 weight percent to 20 weight percent relative to the total weight of the chlorine dioxide-producing layer, such as within a range from 1 weight percent to 15 weight percent relative to the total weight of the chlorine dioxide-producing layer.

In some embodiments, the multilayer produce film has a layer composition in the following sequence: (i) the chlorine dioxide-producing layer; (ii) a layer of polyethylene; (iii) a layer of adhesive; and (iv) the first layer comprising oriented polypropylene. The film may also have optional additional layers dispersed within the sequence.

In some embodiments, the multilayer produce film has a layer composition in the following sequence: (i) the chlorine dioxide-producing layer; (ii) the first layer comprising oriented polypropylene; (iii) a layer of adhesive; and (iv) a second layer of oriented polypropylene. The film may also have optional additional layers dispersed within the sequence.

In some embodiments, a produce package comprises a sidewall comprising the multilayer produce film. The produce package comprises an interior volume defined, at least in part, by an inside surface of the sidewall. In some embodiments, the chlorine dioxide-producing layer is proximate the inside surface of the sidewall. In some embodiments, the sidewall comprises a heat seal of the chlorine dioxide-producing layer.

Examples of Embodiments of Multilayer Films—Medical Packaging Films

In some embodiments, a multilayer medical packaging film comprises a first layer, and a chlorine dioxide-producing layer. The chlorine dioxide-producing layer comprises a polymer composition and a plurality of chlorite ions. The chlorine dioxide-producing layer is substantially free of an energy-activated catalyst and is substantially free of an acid-releasing compound. In some embodiments, the plurality of chlorite ions are present in a salt selected from the group consisting of sodium chlorite, potassium chlorite, and mixtures thereof. In some embodiments, the first layer is an oxygen barrier layer comprising aluminum foil, metal coated polymer, metal oxide coated polymer, or an aromatic polyamide polymer. In some embodiments, the first layer is an oxygen barrier layer comprising an ethylene vinyl alcohol copolymer, a polyvinylidene chloride copolymer, or an aliphatic polyamide. In some embodiments, the first layer is an outer layer proximate the chlorine dioxide-producing layer, wherein the outer layer comprises at least one of polyethylene or polypropylene. In some embodiments, the first layer is an abuse-resistant layer, wherein the abuse-resistant layer is UV-light transparent.

In some embodiments, the chlorine dioxide-producing layer is a coating having a thickness less than 15 µm. In some embodiments, the coating comprises at least one of polyethylene, ethylene vinyl acetate, ethylene alpha-olefins, or polypropylene. In some embodiments, the coating comprises a chlorite salt in an amount within a range from 0.1 weight percent to 30 weight percent relative to the total weight of the chlorine dioxide-producing layer. For example, the coating comprises a chlorite salt in an amount within a range from 10 weight percent to 20 weight percent relative to the total weight of the chlorine dioxide-producing layer.

In some embodiments, the chlorine dioxide-producing layer has a thickness of at least 25 µm. In such embodiments, the polymer composition may comprise at least one of polyethylene, ethylene vinyl acetate, ethylene alpha-olefins, or polypropylene. The plurality of chlorite ions may be present in a salt, and the salt may be present in an amount within a range from 0.1 weight percent to 25 weight percent relative to the total weight of the chlorine dioxide-producing layer, such as within a range from 5 weight percent to 20 weight percent relative to the total weight of the chlorine dioxide-producing layer.

In some embodiments, the medical package comprises a sidewall comprising the multilayer medical packaging film. The medical package comprises an interior volume defined by an inside surface of the sidewall. In some embodiments, the chlorine dioxide-producing layer is proximate the inside surface of the sidewall.

In some embodiments, the multilayer medical packaging film has a layer composition in the following sequence: (i) a layer of polyethylene; (ii) the chlorine dioxide-producing layer; (iii) a tie layer; (iv) the first layer comprising an oxygen barrier layer; (v) a tie layer; and (vi) an abuse layer. The film may also have optional additional layers dispersed within the sequence.

Examples of Embodiments of Multilayer Films—Schematic Drawings

Referring now to FIG. 1, a multilayer film 100 is shown. The film 100 includes a first layer 10, which may be an outer layer (as depicted) but can be an inner layer or a layer between an inner layer and an outer layer. The film 100 also includes a chlorite ion-containing layer 20 that contains a polymer composition and chlorite ions. The chlorite ion-containing layer 20 can be a film layer or a coating layer. The depicted film 100 includes optional intervening layers 32, 34, 36, and 38.

Figure 2:
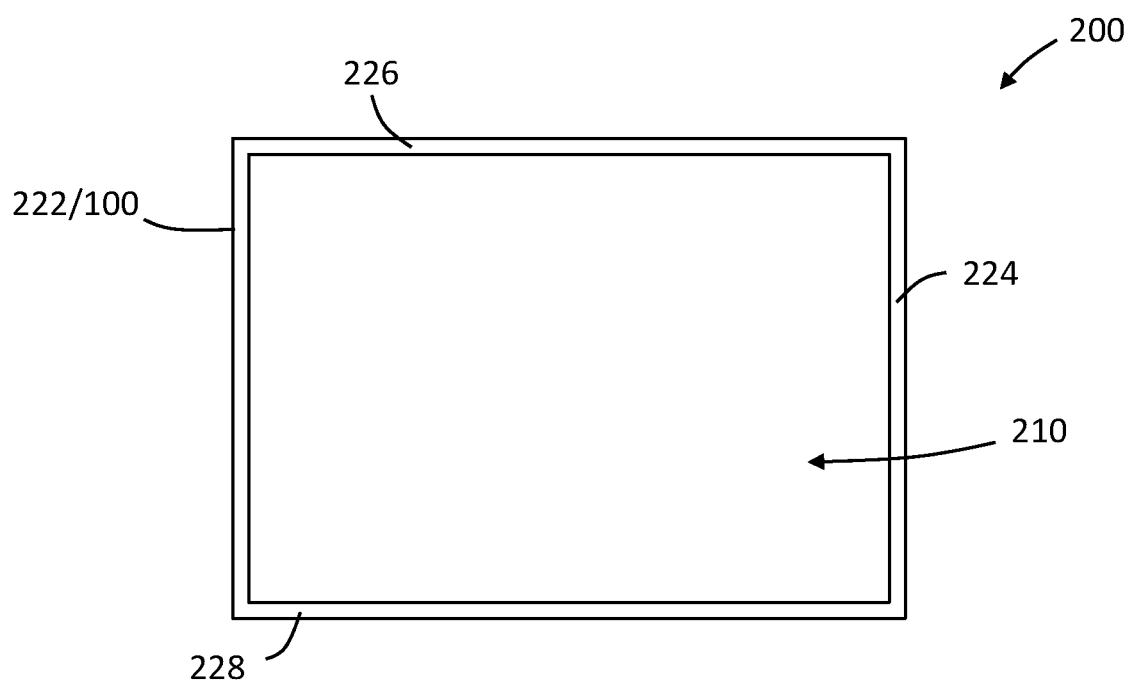
FIG. 2 is a schematic sectional view of an embodiment of a medical package.

Referring now to FIG. 2, a package 200 is shown. The depicted package 200 includes first 222, second 224, third 226, and fourth 228 sidewalls that at least partially define an interior volume 210 of the package 200. The first sidewall 222 comprises a multilayer packaging film 100 comprising a chlorite ion-containing layer. The other sidewalls 224, 226, 228 may or may not include a multilayer packaging film having a chlorite ion-containing layer. An article (not shown) may be disposed in the interior volume 210 of the package 200.

Packaged Products

Any suitable article may be disposed in a packaging described herein. Examples of suitable articles include food products, pharmaceutical products, laboratory devices, and medical devices. When such packaging that has been activated by exposure to ultraviolet light is subsequently contacted with water vapor, it releases $ClO_2$ gas to contact the packaged product or device. The $ClO_2$ gas may disinfect and/or deodorize the product or device.

Examples of suitable produce that may be packaged in a film described herein include lettuce, grapes, spinach, or the like.

Any suitable medical device may be disposed in a package comprising the multilayer packaging film described herein. For example, catheters such as balloon dilatation catheters, guide catheters, aspiration catheters, and diagnostic catheters; vacutainers; yankauers; enteral feeding kits; dressing gowns and drapes; coronary stents; surgical tools and equipment; or the like may be disposed within a sealed package as described herein. Preferably, the packaging generates a sufficient amount of $ClO_2$ gas for a sufficient amount of time after being exposed to a two-stage gas generation protocol to sterilize the medical device.

Two-Stage Gas Generation

A composition comprising chlorite ions described herein may be subjected to a two-stage $ClO_2$ gas generation protocol comprising exposure to UV light and moisture in any suitable manner. The compositions may be first activated by exposure to ultraviolet light. After an optional storage period, the compositions may then be contacted with moisture such as water vapor, resulting in the generation of $ClO_2$ gas. The amount of $ClO_2$ generated can be regulated by, for example, varying the wavelength and exposure time of the ultraviolet light, the amount of water vapor (moisture) present, the concentration of chlorite salts in the composition, or the length of the storage period.

In some embodiments, the UV light has a wavelength in the range of about 200 nm to 400 nm. In some such embodiments, the UV light has a wavelength in the range of about 230 nm to 320 nm. In some such embodiments, the UV light has a wavelength in the range of about 240 nm to 280 nm. Preferably, the UV light includes light having a wavelength of 254 nm.

The source of UV light is preferably an artificial source, such as a lamp, rather than sunlight. In some embodiments, a UV lamp is positioned on a packaging manufacturing line to expose a film comprising a composition as described herein to UV light before, during or after an article is disposed in a package formed, at least in part, from the film.

In some embodiments, the composition is exposed to UV light for a period of time that is greater than 10 milliseconds. In some such embodiments, the composition is exposed to UV light for a period of time that is greater than 10 seconds. In some such embodiments, the composition is exposed to UV light for a period of time that is greater than ten minutes.

In some embodiments, the step of exposing the composition to ultraviolet light may be repeated one or more times, as can the step of subsequently contacting the composition with moisture to generate $ClO_2$ gas.

In some embodiments, a packaged device, package or film is exposed to humidified gas. The humidified gas may have any suitable relative humidity. For example, the relative humidity of the humidified gas is within the range of about 1% to 100%. In some such embodiments, the relative humidity of the humidified gas is within the range of about 20% to 100%. In some such embodiments, the relative humidity of the humidified gas is within the range of about 60% to 100%. In some such embodiments, the relative humidity of the humidified gas is within the range of about 75% to 100%.

In some embodiments, the steps of (a) exposing the composition including a plurality of chlorite ions to UV light, and (b) subsequently contacting the composition with water vapor, are separated by an intervening storage time. In some such embodiments, the intervening storage time is within the range of about one minute to about two days. In some such embodiments, the storage time is within the range of about one hour to about one day.

In some embodiments, the method further includes the step of drying the composition including a plurality of chlorite ions before exposing the composition to UV light. In some such embodiments, the step of drying the composition is performed by contacting the composition with a dry gas or subjecting the composition to a drying oven.

In some embodiments, the method further includes the step of heating the composition.

In some embodiments, a method for generating $ClO_2$ gas includes the steps of (a) exposing a composition including a plurality of chlorite ions ($ClO_2^-$) to ultraviolet (UV) light, and (b) subsequently exposing the composition to moisture, whereby $ClO_2$ gas is generated. Alternatively, the method includes the steps of (a) exposing a composition including a plurality of chlorite ions ($ClO_2^-$) to moisture, and (b) subsequently exposing the composition to ultraviolet (UV) light. The composition may or may not include a polymer or material suitable for use in packaging. In some embodiments, the composition includes a chlorite salt, as defined above. Optionally, these steps may be repeated one or more times to generate additional amounts of $ClO_2$ gas.

The wavelength and/or exposure time of the UV light and the conditions under which the water vapor is delivered to the composition may be varied to control the yield and/or rate of production of $ClO_2$.

Optionally, the steps of (a) exposing the composition including a plurality of chlorite ions to UV light, and (b) subsequently contacting the composition to moisture, or the steps of (a) exposing the composition including a plurality of chlorite ion to moisture, and (b) subsequently exposing the composition to UV light are separated by an intervening storage time. The length of the storage time may also be varied to control the yield and/or rate of production of $ClO_2$. The yield and/or production rate may also be controlled by varying the temperature of the composition, or by including a sensitizing agent in the composition, as described above.

A number of aspects have been disclosed herein. A summary of a few selected aspects is provided below.

1. A composition capable of generating $ClO_2$ gas, comprising a polymer having a plurality of chlorite ions ($ClO_2^-$) dispersed therein, wherein the composition generates $ClO_2$ gas after being exposed to a two-stage gas generation protocol comprising a first stage comprising exposure of the chlorite ions to ultraviolet light and a second stage comprising exposure of the chlorite ions to moisture.

2. The composition of aspect 1, wherein the composition generates more $ClO_2$ gas in a two-stage gas generation protocol than the composition generates in a single-stage gas generation protocol.

3. The composition of aspect 1 or claim 2, wherein the second stage precedes the first stage.

4. The composition of any of aspects 1-3, wherein the composition is substantially free of an energy-activated catalyst comprising a metal oxide and is substantially free of hydronium ions.

5. A composition comprising a polymer having a plurality of chlorite ions ($ClO_2^-$) dispersed therein, wherein the composition is substantially free of an energy-activated catalyst comprising a metal oxide and is substantially free of hydronium ions.

6. The composition of any of aspect 1-5, wherein a chlorite salt is dispersed in the polymer.

7. The composition of aspect 6, wherein the chlorite salt is selected from the group consisting of sodium chlorite, potassium chlorite, calcium chlorite, magnesium chlorite, lithium chlorite, and ammonium chlorite.

8. The composition of aspect 6, wherein the chlorite salt is sodium chlorite.

9. The composition of any of aspects 6-8, wherein the weight of the dispersed chlorite salt is at least 0.1% of the total weight of the composition.

10. The composition of aspect 9, wherein the weight of the dispersed chlorite salt is within the range of about 1% and 15% of the total weight of the composition.

11. The composition of aspect 10, wherein the weight of the dispersed chlorite salt is within the range of about 1% and 10% of the total weight of the composition.

12. The composition of aspect 9, wherein the weight of the dispersed chlorite salt is less than about 10% of the total weight of the composition.

13. The composition of aspect 9, wherein the weight of the dispersed chlorite salt is within the range of about 1% to about 10% of the total weight of the composition.

14. The composition of any of aspects 1-13, wherein at least one of the chlorite ions is transformed to an activated state by UV light.

15. The composition of any of aspects 1-14, wherein the composition is a solid.

16. The composition of any of aspects 1-14, wherein the composition is a liquid.

17. The composition of aspect 15, wherein the polymer is in the form of a polymeric film.

18. The composition of any of aspects 1-17 wherein the polymer is a UV-transparent polymer.

19. The composition of any of aspects 1-18, wherein the polymer is selected from the group consisting of a melt processable polymer, an extrudable polymer, a polyethylene, a polypropylene, a polyolefin, an ethylene vinyl acetate copolymer, a polyvinyl chloride, an ionomer, a polyamide, a polyester, a polyvinyl alcohol, a polylactic acid, a polyvinylidene chloride, and mixtures thereof.

20. A laboratory or medical device, comprising the composition of any of aspects 1-19.

21. The laboratory or medical device of aspect 20, wherein the device is a catheter or a glove.

22. A method for disinfecting and/or deodorizing a food product, pharmaceutical product, laboratory device or medical device, comprising positioning the product or device in or near a packaging article, wherein the packaging article comprises an interior surface, an exterior surface, and at least one layer comprising a composition capable of generating $ClO_2$ gas comprising a polymer having a plurality of chlorite ions ($ClO_2$—) dispersed therein;

performing a two-stage gas generation protocol to generate $ClO_2$ gas whereby the two-stage gas generation protocol comprises a first unit operation of exposing the at least one layer comprising a composition capable of generating $ClO_2$ gas to ultraviolet light and a second unit operation of exposure of the at least one layer comprising a composition capable of generating $ClO_2$ to moisture, whereby the composition releases $ClO_2$ gas.

23. The method of aspect 22, wherein the step of exposing the at least one layer comprising a composition capable of generating $ClO_2$ gas to moisture is performed by contacting the packaging article with a humidified gas.

24. The method of aspect 22, wherein the moisture is in the ambient air or originates from the food product, pharmaceutical product, laboratory device or medical device.

25. The method of aspect 23, wherein the humidified gas is heated above 23° Celsius.

26. The method of aspect 23, wherein the humidified gas comprises steam.

27. The method of aspect 22, wherein the packaging article comprises a second layer.

28. The method of aspect 27, wherein the first unit operation of exposing the at least one layer comprising a composition capable of generating $ClO_2$ gas to ultraviolet light further comprises laminating at least two layers of the packaging article together.

29. A method of generating $ClO_2$ gas, comprising:
(a) exposing a composition comprising a plurality of chlorite ions ($ClO_2^-$) to ultraviolet (UV) light; and
(b) subsequently contacting the composition with moisture.

30. The method of aspect 29, wherein the composition comprises a chlorite salt.

31. The method of aspect 30, wherein the chlorite salt is selected from the group consisting of sodium chlorite, potassium chlorite, calcium chlorite, magnesium chlorite, lithium chlorite, and ammonium chlorite.

32. The method of aspect 31, wherein the chlorite salt is sodium chlorite.

33. The method of any of aspects 29-32, wherein the UV light has a wavelength in the range of about 200 nm to 400 nm.

34. The method of aspect 33, wherein the UV light has a wavelength in the range of about 230 nm to 320 nm.

35. The method of aspect 34, wherein the UV light has a wavelength in the range of about 240 nm to 280 nm.

36. The method of any aspects 29-35, wherein the moisture is above 23° Celsius.

37. The method of any of aspect 29-36, wherein the moisture is humidified gas having a relative humidity within the range of about 20% to 100%.

38. The method of aspect 37, wherein the relative humidity of the humidified gas is within the range of about 45% to 100%.

39. The method of aspect 38, wherein the relative humidity of the humidified gas is within the range of about 75% to 100%.

40. The method of any of aspects 29-39, wherein the composition is exposed to UV light for a period of time that is greater than 10 milliseconds.

41. The method of aspect 40, wherein the composition is exposed to UV light for a period of time that is greater than one second.

42. The method of aspect 41, wherein the composition is exposed to UV light for a period of time that is greater than ten minutes.

43. The method of any of aspects 29-42, wherein the steps of (a) exposing the composition comprising a plurality of chlorite ions to UV light, and (b) subsequently contacting the composition with water vapor are separated by an intervening period of time, wherein the intervening period of time is at least one minute.

44. The method of aspect 43, wherein the intervening period of time is at least one hour.

45. The method of aspect 44, wherein the intervening period of time is within the range of about one hour to about 24 hours.

46. The method of any of aspects 29-45, further comprising the step of drying the composition comprising a plurality of chlorite ions before exposing the composition to UV light.

47. The method of aspect 46, wherein the step of drying the composition is performed by contacting the composition with a dry gas.

48. The method of any of aspects 29-47, further comprising the step of heating the composition comprising a plurality of chlorite ions.

49. The method of any of aspects 29-48, wherein the step of exposing the composition to ultraviolet light, the step of subsequently contacting the composition with moisture, or both, are repeated one or more times.

50. A packaging article comprising:
an interior surface,
an exterior surface, and
at least one layer comprising a composition capable of generating $ClO_2$ gas comprising a polymer having a plurality of chlorite ions ($ClO_2^-$) dispersed therein, wherein the composition generates $ClO_2$ gas after being exposed to a two-stage gas generation protocol comprising a first stage comprising exposure to ultraviolet light and a second stage comprising exposure to moisture.

51. A packaging article comprising:
an interior surface,
an exterior surface, and
at least one layer comprising a composition comprising a polymer having a plurality of chlorite ions ($ClO_2^-$) dispersed therein, wherein the composition is substantially free of an energy-activated catalyst comprising a metal oxide and is substantially free of hydronium ions.

52. The packaging article of aspects 50 or 51, wherein the polymer comprises a polyolefin homopolymer or copolymer.

53. The packaging article of aspect 52, wherein the polymer comprises a polyethylene homopolymer or copolymer.

54. The packaging article of aspect 53, wherein the polymer comprises an ethylene-based plastomer.

55. The packaging article of aspect 54, wherein the polymer comprises an ethylene-based hexene plastomer.

56. The packaging article of aspects 50 or 51, wherein the polymer comprises an ethylene vinyl acetate copolymer.

57. The packaging article of any of aspects 50-56, wherein the at least one layer comprising a composition capable of generating $ClO_2$ gas is a heat-seal layer.

58. The packaging article of any of aspects 50-57, wherein the at least one layer comprising a composition capable of generating $ClO_2$ gas is the interior surface.

59. The packaging article of any of aspects 50-58, wherein the article is a monolayer film, a multilayer film, a monolayer sheet, a multilayer sheet or a combination thereof.

60. The packaging article of any of aspects 50-58, wherein the article is a monolayer film or a multilayer film each having a thickness of less than 10 mil.

61. The packaging article of any of aspects 50-58, wherein the article is a monolayer sheet or a multilayer sheet each having a thickness of at least 10 mil.

62. The packaging article of aspects 50-61, wherein the article is a monolayer film, a multilayer film, a monolayer sheet, or a multilayer sheet each comprising an oxygen barrier material.

63. The packaging article of any of aspects 50-62, wherein the article is a bag, a pouch, a casing, a tray, a lidding film, an overwrap, a vacuum skin package, a shrink package, a thermoformed package, or a vacuum package.

64. The packaging article of any of aspects 50-62, wherein the article is a food package.

65. The packaging article of any of aspects 50-62, wherein the article is a blister package.

66. The packaging article of any of aspects 50-62, wherein the article is a coating.

67. The packaging article of aspect 66, wherein the polymer is water soluble.

68. The packaging article of any of aspects 50-62, wherein the article is a label.

69. The packaging article of any of aspects 50-62, wherein the article is a packaging insert.

70. The packaging article of any of aspects 50-69, further comprising an interior volume, wherein the composition generates less than 0.1 ppm $ClO_2$ gas in the interior volume as measured in a one-stage gas generation protocol comprising exposure of the chlorite ions to ultraviolet light or exposure of the chlorite ions to moisture.

71. The packaging article of any of aspects 50-70, further comprising an interior volume, wherein the composition generates more than 0.5 ppm $ClO_2$ gas as measured in a two-stage gas generation protocol comprising a first stage comprising exposure of the chlorite ions to ultraviolet light and a second stage comprising exposure of the chlorite ions to moisture.

72. The packaging article of any of aspects 50-71, wherein the composition further comprises a colorant, an opacifier, a flavorant, a perfume, an antiblocking agent, an antistatic agent, an antifog agent, a slip agent, a process aid, a release agent, or combinations thereof.

73. The packaging article of any of aspects 50-72, wherein the composition comprises a chlorite salt.

74. The packaging article of aspect 73, wherein the chlorite salt is selected from the group consisting of sodium chlorite, potassium chlorite, calcium chlorite, magnesium chlorite, and ammonium chlorite.

75. The packaging article of aspect 73, wherein the chlorite salt is sodium chlorite.

76. The packaging article of any of aspects 73-75, wherein the weight of the dispersed chlorite salt is at least 0.1% of the total weight of the composition.

77. The packaging article of aspect 76, wherein the weight of the dispersed chlorite salt is within the range of about 1% and 15% of the total weight of the composition.

78. The packaging article of aspect 77, wherein the weight of the dispersed chlorite salt is within the range of about 1% and 10% of the total weight of the composition.

79. The packaging article of any of aspects 50-78, wherein the polymer is a UV-transparent polymer.

80. The packaging article of aspect 50, wherein the composition is substantially free of an energy-activated catalyst comprising a metal oxide and is substantially free of hydronium ions.

81. A film comprising:
at least one layer comprising a composition capable of generating $ClO_2$ gas comprising a polymer having a plurality of chlorite ions ($ClO_2$—) dispersed therein, wherein the composition generates $ClO_2$ gas after being exposed to a two-stage gas generation protocol comprising a first stage comprising exposure to ultraviolet light and a second stage comprising exposure to moisture.

82. The film of aspect 81, wherein the composition generates more $ClO_2$ gas in a two-stage gas generation protocol than the composition generates in a single-stage gas generation protocol.

83. The composition of any of aspects 81-82, wherein the second stage precedes the first stage.

84. A film comprising:
a polymer having a plurality of chlorite ions ($ClO_2$) dispersed therein, wherein the composition is substantially free of an energy-activated catalyst comprising a metal oxide and is substantially free of hydronium ions.

85. The film of any of aspects 81-83, wherein the composition is substantially free of an energy-activated catalyst comprising a metal oxide and is substantially free of hydronium ions.

86. The film of any of aspects 81-85, wherein the film is a multilayer film.

87. The film of aspect 86, wherein the multilayer film comprises at least one barrier layer, one sealant layer, and one abuse layer.

88. The film of aspect 87, wherein the abuse layer comprises a polyamide, a polyester, or a polyolefin.

89. The film of any of aspects 87-88, wherein the barrier layer comprises polyamide, ethylene vinyl alcohol, or metal.

90. The film of any of aspects 81-89, further comprising a UV reflective layer.

91. The film of aspect 90, wherein the composition capable of generating $ClO_2$ gas is in the sealant layer and the UV reflective layer is adjacent to the sealant layer.

92. The film of any of aspects 81-91, wherein the composition comprises a chlorite salt dispersed in the polymer.

93. The film of aspect 92, wherein the chlorite salt is selected from the group consisting of sodium chlorite, potassium chlorite, calcium chlorite, magnesium chlorite, lithium chlorite, and ammonium chlorite.

94. The film of aspect 92, wherein the chlorite salt is sodium chlorite.

95. The film of any of aspects 92-94, wherein the weight of the dispersed chlorite salt is at least 0.1% of the total weight of the composition.

96. The film of aspect 95, wherein the weight of the dispersed chlorite salt is within the range of about 1% and 15% of the total weight of the composition.

97. The film of aspect 96, wherein the weight of the dispersed chlorite salt is within the range of about 1% and 10% of the total weight of the composition.

98. The film of any of aspects 81-97, wherein at least one of the chlorite ions is transformed to an activated state by UV light.

99. The film of any of aspects 81-98 wherein the polymer is a UV-transparent polymer.

100. The film of any of aspects 81-99, wherein the polymer is selected from the group consisting of a polyethylene, a polypropylene, a polyolefin, an ethylene vinyl acetate copolymer, a polyvinyl chloride, an ionomer, a polyamide, a polyester, a polyvinyl alcohol, a polylactic acid, a polyvinylidene chloride, and mixtures thereof.

101. A composition capable of generating $ClO_2$ gas, comprising an inorganic support structure and a plurality of chlorite ions ($ClO_2^-$), wherein the composition generates $ClO_2$ gas after being exposed to a two-stage gas generation protocol comprising a first stage comprising exposure of the chlorite ions to ultraviolet light and a second stage comprising exposure of the chlorite ions to moisture.

102. The composition of aspect 101, wherein the composition generates more $ClO_2$ gas in a two-stage gas generation protocol than the composition generates in a single-stage gas generation protocol.

103. The composition of aspect 101 or aspect 102, wherein the second stage precedes the first stage.

104. The composition of any of aspects 101-103, wherein the composition is substantially free of an energy-activated catalyst comprising a metal oxide and is substantially free of hydronium ions.

105. A composition comprising an inorganic support structure and a plurality of chlorite ions ($ClO_2^-$), wherein the composition is substantially free of an energy-activated catalyst comprising a metal oxide and is substantially free of hydronium ions.

106. The composition of any of aspects 101-105, wherein a chlorite salt is used as a source of the plurality of chlorite ions.

107. The composition of aspect 106, wherein the chlorite salt is selected from the group consisting of sodium chlorite, potassium chlorite, calcium chlorite, magnesium chlorite, lithium chlorite, and ammonium chlorite.

108. The composition of aspect, wherein the chlorite salt is sodium chlorite.

109. The composition of any of aspects 101-108, wherein the inorganic support structure is selected from the group consisting of alumina, silica, zeolite, and clay.

110. The composition of any of aspects 101-109, wherein the composition is placed in a sachet.

It is understood that this invention is not limited to the particular methodology, protocols, materials, and reagents described, as these may vary. It is also to be understood that the terminology used herein is for the purpose of describing particular embodiments only, and is not intended to limit the scope of the present invention.

As used herein and in the appended claims, the singular forms "a," "an," and "the" include plural reference unless the context clearly dictates otherwise. As well, the terms "a" (or "an"), "one or more" and "at least one" can be used interchangeably herein. The terms "comprising," "including," and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes.

The following examples are offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1: 'On-Demand' Release of a Disinfectant Gas: Generation of $ClO_2$ Gas from UV-Activated $NaClO_2$ in the Presence of Humidity In this exemplary embodiment, it is shown that $ClO_2$ can be evolved from solid sodium chlorite ($NaClO_2$) in a two-step process whereby it is first 'activated' by irradiation with UV light under dry condition, and subsequently exposed to moisture to produce $ClO_2$ at a later time-point when it is exposed to moisture. This example includes the systematic investigation of this phenomenon in a continuous gas ($N_2$) flow cell setup under different conditions. Specifically, the examples demonstrate that $NaClO_2$ samples can be activated by UV irradiation under dry condition for subsequent $ClO_2$ release in the presence of moisture. Second, it is demonstrated that the variation in quantity of $ClO_2$ produced as a function of the wavelength of UV irradiation and level of moisture. Third, it is shown that the total $ClO_2$ production from samples can be manipulated by varying the duration of UV exposure. Fourth, the examples describe experiments that were aimed at testing the longevity of activation of samples before they were exposed to moisture. Finally, the examples show a systematic investigation of the effect of the initial moisture content of $NaClO_2$ on $ClO_2$ production from activated samples.

Fabrication of Gas Flow Cell.

Figure 3A:
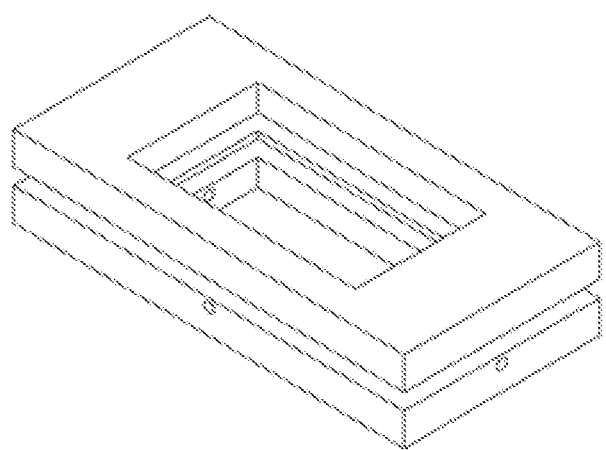
FIG. 3A is a 3D representation of gas flow cell.
Figure 3B:
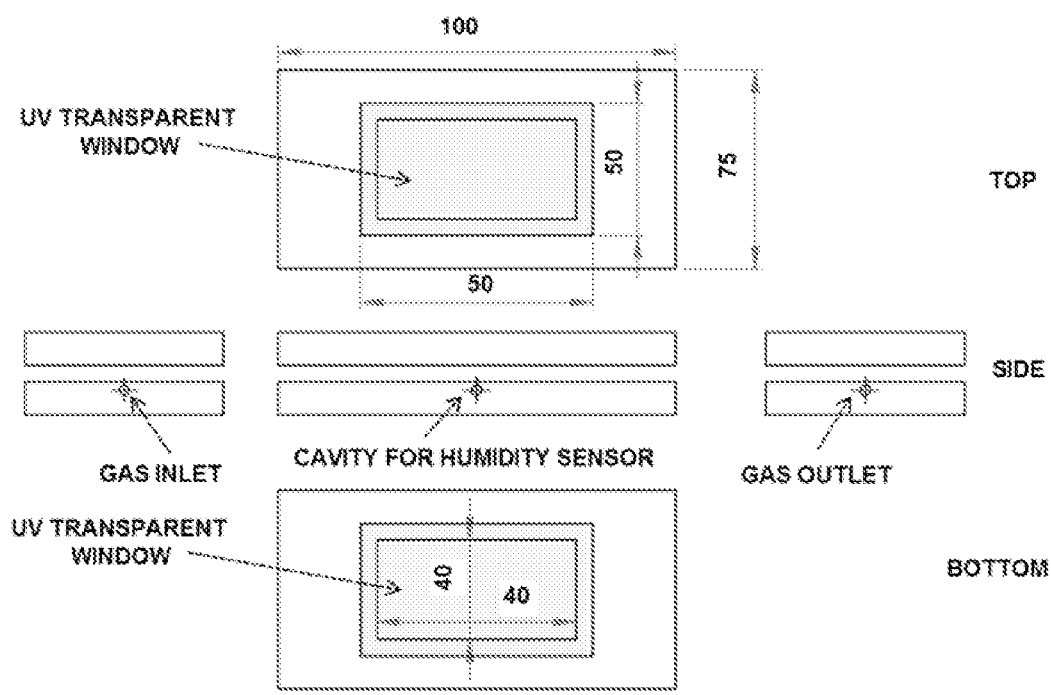
FIG. 3B includes a top, side and bottom view showing the dimensions of the gas flow cell shown in FIG. 3A (scale in mm).

A gas flow cell (internal volume: 4 cm×4 cm×1 cm=16 $cm^3$) was fabricated from stainless steel with 3 small openings (radius: 2 mm) and 2 window openings (5 cm×5 cm=25 $cm^2$, see FIGS. 3A and 3B). Two of the small openings were fitted with stainless steel tubing along with open/shut valves (Swagelok) and acted as gas inlet and outlet respectively. The third small opening was fitted with a humidity sensor (Honeywell, #HIH-4602-C). The two window openings were fitted with UV-transparent windows made of fused silica (Edmund Optics). The flow cell was also equipped with a rubber gasket to make the setup air tight.

Gas flow cell experiments. Most of the experiments were done with a stream of $N_2$ gas (Industrial grade, AirGas) flowing through the gas flow cell at a flow rate of 1000 $cm^3$/min. The gas inlet was either (i) directly connected to a $N_2$ gas cylinder (dry gas flow condition) or (ii) to a dew point generator (LI-610, LI-COR Inc.) that was connected to a $N_2$ gas cylinder (moist gas flow condition). The moisture content of the $N_2$ gas flowing into the cell was adjusted to 15/30/45/60/75% Relative Humidity (RH) for different experiments using the dew point generator. The outlet of the gas flow cell was connected to a $ClO_2$ detector (GasAlert Extreme, Honeywell) with the help of a fixture provided with the detector that ensured the outgoing stream was in proximal contact with the sensor. For each experiment, fresh samples of $NaClO_2$ (100 mg, high purity grade, VWR International) were spread in a thin layer (radius: 1 cm) on a small plastic boat on top of the bottom window inside the gas flow cell (see FIGS. 3A and 3B) before sealing it shut.

Samples inside the gas flow cell were 'activated' by exposure to ultraviolet (UV) light through the UV-transparent windows on top of the cell. UV light of 3 different wavelengths was used to illuminate the sample: (i) 254 nm (short-wave, UV-C), (ii) 312 nm (medium-wave, UV-B) and (iii) 365 nm (long-wave, UV-A). UV light was generated using UV-lamps (Spectroline, #EN-280L (UV—365 nm), #EBF-280C (UV—312/254 nm)) which were placed over the gas flow cell at a distance of 6 cm from the sample (irradiance at sample 1-1.5 $mW/cm^{2t}$ discussed below). Moist $N_2$ gas was blown over activated/non-activated (control) samples, and $ClO_2$ produced during any time was detected by the $ClO_2$ detector, which logged the data in its internal memory at a frequency of one data point every 5 seconds. The data was transferred to a computer using a data transfer accessory for further analysis.

The total $ClO_2$ produced in any experiment was calculated with the help of area under curve (AUC) of the release profile which was evaluated as:

$$\text{Total } ClO_2 (\text{in } \mu g) = K(\int y \partial t) \approx K(\Sigma y \Delta t),$$

Where, y=detector reading (in ppm), $\Delta t = 1/12$ min, K=unit conversion constant=2.97 μg/(ppm-min) for 1000 (cc/min) flow, and =0.7425 μg/(ppm-min) for 250 (cc/min) flow.

Under the above general scheme, the production of $ClO_2$ from UV-activated $NaClO_2$ samples was investigated under different conditions, such as varying humidity, varying UV activation wavelength, varying delay between activation of samples and exposure to moisture and varying the initial moisture content of samples. All experiments were repeated at least three times. Table 1 summarizes the different kinds of experiments performed.

TABLE 1

Summary of gas flow cell experiments where release of $ClO_2$ was investigated under varying conditions.

| Step# | Duration (min) | $N_2$ flow - dry/moist | UV light (on/off) | Remarks |
|---|---|---|---|---|
| | | Experiments in which humidity was varied | | |
| 1 preparation | 15 | Dry (1000 cm³/min) | Off | Removal of residual moisture/gases from system |
| 2 activation | 15 | Dry (1000 cm³/min) | On (UV-A, UV-B, or UV-C) | UV-activation |
| 3 delay | 15 | Dry (1000 cm³/min) | Off | Time gap between activation and $ClO_2$ release |
| 4 release | 15 | Moist (15, 30, 45, 60 or 75% RH) (1000 cm³/min) | Off | Release of $ClO_2$ |
| | | Experiments in which duration of UV exposure was varied | | |
| 1 preparation | 15 | Dry (1000 cm³/min) | Off | Removal of residual moisture/gases from system |
| 2 activation | 0, 1, 2, 3, 5, 8, 10, 12 or 15 | Dry (1000 cm³/min) | On (UV-C) | UV-activation |
| 3 delay | 15 | Dry (1000 cm³/min) | Off | Time gap between activation and $ClO_2$ release |
| 4 release | 15 | Moist (60% RH) (1000 cm³/min) | Off | Release of $ClO_2$ |
| | | Experiments in which delay between UV-activation and release of $ClO_2$ was varied | | |
| 1 preparation | 15 | Dry (1000 cm³/min) | Off | Removal of residual moisture/gases from system |
| 2 activation | 15 | Dry (1000 cm³/min) | On (UV-C) | UV-activation |
| 3 delay | 15 | Dry (1000 cm³/min) | Off | Time gap between activation and $ClO_2$ release |
| 4 additional delay | 0, 60, 180, 360, 540, 900, 1440, or 2880 | No flow. Closed Chamber (containing $N_2$) | Off | Sample stored under stationary $N_2$ to test for lifetime of activated samples |
| 5 release | 15 | Moist (60% RH) (1000 cm³/min) | Off | Release of $ClO_2$ |
| | | Experiments in which the effect of initial moisture content of $NaClO_2$ samples on the amount of $ClO_2$ released was investigated | | |
| 1 preparation | 60 | Moist (0, 15, 30, 45, 60 or 75% RH) (250 cm³/min) | Off | Equilibrating the salt with moist $N_2$ flow |
| 2 activation | 20 seconds | Dry (1000 cm³/min) | Off | Eliminating the headspace moisture |
| 3 delay | 15 | No flow. Closed Chamber (containing $N_2$) | On (UV-C) | UV-activation |
| 4 release | 15 | Dry (250 cm³/min) | Off | Release of $ClO_2$ |

The moisture content of the stock $NaClO_2$ used in the experiments was measured using Karl Fischer titration and found to be 0.209±0.007 weight % (N=4). The UV intensity at a distance of 6 cm from the different lamps were also measured using a radiometer (UV Power Puck® II, EIT Inc., N=3) and were found to be 1.15 mW/cm² (UV—254 nm), 1.43 mW/cm² (UV—312 nm) and 1.01 mW/cm² (UV—365 nm), respectively.

The general design of most of the experiments can be divided into 4 steps—(1) preparation (2) activation (3) delay and (4) release. Continuous flow of $N_2$ gas (dry/moist, fixed flow rate: 1000 cc/min) was maintained from one end into the gas flow cell and the other end was attached to the $ClO_2$ detector which monitored the $ClO_2$ concentration in the outgoing gas stream. During the preparation step, dry $N_2$ gas was flowed through the gas flow cell containing the fresh $NaClO_2$ sample for 15 min to clear the gas flow cell of any residual moisture or gas that may have collected during or between separate experiments. During the activation step, samples were exposed to UV light for 15 min (unless otherwise mentioned). During the delay step, samples were kept in darkness under dry $N_2$ for 15 min (unless otherwise mentioned). This ensured a time-gap between activation of the samples and exposure to humidity and tested the durability of UV-activation. During the release step, samples were exposed to a flow of moist $N_2$.

Figure 4A:
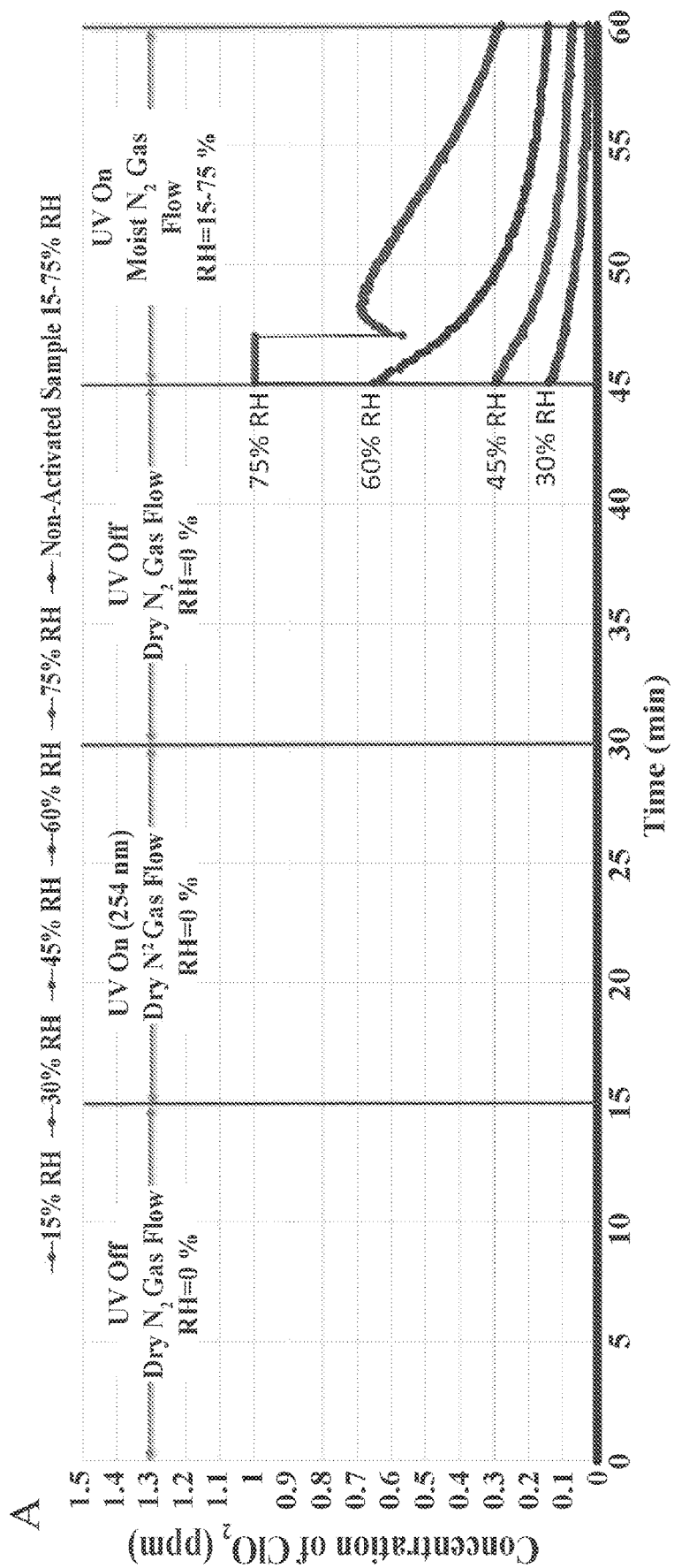
FIG. 4A shows averaged concentration of $ClO_2$ released from $NaClO_2$ activated with UV (254 nm) light in experiments where exposure to moisture is varied (N=3).

FIG. 4A shows the averaged $ClO_2$ concentration recorded by the detector for samples activated with UV light (254 nm) and exposed subsequently to varying levels of moisture. Firstly, no $ClO_2$ was detected in control samples (no UV light during activation step in the experiments). However, in samples that were exposed to UV light during the activation step, $ClO_2$ production was recorded only when the samples were exposed to moisture during the release step.

Secondly, the concentration of $ClO_2$ detected varied directly as the relative humidity of the flowing $N_2$ gas which was varied between 15-75% in increments of 15%. While no $ClO_2$ was detected at 15% RH, $ClO_2$ concentration ranging from (i) 0.01-0.13 ppm was detected at 30% RH (ii) 0.08-0.3 ppm was detected with 45% RH (iii) 0.15-0.65 ppm was detected at 60% RH and (iv) 0.28-1 ppm was detected at 75% RH. Note that at 75% RH, the concentration of $ClO_2$ was consistently measured to be constant at one ppm for about 2 minutes, after which it started to decrease (the $ClO_2$ detector can only measure $ClO_2$ concentrations between 0 and 1 ppm). Therefore, the reported average mass of $ClO_2$ that is released at 75% RH should be considered as an underestimate for the real mass of $ClO_2$ released at 75% RH. Also note that at relative humidity higher than 75%, there appears to be a burst release of $ClO_2$ from the samples which results in saturation of detector for the whole release period, therefore the observations are limited to 15-75% RH.

Figure 4B:
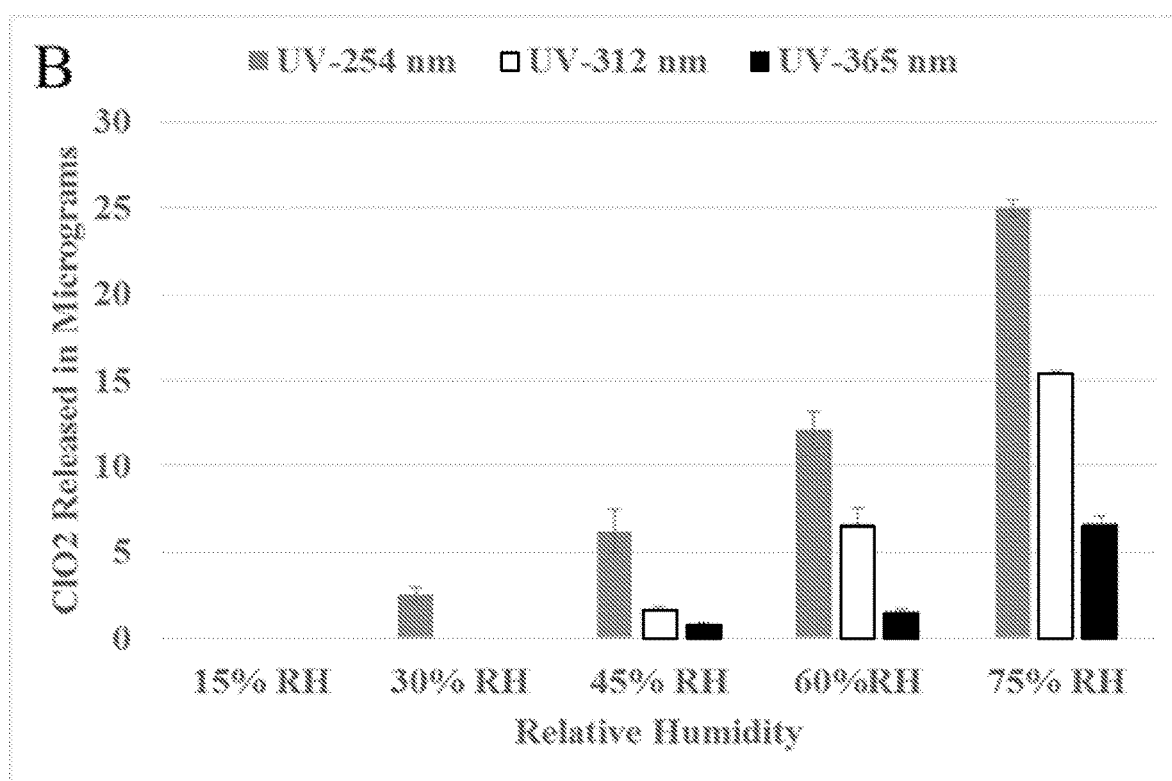
FIG. 4B shows average mass of $ClO_2$ released in experiments from $NaClO_2$ samples activated at 3 different wavelengths and exposed to different moisture levels (N=3).
Figure 5A:
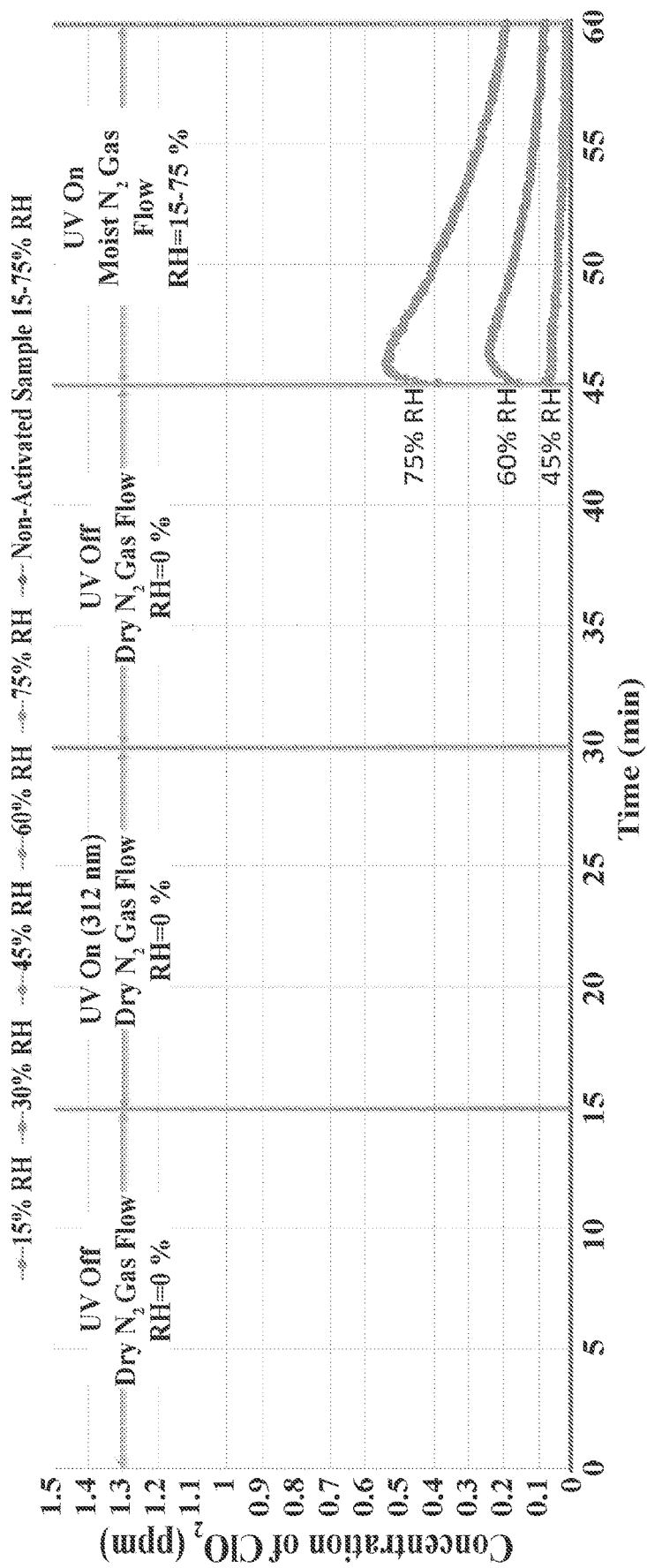
FIGS. 5A and 5B show averaged concentration of $ClO_2$ released from $NaClO_2$ activated with UV light of different wavelengths.
Figure 5B:
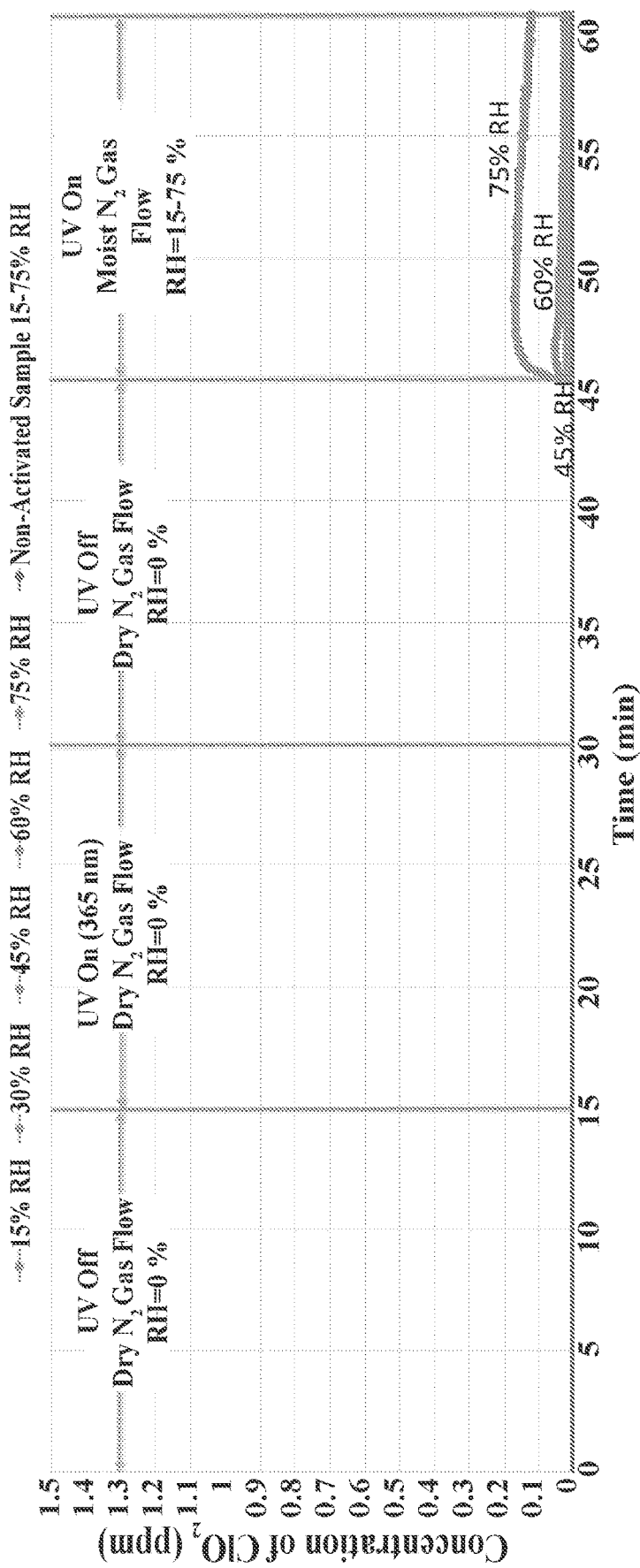

Overall, FIG. 4A demonstrates the principal concept of the study: that $NaClO_2$ samples can be photochemically activated and produce $ClO_2$ subsequently when exposed to moisture. Similar experiments where moisture content of the flowing $N_2$ was varied (RH 15-75%) were also conducted with samples that were activated at longer UV wavelengths (UV—312 nm, UV—365 nm, the detailed release profiles are shown in FIGS. 5A and 5B). FIG. 4B summarizes the total $ClO_2$ produced in 15 min during the release step from samples activated at different UV wavelengths and exposed to different RH. FIG. 4B demonstrates that the extent of UV-activation decreases at higher wavelengths of UV. The minimum RH at which detectable levels of $ClO_2$ (>0.01 ppm) is produced with different wavelengths of UV-activation is 30% for 254 nm, 45% for 312 nm and 45% for 365 nm. Moreover, the total $ClO_2$ produced varies from (~2-25 µg) (30-75% RH) for 254 nm, (~1.5-15 µg) (45-75% RH) for 312 nm and (~0.9-7 µg) (45-75% RH) for 365 nm. These results are consistent with the UV absorbance of $NaClO_2$.

Figure 4C:
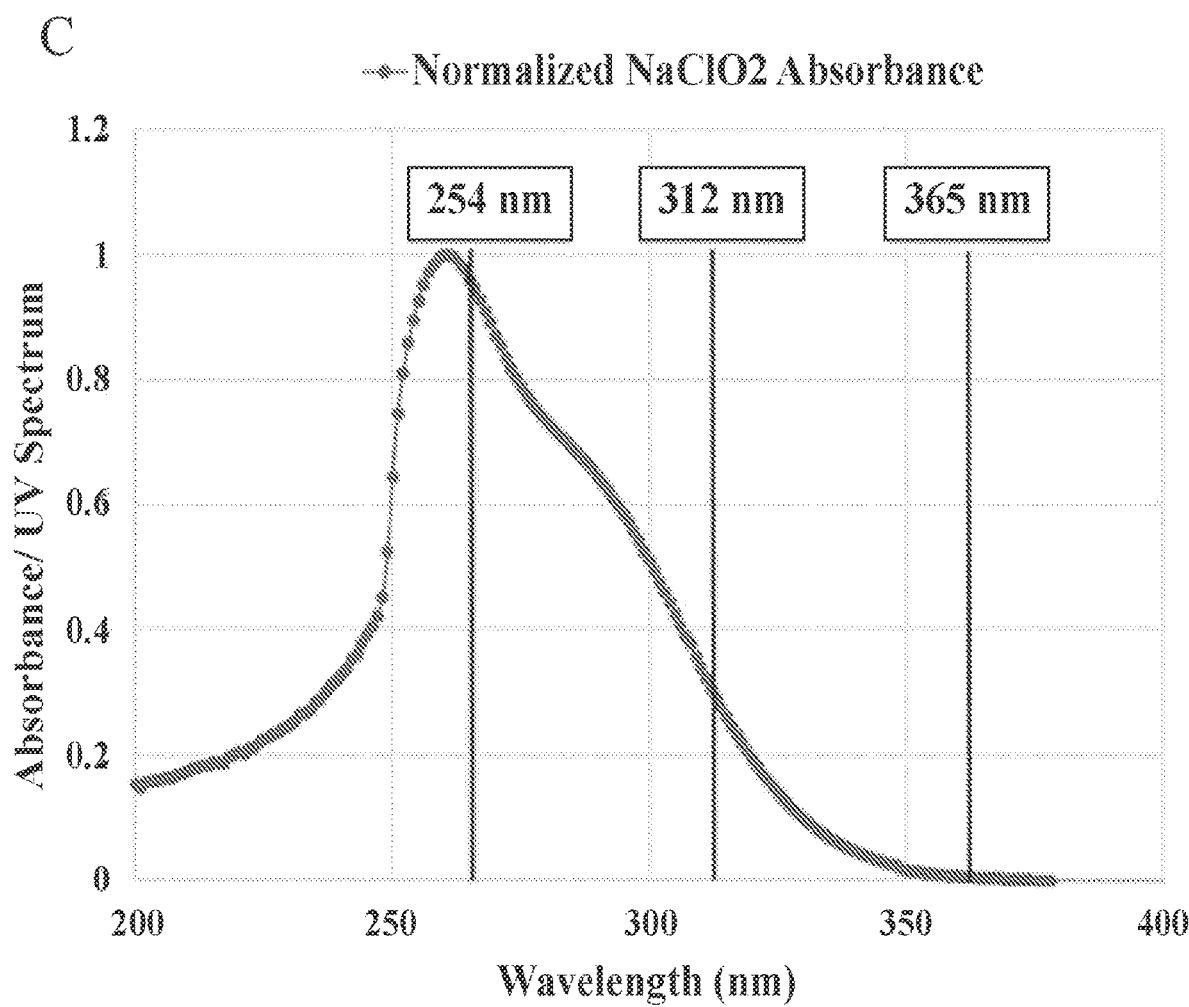
FIG. 4C shows comparison of UV absorbance of $NaClO_2$ sample (aq.) UV spectrum of different UV lamps (data provided by manufacturer).

FIG. 4C shows the absorption spectrum of $NaClO_2$ (2 mgrs./ml aqueous solution) along with the peak UV wavelengths of the UV light sources used to illuminate the samples. FIG. 4C suggests that UV-254 nm will have the highest spectral overlap with $NaClO_2$ absorbance and their peaks are nearly coincident. On the other hand, UV-312 nm has spectral overlap with a shoulder of the $NaClO_2$ absorbance and UV-365 nm has the least overlap with its peak wavelength almost outside of the $NaClO_2$ absorbance spectrum (note that the UV light used to illuminate the samples is not monochromatic and likely has a spectral spread. Information provided by the manufacturer of the lamps indicated that the likely limits of the spectra spread for UV-365 nm is 320-400 nm, UV-312 nm is 280-320 nm, and UV-254 nm is 240-280 nm, in the absence of more detailed information, the probable peak positions of the emission spectra of each lamp is shown in FIG. 4C).

Overall, the key result that emerges is that the total production of $ClO_2$ from activated samples can be tuned by nearly one order of magnitude (~0.9 µg to 25 µg) in the experiments by varying both UV wavelength and humidity. However, note that the total $ClO_2$ potentially available for release in the system is ~60 mg which is >1000 times higher than the total release observed in 15 min (This observation implies that only a thin top layer of the $NaClO_2$ samples has been activated).

Figure 6:
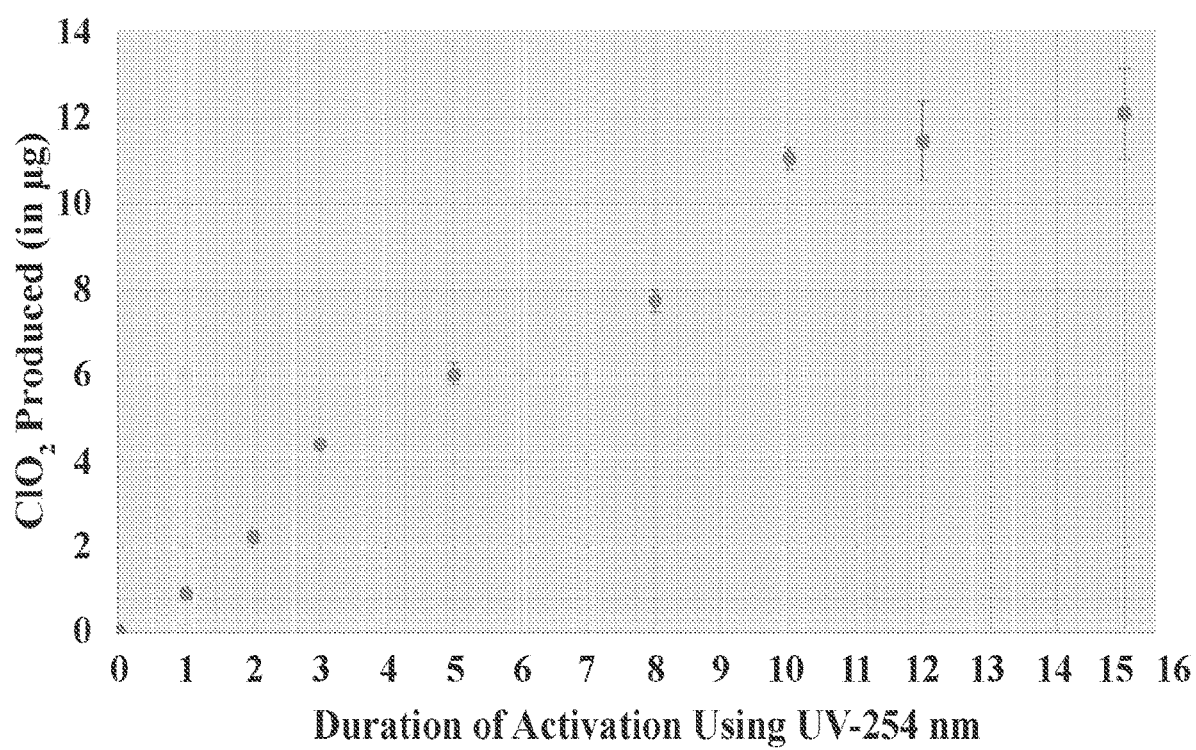
FIG. 6 shows total $ClO_2$ released in 15 min from $NaClO_2$ samples at 60% RH that were activated with UV light (254 nm) for different times (0-15 min). N=3.

Experiments to investigate the effect of duration of UV exposure (λ: 254 nm) to $NaClO_2$ samples (see Table 1 for experimental scheme) were also completed. FIG. 6 shows the total mass of $ClO_2$ that is produced from $NaClO_2$ samples in 15 min (during release step) that were irradiated with UV light for different durations. While no release of $ClO_2$ could be detected from non-activated samples, a small mass was released from samples illuminated for 1 min and the amount of $ClO_2$ released increased by increasing the UV-irradiation times up to 10 min. Note that the release profile shows a sigmoidal behavior and the exposure to UV-irradiation for times longer than 10 minutes will not result in further production of $ClO_2$.

Figure 7A:
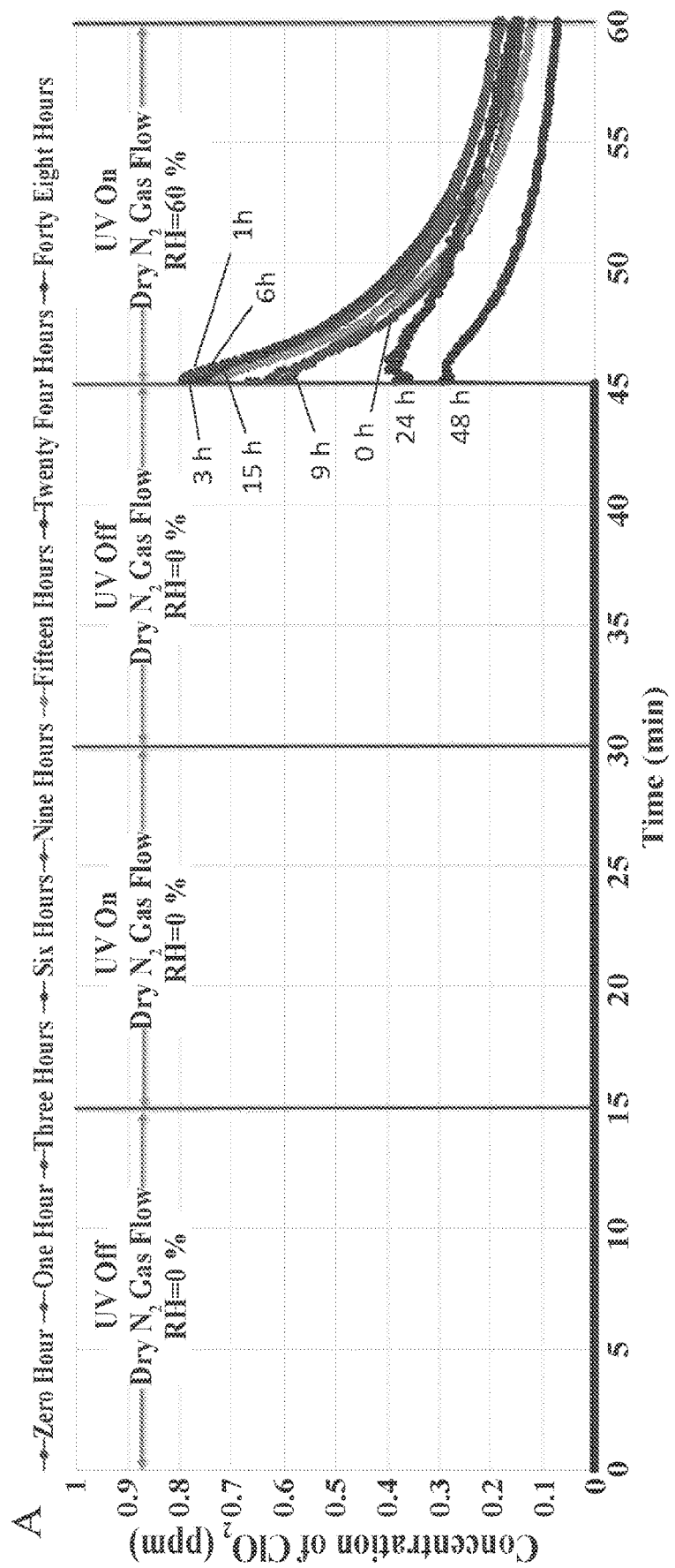
FIG. 7A shows averaged concentration of $ClO_2$ released in 15 min at 60% RH from activated $NaClO_2$ samples (254 nm) that were stored for different times before exposure to moisture (60% RH).
Figure 7B:
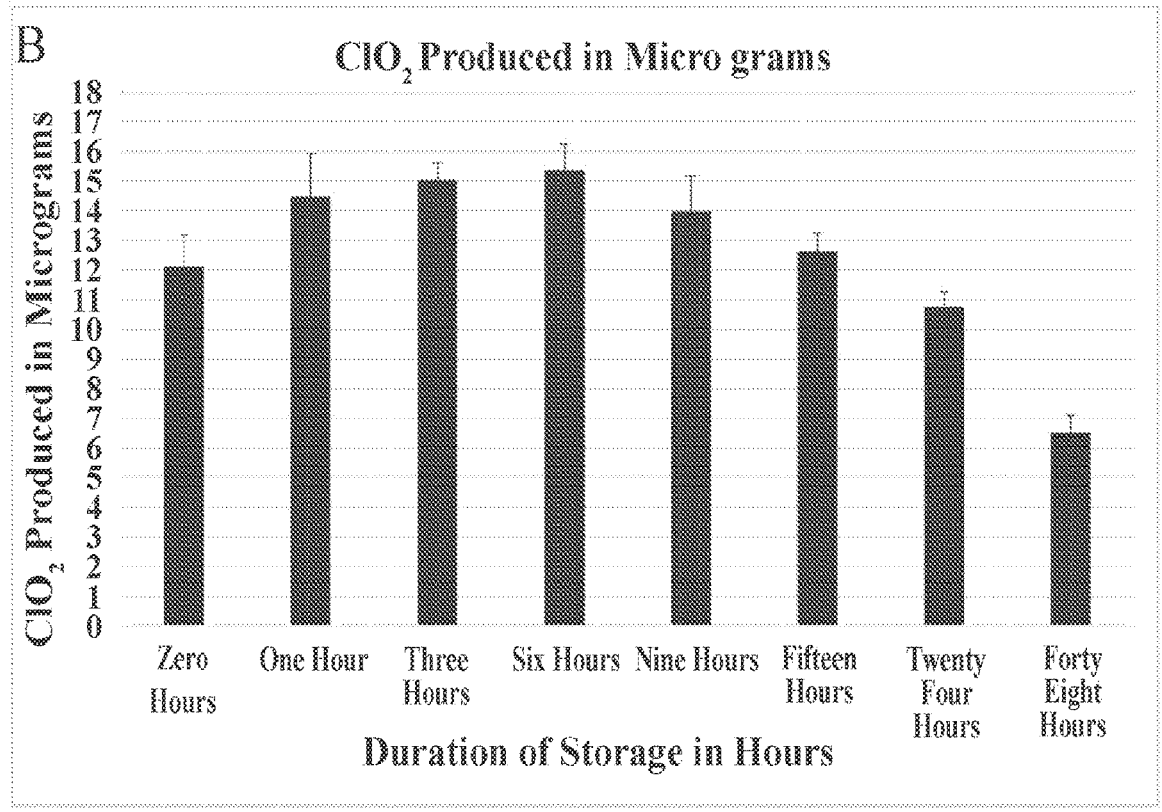
FIG. 7B shows total mass of $ClO_2$ released from stored samples (N=3).

Experiments to test the lifetime of the activated state of $NaClO_2$ (see Table 1 for experimental scheme) were also completed. In these experiments, samples were activated with UV light (duration 15 min, λ: 254 nm) and were stored in $N_2$ gas for an additional duration of 1-48 hour between the 'delay' and 'release' step (exposure to 60% RH). FIG. 7A shows the total mass of $ClO_2$ released from these samples. First, note that activated samples could release $ClO_2$ even after 48 hours, albeit in lesser quantities. Further inspection of FIGS. 7A and 7B demonstrate that the activated $NaClO_2$ samples can maintain the same activity level for about fifteen hours and a meaningful decrease in the activity of $NaClO_2$ samples starts after twenty four hours. The above mentioned results are consistent with the hypothesis that a highly stable active intermediate has been formed as the result of UV-irradiation which subsequently reacts with water upon exposure to moist $N_2$ flow. The identity of this active intermediate and the mechanism through which it reacts with water to produce $ClO_2$ in not clear for us at the moment and understanding these issues is beyond the scope of this example.

Figure 8:
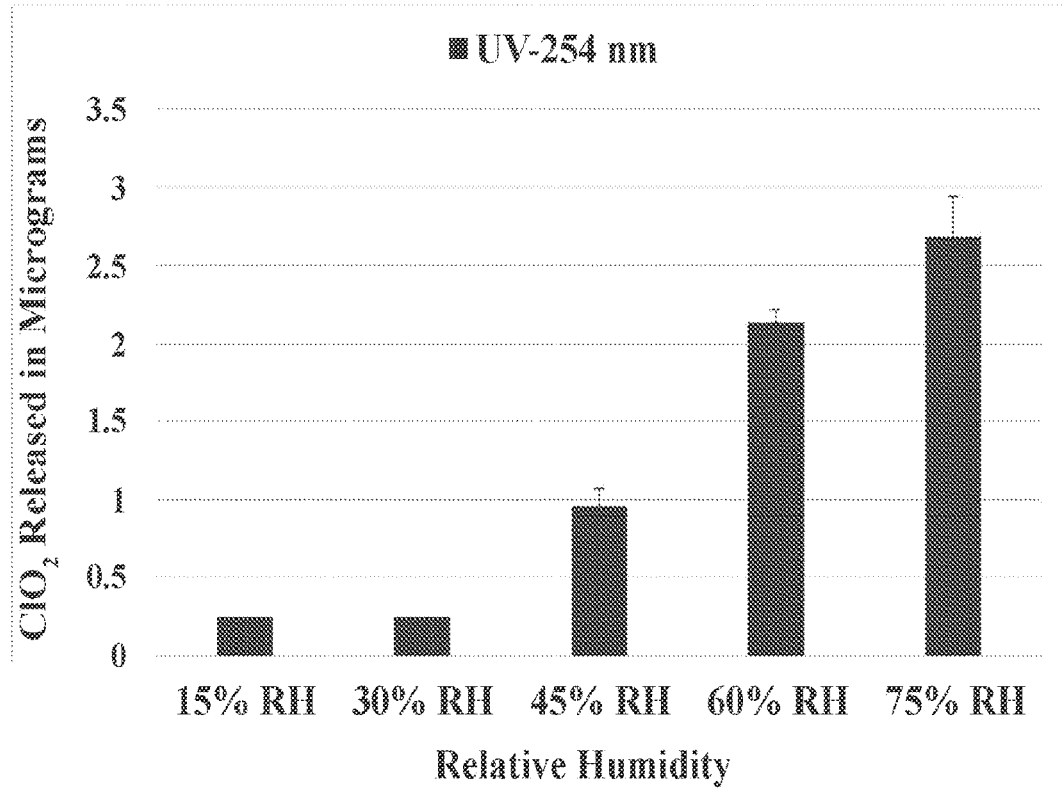
FIG. 8 shows the total mass of $ClO_2$ released in 15 min from activated $NaClO_2$ samples that were equilibrated with $N_2$ flow for one hour (RH=0, 15, 30, 45, 60, 75%) and were activated subsequently with 254 nm UV for 15 minutes. The release of $ClO_2$ was performed in dry $N_2$ flow (headspace moisture was eliminated by flowing dry $N_2$ (1000 cc/min) for 20 seconds before UV activation) (N=3).
Figure 9:
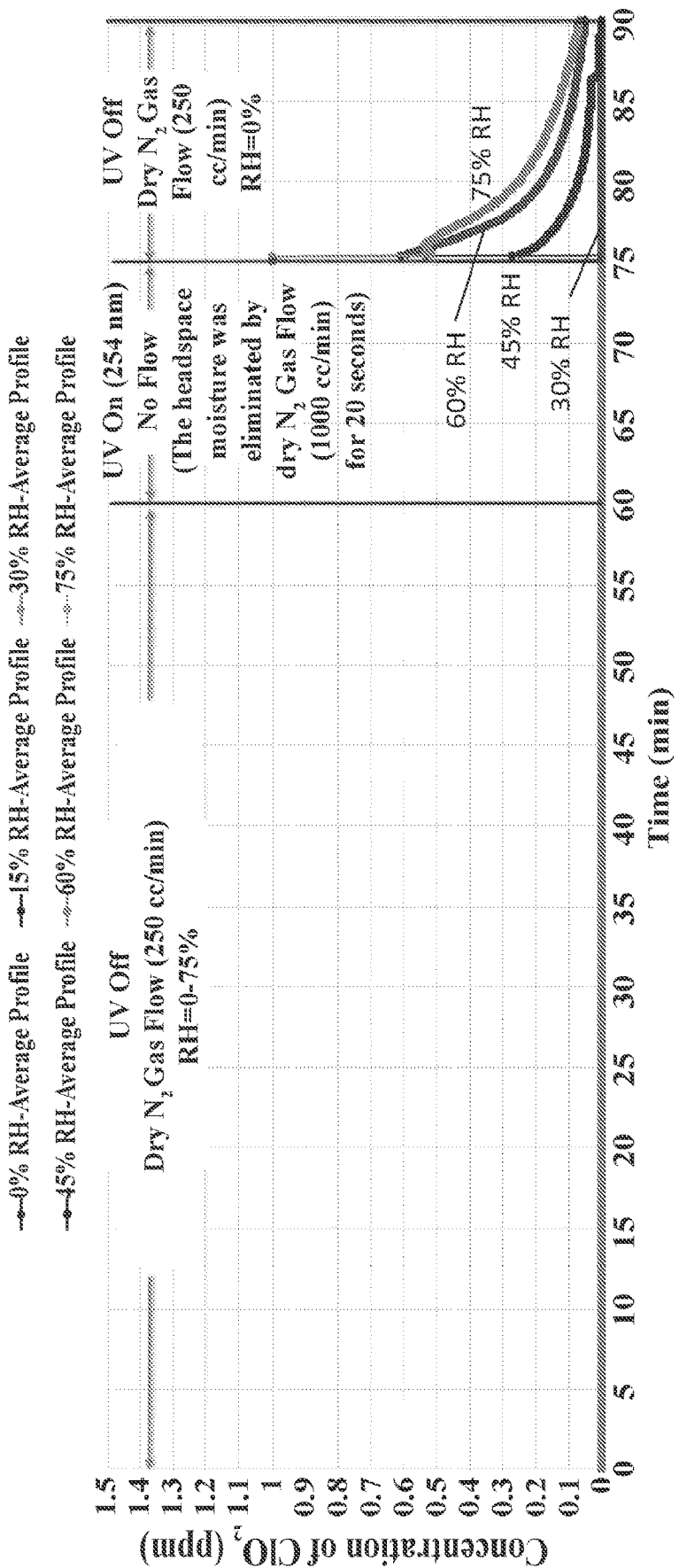
FIG. 9 shows averaged concentration of $ClO_2$ released in 15 min from activated $NaClO_2$ samples that were equilibrated with $N_2$ flow for one hour (RH=0, 15, 30, 45, 60, 75%) and were activated subsequently with 254 nm UV for 15 minutes. The release of $ClO_2$ was performed in dry $N_2$ flow (headspace moisture was eliminated by flowing dry $N_2$ (1000 cc/min) for 20 seconds before UV activation) (N=3).

Finally, experiments were conducted where $NaClO_2$ samples were equilibrated with moist $N_2$ flow for one hour (RH=0, 15, 30, 45, 60, 75%) and were activated subsequently with 254 nm UV (see Table 1 for experimental scheme). The release of $ClO_2$ was performed in dry $N_2$ flow (head space moisture was eliminated before activation, the total amount of $ClO_2$ released is reported in FIG. 8 and the average concentration profiles are reported in FIG. 9. FIG. 8 shows that the initial moisture content of $NaClO_2$ samples affects the $ClO_2$ release from activated samples (i.e. $ClO_2$ release from activated samples increases with increasing the initial moisture content of $NaClO_2$). However, the amount of $ClO_2$ released is much lower in comparison with the experiments at which the humid air was used to generate $ClO_2$ (FIGS. 4A-B).

The key result from this example is that the release of $ClO_2$ can be triggered from solid $NaClO_2$ by photoactivating it with UV light (200-400 nm) and subsequently exposing it to moisture. The quantity of $ClO_2$ released can be tuned ~25 fold by varying various conditions such as wavelength of UV-irradiation, relative humidity, and duration of UV exposure. Activated samples can retain their activity at least up to 48 hours. Overall, the results of this study introduce a novel stimuli-responsive process using which $ClO_2$ can be evolved directly from the solid phase ($NaClO_2$ samples) in a highly controlled manner using only simple external triggers such as UV light and moisture. This process could be incorporated into various applications where $ClO_2$ gas can be safely evolved in small quantities that are non-toxic to humans but act as a potent disinfectant and/or deodorant.

Example 2: 'On-Demand' Release of a Disinfectant Gas: Generation of $ClO_2$ Gas from UV-Activated Polymeric Films Containing $NaClO_2$ In this example, it is demonstrated that controlled release of $ClO_2$ gas from chlorite-containing polymeric films. This results show that polymeric thin films incorporating chlorite ions can be used for the controlled release of $ClO_2$. Accordingly, polymeric thin films incorporating chlorite ions can be used to wrap or package products that would benefit from on-demand disinfection and/or deodorizing, including without limitation, medical devices or food products.

Film Preparation.

Polyvinyl alcohol (PVA) polymer (Molecular weight=13000-23000 gr/mole, Sigma Aldrich, 98% hydrolyzed) and sodium chlorite ($NaClO_2$) salt (high purity grade, VWR International) were dissolved in deionized water to achieve a ((0.05 gr PVA-0.05 gr $NaClO_2$)/1 mL solution). Fused silica substrates (cut into (2 cm×2.5 cm) pieces) were cleaned by water, ethanol, and water and then they were dried by nitrogen gas ($N_2$) before use. 500 microliter of the (PVA-$NaClO_2$) solution was spin coated on a piece of fused silica (3000 rounds per minute (rpm) for 1 min). The spin coated film was then dried for 30 minutes at T=70° C. inside a temperature controlled oven. The above prepared films have a nominal (50 wt. % PVA-50 wt. % $NaClO_2$) composition.

Other film compositions were achieved by keeping the polymer concentration in solution constant and adjusting the salt concentration in the solution. Table 2 summarizes the details of the preparation of solutions.

For each experiment, fresh samples of polyvinyl alcohol (PVA) films that were formed on fused silica substrate (nominal $NaClO_2$ compositions within the film varies between (10 wt. %-50 wt. %)) were placed on top of the bottom window inside the gas flow cell before sealing it shut. Samples inside the gas flow cell were 'activated' by exposure to ultraviolet (UV) light through the UV-transparent windows on top of the cell (the wavelength of UV is 254 nm (short-wave, UV-C))). Moist $N_2$ gas was blown over activated/non-activated (control) films, and $ClO_2$ produced during any time was detected by the $ClO_2$ detector which logged the data in its internal memory at a frequency of one data point every 5 seconds. The data was transferred to a computer using a data transfer accessory for further analysis. The total $ClO_2$ produced in any experiment was calculated

TABLE 2

Summary of solutions used to prepare films with different compositions.

| PVA solution concentration | $NaClO_2$ solution concentration | Details | Expected composition of the spin coated film |
|---|---|---|---|
| 0.1 gram polymer/1 mL of deionized water | 0.1 gram salt/1 ml of deionized water | 250 microliter of the PVA solution is mixed with 250 microliter of the $NaClO_2$ salt solution. This solution is used for spin coating. | 50 wt. % PVA-50 wt. % $NaClO_2$ salt |
| 0.1 gram polymer/1 mL of deionized water | 0.067 gram salt/1 ml of deionized water | 250 microliter of the PVA solution is mixed with 250 microliter of the $NaClO_2$ salt solution. This solution is used for spin coating. | 60 wt. % PVA-40 wt. % $NaClO_2$ salt |
| 0.1 gram polymer/1 mL of deionized water | 0.043 gram salt/1 ml of deionized water | 250 microliter of the PVA solution is mixed with 250 microliter of the $NaClO_2$ salt solution. This solution is used for spin coating. | 70 wt. % PVA-30 wt. % $NaClO_2$ salt |
| 0.1 gram polymer/1 mL of deionized water | 0.025 gram salt/1 ml of deionized water | 250 microliter of the PVA solution is mixed with 250 microliter of the $NaClO_2$ salt solution. This solution is used for spin coating. | 80 wt. % PVA-20 wt. % $NaClO_2$ salt |
| 0.1 gram polymer/1 mL of deionized water | 0.011 gram salt/1 ml of deionized water | 250 microliter of the PVA solution is mixed with 250 microliter of the $NaClO_2$ salt solution. This solution is used for spin coating. | 90 wt. % PVA-10 wt. % $NaClO_2$ salt |

Gas Flow Cell Experiments.

Experiments were performed with a stream of $N_2$ gas (Industrial grade, AirGas) flowing through the gas flow cell at a flow rate of 1000 $cm^3$/min. The gas inlet was either (i) directly connected to a $N_2$ gas cylinder (dry gas flow condition) or (ii) to a dew point generator (LI-610, LI-COR Inc.) that was connected to a $N_2$ gas cylinder (moist gas flow condition). The moisture content of the $N_2$ gas flowing into the cell was adjusted to 60% Relative Humidity (RH) for different experiments using the dew point generator. The outlet of the gas flow cell was connected to a $ClO_2$ detector (GasAlert Extreme, Honeywell) with the help of a fixture provided with the detector that ensured the outgoing stream was in proximal contact with the sensor.

with the help of area under curve (AUC) of the release profile which was evaluated as:

$$\text{Total } ClO_2 (\text{in } \mu g) = K(\int y \partial t) \approx K(\Sigma y \Delta t),$$

Where, y=detector reading (in ppm), $\Delta t = 1/12$ min, K=unit conversion constant=2.97 μg/(ppm-min) for 1000 (cc/min) flow, and =0.7425 μg/(ppm-min) for 250 (cc/min) flow.

Under the above general scheme, the production of $ClO_2$ from UV-activated polyvinyl alcohol (PVA) films that were formulated to contain $NaClO_2$ samples was investigated under different conditions such as varying film composition and varying UV exposure duration. All experiments were repeated at least three times. Table 3 summarizes the different kinds of experiments performed.

TABLE 3

Summary of gas flow cell experiments where release of $ClO_2$ from thin films was investigated under varying conditions.

| Step# | Duration (min) | $N_2$ flow - dry/moist | UV light (on/off) | Remarks |
|---|---|---|---|---|
| Experiments in which film composition was varied (the same procedure is used when the films were reactivated). | | | | |
| 1 preparation | 15 | Dry (1000 $cm^3$/min) | Off | Removal of residual moisture/gases from system |
| 2 activation | 15 | Dry (1000 $cm^3$/min) | On (UV-Wavelength = 254 nm) | UV-activation |
| 3 delay | 15 | Dry (1000 $cm^3$/min) | Off | Time gap between activation and $ClO_2$ release |

TABLE 3-continued

Summary of gas flow cell experiments where release of $ClO_2$ from thin films was investigated under varying conditions.

| Step# | Duration (min) | $N_2$ flow - dry/moist | UV light (on/off) | Remarks |
|---|---|---|---|---|
| 4 release | 15 | Moist (60% RH) (1000 cm³/min) | Off | Release of $ClO_2$ |
| Experiments in which duration of UV exposure was varied | | | | |
| 1 preparation | 15 | Dry (1000 cm³/min) | Off | Removal of residual moisture/gases from system |
| 2 activation | 15/30/60/120 | Dry (1000 cm³/min) | On (UV-Wavelength = 254 nm) | UV-activation |
| 3 delay | 15 | Dry (1000 cm³/min) | Off | Time gap between activation and $ClO_2$ release |
| 4 release | 15 | Moist (60% RH) (1000 cm³/min) | Off | Release of $ClO_2$ |

Choice of Substrate for Thin Film Experiments.

Figure 10:
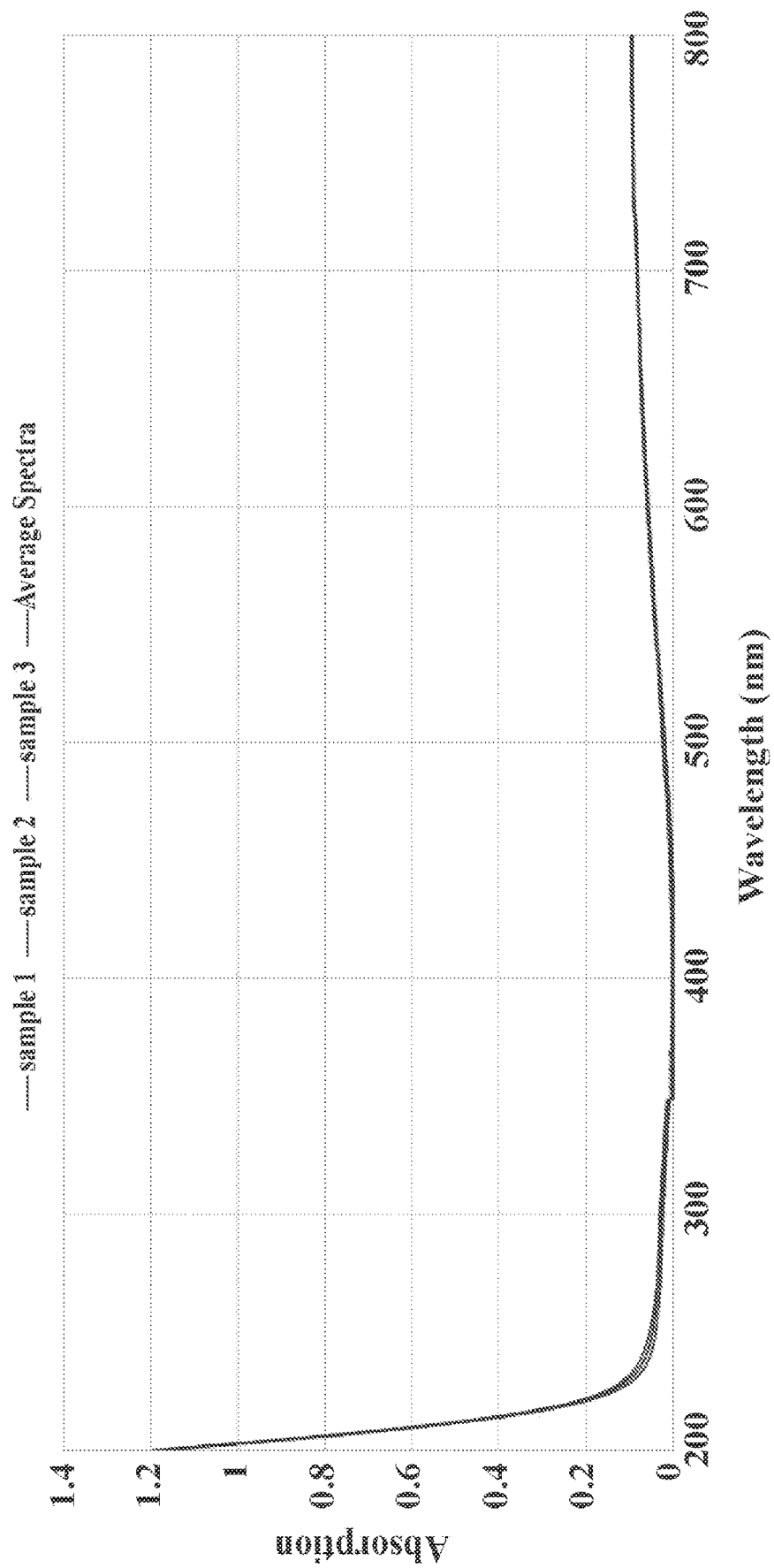
FIG. 10 shows the UV-Visible spectrum of fused silica (without any thin film formed on it). N=3.

Fused silica substrates were used for the thin film experiments. The UV-Visible spectrum of fused silica confirms that the absorption of this substrate is below 0.2 for all wavelengths ≥220 nm and therefore this substrate is mostly UV transparent (FIG. 10). The reaction chamber windows are also made of fused silica substrate.

Activation and Reactivation Experiments for Thin Films with Different Compositions.

Thin polymeric films were formed with different nominal sodium chlorite concentrations (i.e. (50 wt. % $NaClO_2$-50 wt. % PVA)-(40 wt. % $NaClO_2$-60 wt. % PVA)-(30 wt. % $NaClO_2$-70 wt. % PVA)-(20 wt. % $NaClO_2$-80 wt. % PVA)-(10 wt. % $NaClO_2$-90 wt. % PVA)). Each experiment had 4 steps (1) preparation (2) activation (3) delay and (4) release. Continuous flow of $N_2$ gas (dry/moist, fixed flow rate: 1000 cc/min) was maintained from one end into the gas flow cell and the other end was attached to the $ClO_2$ detector which monitored the $ClO_2$ concentration in the outgoing gas stream. During the preparation step, dry $N_2$ gas was flowed through the gas flow cell containing the fresh sample for 15 min to clear the gas flow cell of any residual moisture or gas that may have collected during or between separate experiments. During the activation step, thin films were exposed to UV light (wavelength=254 nm) for 15 min. During the delay step, thin films were kept in darkness under dry $N_2$ for 15 min. This ensured a time-gap between activation of the samples and exposure to humidity and tested the durability of UV-activation. During the release step, thin films were exposed to a flow of moist $N_2$ (Relative humidity=60%).

Figure 11A:
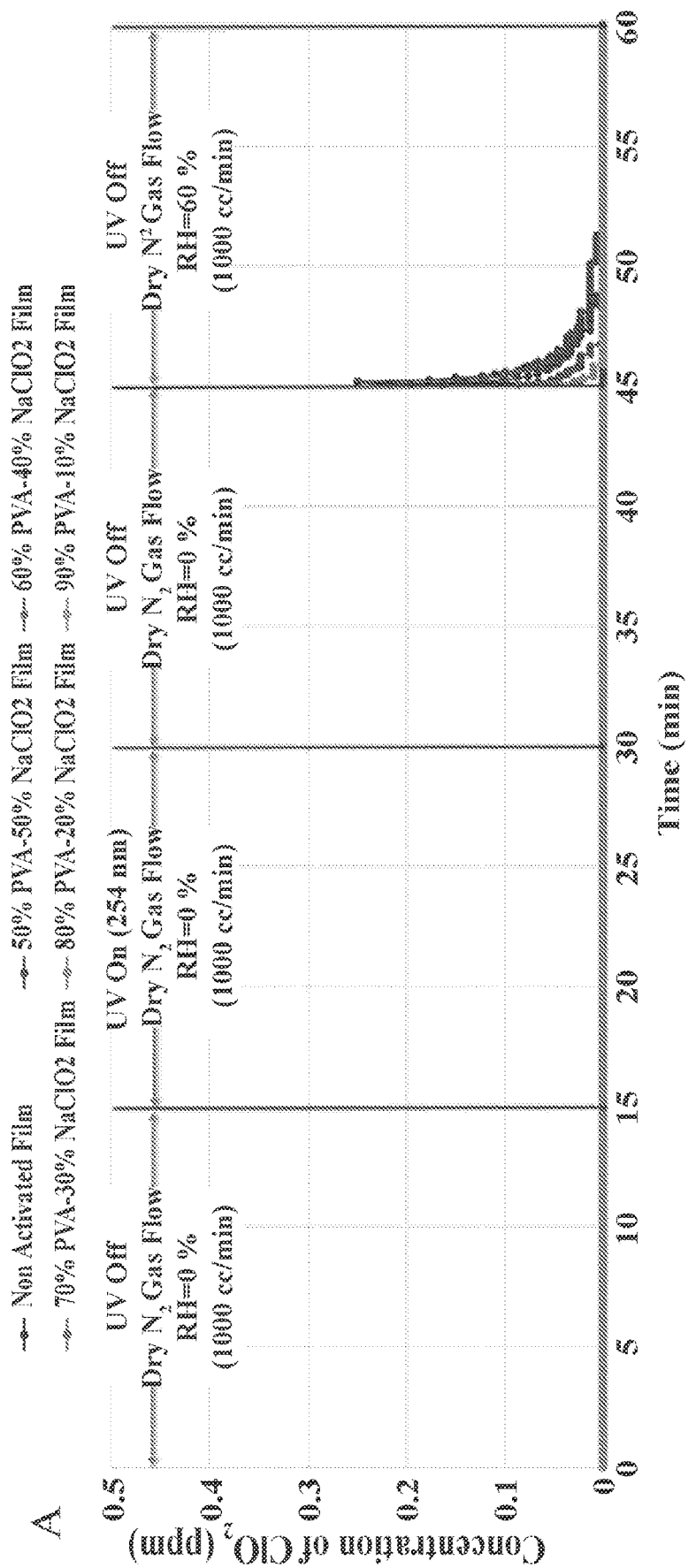
FIG. 11A shows averaged concentration of $ClO_2$ released from UV (wavelength=254 nm) activated thin PVA films that were formulated to contain $NaClO_2$ salt; in these experiments composition of thin films is varied. N=3.

FIG. 11A shows the averaged $ClO_2$ concentration recorded by the detector for thin polymeric films with different $NaClO_2$ mass concentrations activated with UV light (254 nm) and exposed subsequently to moist $N_2$ (RH=60%). Firstly, no $ClO_2$ was detected in control thin films irrespective of the composition of the films (no UV light during activation step in the experiments). However, in thin films that were exposed to UV light during the activation step, $ClO_2$ gas production was recorded only when the thin films were exposed to moisture during the release step.

Figure 11B:
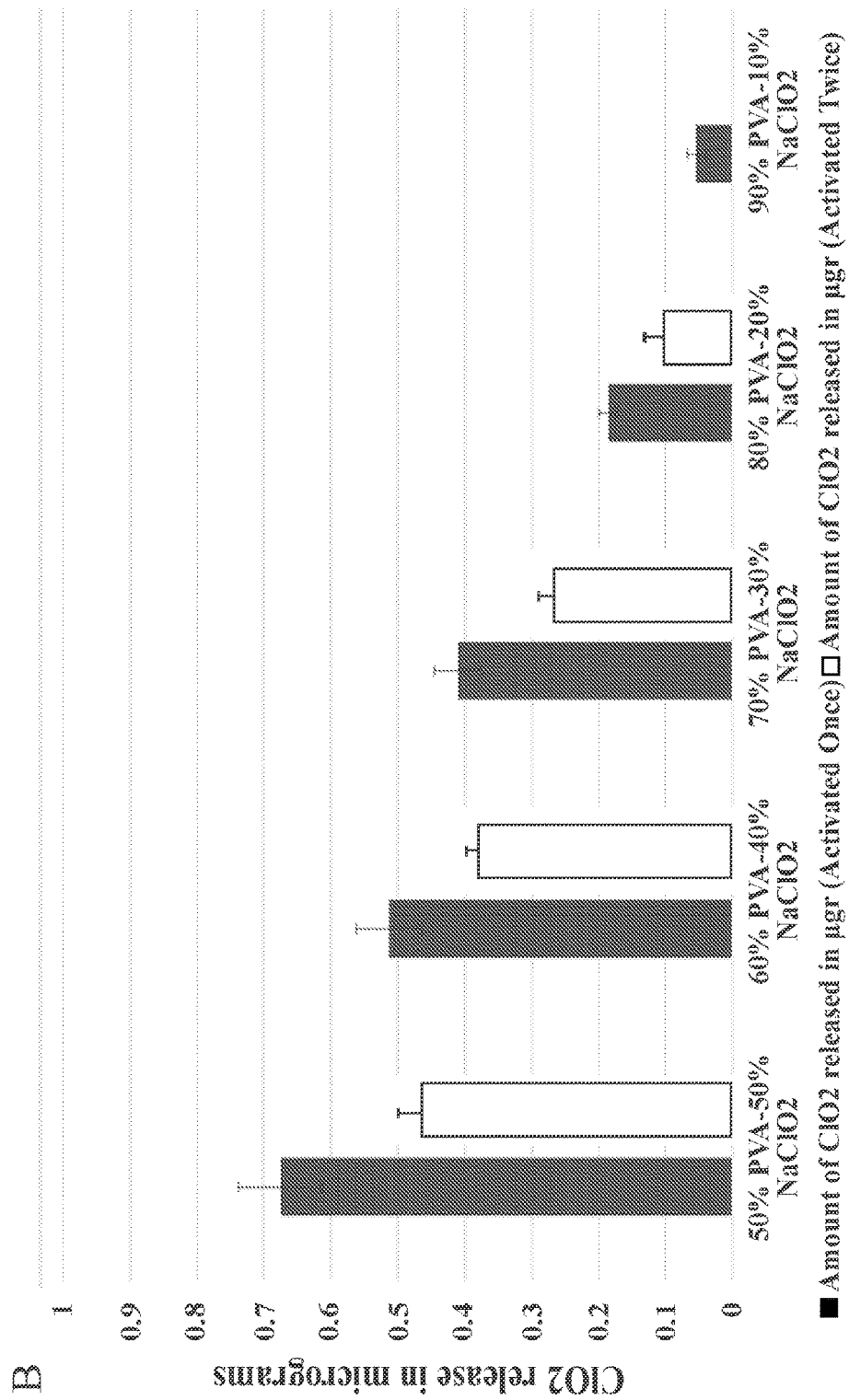
FIG. 11B shows average mass of $ClO_2$ released in experiments where UV (254 nm) activated thin PVA films with different $NaClO_2$ salt mass percent were activated two times at relative humidity of 60%. N=3.

Secondly, the concentration of $ClO_2$ detected varied directly as the mass percent of $NaClO_2$ salt within thin films which was varied between (10 wt. %-50 wt. %) in increments of (10 wt. %). This results shows that film composition (mass percent of $NaClO_2$ salt within the polymeric film) can be used to tune the amount of $ClO_2$ being released from a thin film. In addition, experiments were completed that attempted to reactivate the samples after the first activation cycle. It was found that we can reactivate thin films by subsequent re-illumination of the thin films, although the amount of the $ClO_2$ being produced is less in the reactivation experiments FIG. 11B.

Thirdly, in order to calculate the extent of conversion, the amount of the $NaClO_2$ salt present in the thin polymeric films was quantified by dissolving the polymeric films within 2 mL of deionized water and then recording the UV-Visible spectrum of the solution. Knowing the molar absorptivity of $NaClO_2$ ($NaClO_2$=260 nm=180$M^{-1}$ $cm^{-1}$), the micrograms of $ClO_2$ being present in the thin films was calculated. The conversion of $NaClO_2$ samples was calculated from this data and the amount of $ClO_2$ produced at each composition was recorded by the $ClO_2$ detector. The results are summarized in Table 4. From the table, note that $NaClO_2$ conversion is around 1%.

TABLE 4

Summary of the results obtained by dissolving the thin films with different $NaClO_2$ mass concentrations in 2 mL of deionized water.

| Expected composition of the spin coated film | Absorbance of solution at 260 nm | Microgram of $NaClO_2$ salt present in the solution | Microgram of $ClO_2$ produced during the first activation | Conversion % |
|---|---|---|---|---|
| 50% PVA-50% $NaClO_2$ salt | 0.084 | 80 | 0.67 | 1.13% |
| 60% PVA-40% $NaClO_2$ salt | 0.071 | 71 | 0.51 | 0.98% |
| 70% PVA-30% $NaClO_2$ salt | 0.052 | 52 | 0.41 | 1.09% |

TABLE 4-continued

Summary of the results obtained by dissolving the thin films with different NaClO$_2$ mass concentrations in 2 mL of deionized water.

| Expected composition of the spin coated film | Absorbance of solution at 260 nm | Microgram of NaClO$_2$ salt present in the solution | Microgram of ClO$_2$ produced during the first activation | Conversion % |
| --- | --- | --- | --- | --- |
| 80% PVA-20% NaClO$_2$ salt | 0.033 | 33 | 0.19 | 0.83% |
| 90% PVA-10% NaClO$_2$ salt | 0.019 | 19 | 0.05 | 0.36% |

Effect of Duration of UV-Exposure.

Figure 12:
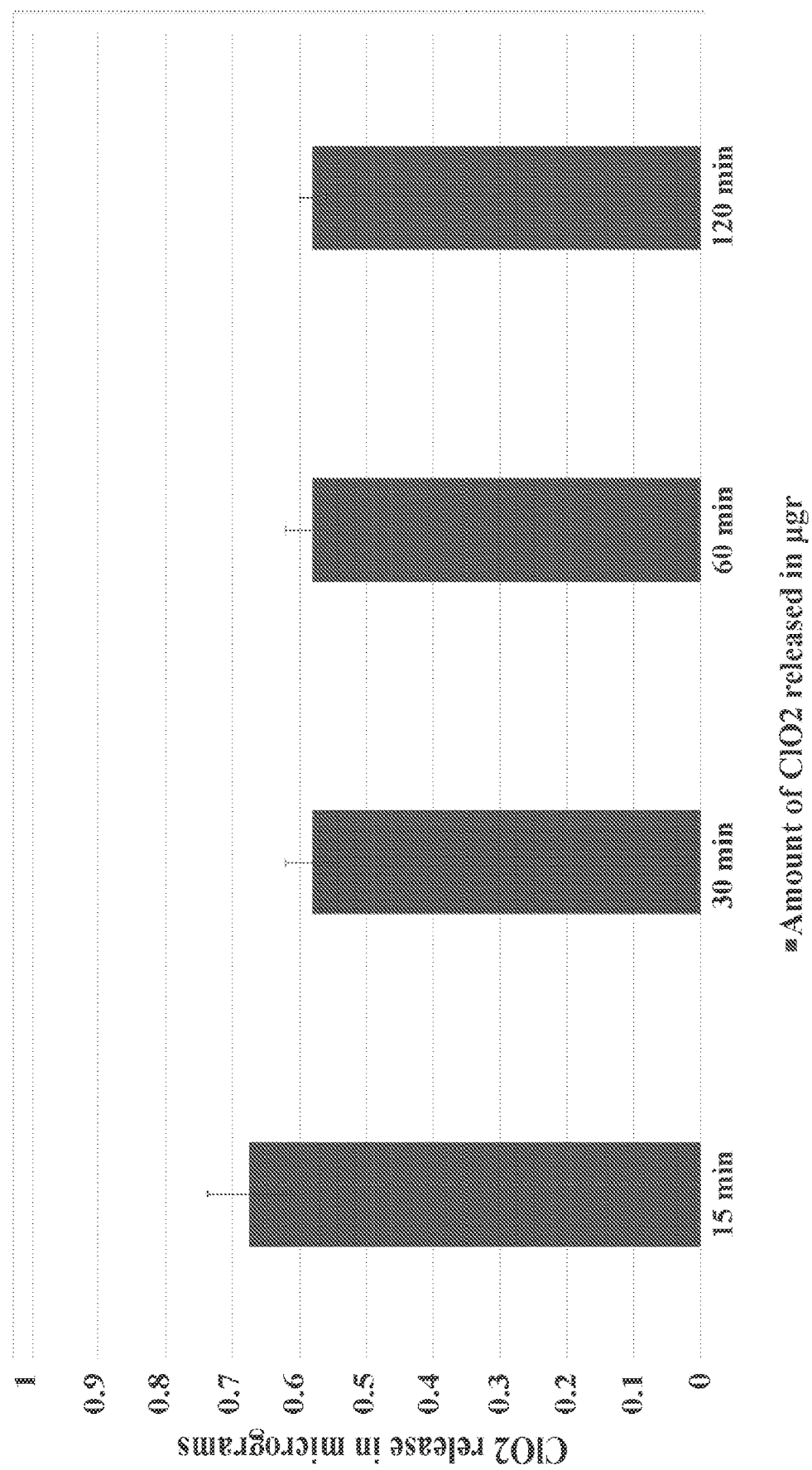
FIG. 12 shows total $ClO_2$ released in 15 min from (50 wt. % $NaClO_2$-50 wt. % PVA) thin films at 60% RH that were activated with UV light (254 nm) for different times (15-120 min). N=3.

Experiments to investigate the effect of duration of UV exposure (Wavelength=254 nm) on the amount of ClO$_2$ being produced from thin polymeric films that were formulated to contain NaClO$_2$ salt (see Table 2 for experimental scheme) were also conducted. For this set of experiments, 50 wt. % NaClO$_2$-50 wt. % PVA thin films were chosen as the model system. FIG. 12 shows the total mass of ClO$_2$ that is produced from NaClO$_2$ samples in 15 min (during release step) that were irradiated with UV light for different durations.

Example 3: Effect of Substrate Type and UV Illumination from Both Sides 50 wt. % NaClO$_2$-50 wt. % PVA thin films were formed on a variety of substrates namely, ordinary glass, silicon wafer, and Au coated silicon wafer (the thickness of gold layer is 1000 Angstroms). The amounts of ClO$_2$ being produced from each of these films is summarized in Table 5. Clearly, ClO$_2$ can be produced from polymeric thin films irrespective of the substrate on which the thin films are formed.

An experiment where a sample was illuminated for 15 minutes from the top and then for another additional 15 minutes from the bottom (the results are summarized in Table 5) was conducted. Illuminating the sample from two directions (above and below) does not increase the extent of conversion significantly. This is not unexpected, since there is a significant amount of diffraction within these films based on the results of UV-Visible spectroscopy of films (data not shown). Therefore, the top layer of the crystal salts within the thin film may have already been activated by illuminating it for 15 minutes from the top direction.

TABLE 5

Summary of the complementary experiments performed to determine the effect of substrate type and UV illumination from both sides on the amount of ClO$_2$ being produced from (50 wt. % NaClO$_2$-50 wt. % PVA) thin films. N = 3.

| Experimental Details | Relative Humidity | ClO$_2$ Produced |
| --- | --- | --- |
| 15 min exposure from the top (fused silica substrate) | 60% | 0.67 ± 0.06 µg |
| 15 min exposure from the top (gold substrate) | 60% | 0.90 ± 0.06 µg |
| 15 min exposure from the top (ordinary Fischer glass substrate) | 60% | 0.75 ± 0.02 µg |
| 15 min exposure from the top (silicon wafer substrate) | 60% | 2.02 ± 0.14 µg |
| 15 min exposure from the top and 15 min from the bottom (fused silica substrate) | 60% | 0.70 ± 0.03 µg |

This example demonstrates that PVA films that are formulated to contain NaClO$_2$ salt can be photochemically activated by UV irradiation and then produce ClO$_2$ when exposed to moisture. Furthermore, PVA polymeric films that are formulated to contain NaClO$_2$ salt can be reactivated by further exposure to the UV light. Finally, ClO$_2$ release from thin films can be tuned by varying salt weight percent within films (i.e. varying film composition).

Packaging Film Pellets Example 1

A 35 weight percent aqueous sodium chlorite solution was prepared by dissolving 1 kg of NaClO$_2$ (technical grade; 80% NaClO$_2$; Sigma-Aldrich, St. Louis, Mo.) in 1.86 kg of distilled water. The solution was made by agitating the water/chlorite salt mixture at ambient temperature.

Pellets of ExxonMobil EXACT® 3040 (ethylene-hexene copolymer; density=0.900 g/cm$^3$; melt index=17 dg/min; obtained from ExxonMobil Chemical Company, Baytown, Tex.) were loaded into the hopper of a gravimetric dosing unit that was positioned to feed the polymer pellets into the main feed port of a 50 mm corotating twin screw extruder. The feeder was configured to dose the EXACT 3040 at a rate of 36 kg/h. The screw elements of the twin screw extruder were arranged in a fashion that allowed for feeding and melting of the polymer pellets, injection and mixing of the water/sodium chlorite solution, removal of the water, pressurization of a die and formation of continuous strands of a homogeneous EXACT 3040/sodium chlorite blend.

The twin screw extruder was heated such that the feed zone temperature was 80° C., the melting zone temperature was 160° C., the liquid injection zone temperature was 200° C. and the devolatilization and discharge zone temperatures were 160° C. The extruder screws were rotated at 100 RPM. The EXACT 3040 was dosed into the primary feed port at 36 kg/h. Once a stable, homogeneous extrudate was achieved, the sodium chlorite/water mixture was injected into the molten EXACT 3040 at an injection port. A gear pump operating at 32 RPM was used to deliver the sodium chlorite/water solution to the injection port. The injection point was placed in a section of the extruder configured to have high free volume and low pressure. The rate of delivery of the solution was calculated by the time change in mass of the water/sodium chlorite mixture. For the 32 RPM pump setting, the water/sodium chlorite delivery rate was 2.1 kg/h and the sodium chlorite concentration, upon accounting for the removal of the water, was 2 weight percentWater was removed via a vent port that was open to the atmosphere. The substantially water-free EXACT 3040/sodium chlorite blend was forced through a four-hole die to form continuous strands. Upon exiting the die, the strands were cooled in a water bath and fed into a pelletizer. The resultant pellets were packed in bags and stored for use.

Packaging Film Pellets Example 2

Example 1 was repeated except that the EXACT 3040 was dosed at 9 kg/h. The resultant pellets had a composition of 92.4 weight percent EXACT 3040 and 7.6 weight percent sodium chlorite.

Packaging Film Pellets Example 3

Example 1 was repeated except that a blend of 98 weight percent of DuPont ELVAX® 3176 (ethylene-vinyl acetate copolymer; vinyl acetate content=18 weight percent; density=0.94 g/cm$^3$; melt index=30 dg/min; supplied by E.I. du Pont de Nemours and Company, Inc., Wilmington, Del.) and 2 weight percent of a masterbatch comprised of 10 weight percent hydrotalcite-based acid scavenger and 90 weight percent LLDPE was used as the polymer portion of the blend. The aqueous sodium chlorite solution was delivered at a rate to yield a sodium chlorite content of 1%. The resultant compounded pellets had a composition of 97.0 weight percent ELVAX 3176, 1.8 weight percent LLDPE, 0.2 weight percent hydrotalcite and 1.0 weight percent sodium chlorite.

Packaging Film Pellets Example 4

Example 3 was repeated except that the aqueous sodium chlorite solution was delivered at a rate to yield a sodium chlorite content of 3%. The resultant compounded pellets had a composition of 95.0 weight percent ELVAX 3176, 1.8 weight percent LLDPE, 0.2 weight percent hydrotalcite and 3.0 weight percent sodium chlorite.

Packaging Film Pellets Examples 5-8

A 36.2 weight percent aqueous sodium chlorite solution was prepared by dissolving 1 kg of NaClO$_2$ (technical grade; 80% NaClO$_2$; Sigma Aldrich) in 1.76 kg of distilled water. The solution was made by agitating the water/chlorite salt mixture at ambient temperature. To this solution, 100 g of AEROSIL® OX 50 hydrophilic fumed silica (surface area=50 m$^2$/g; supplied by Evonik Industries, AG, Essen, Germany) was added. The AEROSIL OX 50 was dispersed by agitation at ambient temperature. The resultant mixture had a composition of 35 weight percent sodium chlorite, 3.5 weight percent AEROSIL OX 50 and 61.5 weight percent distilled water.

Examples 1-4 were repeated except that the aqueous mixture injected

| Example | polymer | polymer concentration % (wt.) | sodium chlorite concentration % (wt.) | AEROSIL OX 50 concentration % (wt.) |
|---|---|---|---|---|
| 5 | EXACT 3040 | 96.1 | 3.5 | 0.4 |
| 6 | EXACT 3040 | 92.1 | 7.1 | 0.8 |
| 7 | ELVAX 3176 | 98.9 | 1.0 | 0.1 |
| 8 | ELVAX 3176 | 96.1 | 3.5 | 0.4 | into the compounding extruder comprised AEROSIL OX 50 as just described. The resultant pellets had the following compositions:

Packaging Film Pellets Example 9

Pellets of ExxonMobil EXACT® 3040 may be loaded into the hopper of a gravimetric dosing unit. Sodium chlorite powder may be loaded into the hopper of a second gravimetric dosing unit. Both dosing units may be positioned to feed their respective contents into the main feed port of a 50 mm co-rotating twin screw extruder. The feeder may be configured to dose the EXACT 3040 at a rate of 45 kg/h. The second feeder may be configured to dose the sodium chlorite at a rate of 5 kg/h.

The twin screw extruder may be heated such that the feed zone temperature is 80° C. and the melting zone and discharge zone temperatures is 160° C. The extruder screws may be rotated at 100 RPM. The EXACT 3040 may be dosed into the primary feed port at 45 kg/h. Concurrently, the sodium chlorite may be dosed into the primary feed port at 5 kg/h. The substantially water-free EXACT 3040/sodium chlorite blend may be forced through a four-hole die to form continuous strands. Upon exiting the die, the strands may be cooled in a water bath and fed into a pelletizer to produce pellets with a composition of 90 weight percent EXACT 3040 and 10 weight percent sodium chlorite.

Packaging Film Example 1

The sodium chlorite-containing pellets produced in Example 1 were processed into a film via a conventional melt extrusion and casting process. The pellets were melted in a 25 mm single screw extruder such that the temperature of the melt stream was 170° C. A 25 cm wide sheet were produced through the use of a slit die and a chilled roll. The resultant film was wound into a roll. By modifying the speed of the winding roll and the extrusion rate, the film thickness could be adjusted to 75µ.

Packaging Film Example 2

In a manner similar to Packaging Film Example 1, the sodium chlorite-containing pellets produced in Example 1 were processed into a film. In this example, layers of EVOH and LDPE were extruded simultaneously in a standard coextrusion process to produce a 25 cm wide, three-layer sheet such that the layers were arranged as follows: sodium chlorite-containing EXACT 3040|EVOH|LDPE. Each of the three layers had a thickness of about 25µ.

Packaging Film Example 3

The sodium chlorite-containing pellets produced in Packaging Film Pellets Example 1 may be used to make an exterior layer of a thermoformable multilayer film. The film may have layers comprised as follow: 85 weight percent nylon 6+15 weight percent nylon 6I/6T (11 weight percent) maleic anhydride-grafted LLDPE (20 weight percent) 85 weight percent nylon 6+15 weight percent nylon 6I/6T (8.5 weight percent) EVOH (9.4 weight percent) 85 weight percent nylon 6+15 weight percent nylon 6I/6T (8.5 weight percent) maleic anhydride-grafted LLDPE (20 weight percent) sodium chlorite-containing ethylene-hexene copolymer from Example 1 (22.6 weight percent). The layers may be coextruded through an annular die, cooled and wound into a thermoformable film.

Packaging Film Example 4

A film similar to the one described in Packaging Film Example 3 may be produced except that the sodium chlorite-containing ethylene-hexene copolymer layer also comprises 0.1% erucamide.

Packaging Film Example 5

The sodium chlorite-containing pellets produced in Packaging Film Pellets Example 1 may be used to make an interior layer of a thermoformable multilayer film. The film may have layers comprised as follow: 85 weight percent nylon 6+15 weight percent nylon 6I/6T (11 weight percent) maleic anhydride-grafted LLDPE (20 weight percent) 85 weight percent nylon 6+15 weight percent nylon 6I/6T (8.5 weight percent) EVOH (9.4 weight percent) 85 weight percent nylon 6+15 weight percent nylon 6I/6T (8.5 weight percent) maleic anhydride-grafted LLDPE (10 weight percent)|sodium chlorite-containing ethylene-hexene copolymer from Example 1 (22.6 weight percent)|ethylene-hexene copolymer (10 weight percent). The layers may be coextruded through an annular die, cooled and wound into a thermoformable film.

Packaging Film Example 6

The film created in Packaging Film Example 2 was exposed to ultraviolet radiation generated by a Spectrolinker XL-1500 (six Phillips G15T8 low-pressure mercury lamps; 0.66 W/cm/bulb; supplied by Spectronics Corporation, Westbury, N.Y.) UV lamp assembly for 60 s. The total exposure energy of 225 µJ/cm$^2$ at 254 nm was measured with an EIT UV Power Puck® II (EIT LLC, Sterling, Va.). Immediately after UV exposure, 14.5 cm$^2$ (3.8 cm×3.8 cm) of the film was placed into a closed 470 ml glass jar. The jar also contained about 50 ml of a saturated aqueous solution of sodium chloride to establish an equilibrium water content corresponding to 75% RH in the jar headspace at ambient temperature. Care was taken to assure that the films did not make direct contact with the aqueous salt solution. After 5 minutes, an equilibrium $ClO_2$ concentration in the jar headspace of 0.14 ppm was measured with a GasAlert Extreme chlorine dioxide detector (BW Technologies by Honeywell, Calgary, AB, Canada).

Packaging Film Example 7

Packaging Film Example 6 was repeated except the sodium chlorite-containing film contained 7.1% sodium chlorite. After 5 minutes, the equilibrium $ClO_2$ concentration in the jar headspace was 0.51 ppm.

Packaging Film Example 8

Packaging Film Example 6 was repeated except the sodium chlorite-containing film of Example 9 was not exposed to UV radiation. After 5 minutes, no measurable $ClO_2$ was present in the jar headspace.

Packaging Film Example 9

Packaging Film Example 6 was repeated except the aqueous salt solution was replaced with 50 g of Indicating Drierite® (anhydrous calcium sulfate, supplied by W A Hammond Drierite CO LTD, Xenia, Ohio). After 5 minutes, no measurable $ClO_2$ was present in the jar headspace.

Packaging Film Example 10

The film created in Packaging Film Example 1 was exposed to ultraviolet radiation generated by a Light Hammer 6 Mark II (200 W/cm; H-type lamp; supplied by Heraeus Noblelight GmbH, Hanau, Germany) UV lamp assembly. The film was transported past a single lamp at 15 m/min at a lamp-to-film distance of 5 cm. Immediately after UV exposure, 58 cm$^2$ (7.6 cm×7.6 cm) of the film was placed into a 470 ml glass jar containing about 50 ml of a saturated aqueous solution of sodium chloride to establish an equilibrium water content corresponding to 75% RH at ambient temperature in the jar headspace. Care was taken to assure that the films did not make direct contact with the aqueous salt solution. After 15 minutes, the chlorine dioxide detector described in Example 14 found >1 ppm chlorine dioxide in the jar headspace, exceeding the detection limit of the detector.

In sum, the results provide methods for incorporating chlorite ions onto films or sheets for packaging and other uses, wherein the disinfecting/deodorizing gas $ClO_2$ can be released on demand to disinfect and/or deodorize that packaged product.

Example 4: Generating $ClO_2$ Gas from the Surface of a Medical Device

As a non-limiting example of a medical device, a medical syringe needle was tested.

Film Preparation on a Medical Syringe Needle

Polyvinyl alcohol (PVA) polymer (Molecular weight=13000-23000 gr/mole, Sigma Aldrich, 98% hydrolyzed) and sodium chlorite ($NaClO_2$) salt (high purity grade, VWR International) were dissolved in deionized water to achieve a ((0.2 gr PVA-0.2 gr $NaClO_2$)/1 mL solution). The metal part of a needle (BD PrecisionGlide™ Needle (22 Gauge 1.5 inch)) was dipped inside the solution and kept within the solution for 10 minutes. The needle was then dried for 30 minutes at T=70° C. inside a temperature controlled oven.

Gas Flow Cell Experiments

Experiments were performed with a stream of $N_2$ gas (Industrial grade, AirGas) flowing through the gas flow cell at a flow rate of 1000 cm$^3$/min. The gas inlet was either (i) directly connected to a $N_2$ gas cylinder (dry gas flow condition) or (ii) to a dew point generator (LI-610, LI-COR Inc.) that was connected to a $N_2$ gas cylinder (moist gas flow condition). The moisture content of the $N_2$ gas flowing into the cell was adjusted for different experiments using the dew point generator. The outlet of the gas flow cell was connected to a $ClO_2$ detector (GasAlert Extreme, Honeywell) with the help of a fixture provided with the detector that ensured the outgoing stream was in proximal contact with the sensor.

For each experiment, the sample was placed on top of the bottom window inside the gas flow cell before sealing it shut. Samples inside the gas flow cell were 'activated' by exposure to ultraviolet (UV) light through the UV-transparent windows on top of the cell (the wavelength of UV is 254 nm (short-wave, UV-C)). Moist $N_2$ gas was blown over activated/non-activated (control) samples, and $ClO_2$ produced during any time was detected by the $ClO_2$ detector which logged the data in its internal memory at a frequency of one data point every 5 seconds. The data was transferred to a computer using a data transfer accessory for further analysis. The total $ClO_2$ produced in any experiment was calculated with the help of area under curve (AUC) of the release profile which was evaluated as:

Total $ClO_2$ (in µg)=$K(\int y\partial t) \approx K(\Sigma y\Delta t)$,

Where, y=detector reading (in ppm), $\Delta t = 1/12$ min, K=unit conversion constant=2.97 µg/(ppm-min) for 1000 (cc/min) flow.

Under the above general scheme, the production of $ClO_2$ from the samples was investigated. Table 6 summarizes the experiment performed.

PVA-$NaClO_2$ film was formed on the metal part of a medical syringe needle through the procedure described above. The general design of the experiments is as follows. Each experiment had 4 steps (1) preparation (2) activation (3) delay and (4) release. Continuous flow of $N_2$ gas (dry/moist, fixed flow rate: 1000 cc/min) was maintained from one end into the gas flow cell and the other end was attached to the $ClO_2$ detector which monitored the $ClO_2$ concentration in the outgoing gas stream. During the preparation step, dry $N_2$ gas was flowed through the gas flow cell containing the sample for 15 min to clear the gas flow cell of any residual gas that may have collected during or between separate experiments. During the activation step, samples were exposed to UV light (wavelength=254 nm) for 15 min. During the delay step, samples were kept in darkness under dry $N_2$ for 15 min. This ensured a time-gap between activation of the samples and exposure to humidity. During the release step, samples were exposed to a flow of moist $N_2$.

Figure 13:
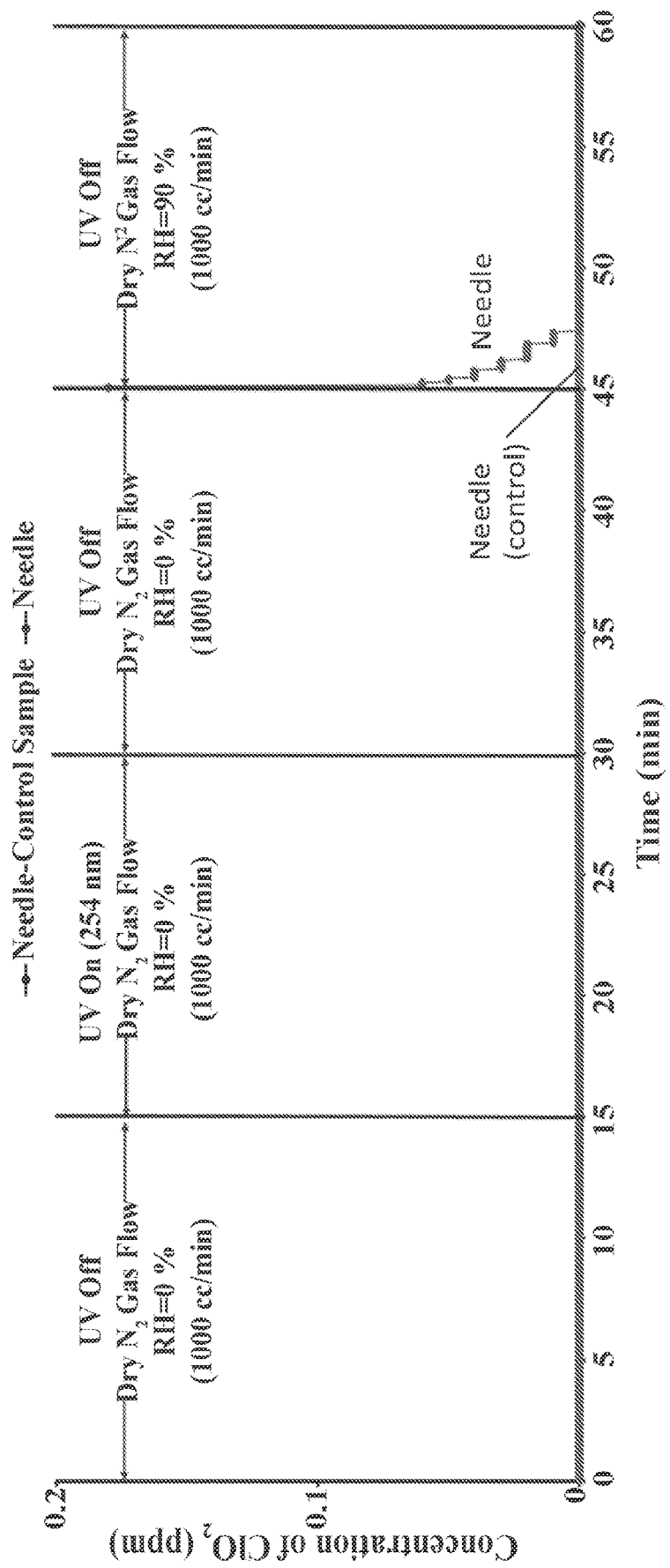
FIG. 13 shows concentration of $ClO_2$ released from UV (wavelength=254 nm) activated PVA films that were formulated to contain $NaClO_2$ salt. The film was formed on a medical syringe needle.

FIG. 13 shows the averaged $ClO_2$ concentration recorded by the detector for the samples activated with UV light (254 nm) and exposed subsequently to moist $N_2$ (the amount of $ClO_2$ produced is summarized in Table 7). No $ClO_2$ was detected in control samples (no UV light during activation step in the experiments). However, in the samples that were exposed to UV light during the activation step, $ClO_2$ production was recorded only when the samples were exposed to moisture during the release step. Overall, the results demonstrate that $ClO_2$ can be produced from the PVA-$NaClO_2$ films deposited on the metallic part of a needle by UV-activation and subsequent exposure to moisture.

TABLE 6

Summary of gas flow cell experiments where release of $ClO_2$ was investigated.
Experiments in which $ClO_2$ was produced from PVA-$NaClO_2$ film deposited on a medical syringe needle

| Step# | Duration (min) | $N_2$ flow - dry/moist | UV light (on/off) | Remarks |
|---|---|---|---|---|
| 1 preparation | 15 | Dry (1000 $cm^3$/min) | Off | Removal of residual moisture/gases from system |
| 2 activation | 15 | Dry (1000 $cm^3$/min) | On (UV-Wavelength = 254 nm) | UV-activation |
| 3 delay | 15 | Dry (1000 $cm^3$/min) | Off | Time gap between activation and $ClO_2$ release |
| 4 release | 15 | Moist (90% RH) (1000 $cm^3$/min) | Off | Release of $ClO_2$ |

TABLE 7

Summary of the results of the experiments performed to show the feasibility of $ClO_2$ production from PVA-$NaClO_2$ films that were formed on a medical syringe needle.

| Sample Description | Microgram of $ClO_2$ produced |
|---|---|
| PVA-$NaClO_2$ film formed on a needle | 0.23 |

Example 5: Generation of ClO2 Gas from a Food Preparation Surface

Method for Generation of ClO2 for Sterilization of a Food Preparation Surface

Polyvinyl alcohol (PVA) polymer (Molecular weight=13000-23000 g/mole, Sigma Aldrich, 98% hydrolyzed) and sodium chlorite ($NaClO_2$) salt (high purity grade, VWR International) were dissolved in deionized water to achieve a ((0.05 gr PVA-0.05 gr $NaClO_2$)/1 mL solution). A plastic food cutting board was used as the substrate for spin coating (a cutting board was purchased from Prepworks by Progressive Cutting Board—17.38"×11.25"). For the purposes of quantification a 2 cm×2.5 cm×1 cm piece was analyzed. The food cutting board was cleaned by water, ethanol, and water and then it was dried by nitrogen gas ($N_2$) before use. 500 microliters of the (PVA-$NaClO_2$) solution was spin coated on the substrate (3000 rounds per minute (rpm) for 1 min). The spin coated film was then dried for 30 minutes at T=70° C. inside a temperature controlled oven.

Gas Flow Cell Experiments

Experiments were performed with a stream of $N_2$ gas (Industrial grade, AirGas) flowing through the gas flow cell at a flow rate of 1000 $cm^3$/min. The gas inlet was either (i) directly connected to a $N_2$ gas cylinder (dry gas flow condition) or (ii) to a dew point generator (LI-610, LI-COR Inc.) that was connected to a $N_2$ gas cylinder (moist gas flow condition). The moisture content of the $N_2$ gas flowing into the cell was adjusted for different experiments using the dew point generator. The outlet of the gas flow cell was connected to a $ClO_2$ detector (GasAlert Extreme, Honeywell) with the help of a fixture provided with the detector that ensured the outgoing stream was in proximal contact with the sensor.

For each experiment, the sample was placed on top of the bottom window inside the gas flow cell before sealing it shut. Samples inside the gas flow cell were 'activated' by exposure to ultraviolet (UV) light through the UV-transparent windows on top of the cell (the wavelength of UV is 254 nm (short-wave, UV-C))). Moist $N_2$ gas was blown over activated/non-activated (control) samples, and $ClO_2$ produced during any time was detected by the $ClO_2$ detector which logged the data in its internal memory at a frequency of one data point every 5 seconds. The data was transferred to a computer using a data transfer accessory for further analysis. The total $ClO_2$ produced in any experiment was calculated with the help of area under curve (AUC) of the release profile which was evaluated as:

$$\text{Total } ClO_2(\text{in } \mu g)=K(\int y\partial t)\approx K(\Sigma y\Delta t),$$

Where, y=detector reading (in ppm), Δt=1/12 min, K=unit conversion constant=2.97 µg/(ppm-min) for 1000 (cc/min) flow.

Under the above general scheme, the production of $ClO_2$ from the samples was investigated. Table 8 summarizes the experiment performed.

PVA-$NaClO_2$ film was formed on the plastic cutting board through the procedure described above. The general design of the experiments is as follows. Each experiment had 4 steps (1) preparation (2) activation (3) delay and (4) release. Continuous flow of $N_2$ gas (dry/moist, fixed flow rate: 1000 cc/min) was maintained from one end into the gas flow cell and the other end was attached to the $ClO_2$ detector which monitored the $ClO_2$ concentration in the outgoing gas stream. During the preparation stage, dry $N_2$ gas was flowed through the gas flow cell containing the sample for 15 min to clear the gas flow cell of any residual gas that may have collected during or between separate experiments. During the activation stage, samples were exposed to UV light (wavelength=254 nm) for 15 min. During the delay stage, samples were kept in darkness under dry $N_2$ for 15 min. This ensured a time-gap between activation of the samples and exposure to humidity. During the release stage, samples were exposed to a flow of moist $N_2$.

Figure 14:
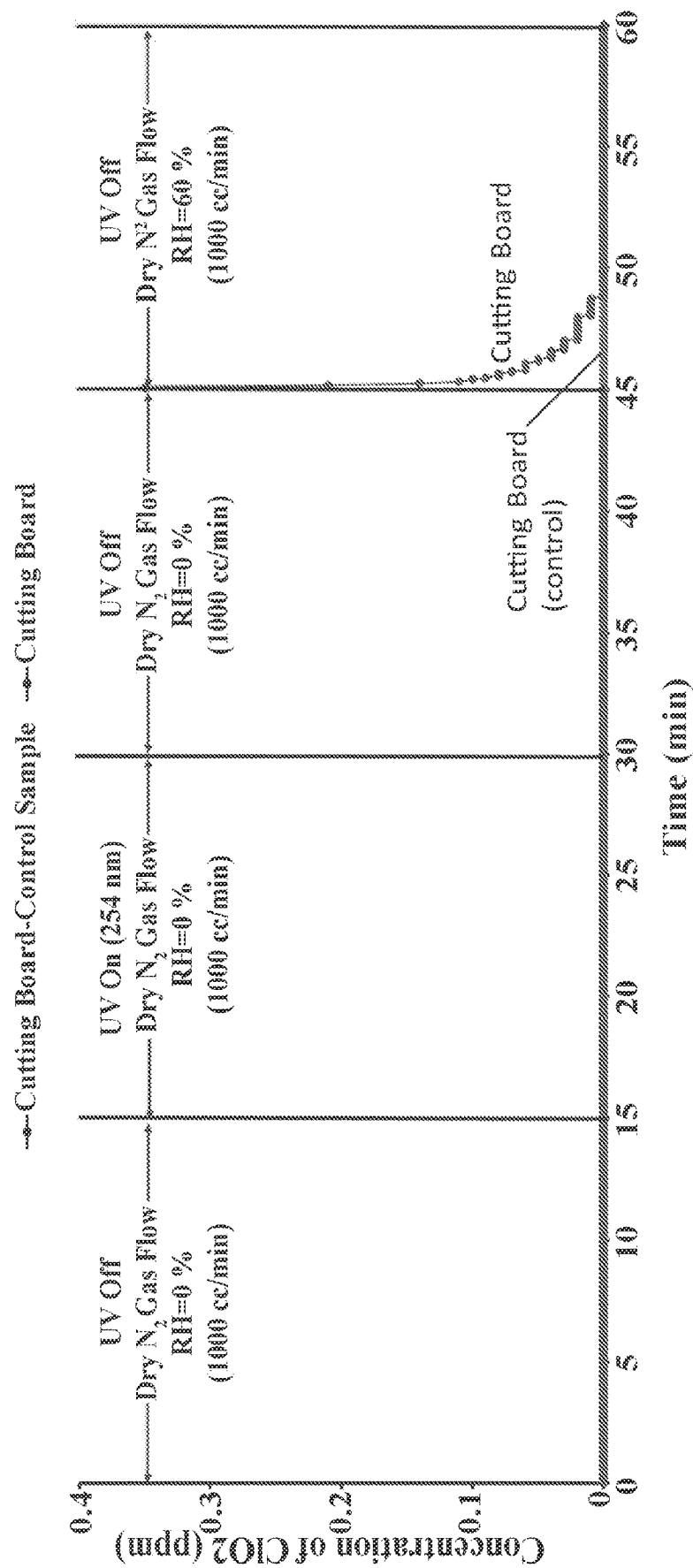
FIG. 14 shows the concentration released from UV (wavelength=254 nm) activated PVA films that were formulated to contain $NaClO_2$ salt. The film was formed on a food cutting board surface.

FIG. 14 shows the averaged $ClO_2$ concentration recorded by the detector for the samples activated with UV light (254 nm) and exposed subsequently to moist $N_2$ (the amount of $ClO_2$ produced is summarized in Table 9). No $ClO_2$ was detected in control samples (no UV light during activation stage in the experiments). However, in the samples that were exposed to UV light during the activation stage, $ClO_2$ production was recorded only when the samples were exposed to moisture during the release stage. Overall, the results demonstrate a method that allows $ClO_2$ to be produced from the food cutting board by UV-activation and subsequent exposure to moisture.

grade; 80% NaClO2; Sigma-Aldrich, St. Louis, Mo.) were mixed and suspended in water, and subsequently left in an open container until most of the water evaporated. The samples were evaporated in complete darkness, without exposure to visible or UV light sources. Similar blends were made with 2:1, 10:1, 20:1, and 65:1 sodium chlorite to titanium dioxide ratios. For testing, individual samples of the blends were placed in small glass vials of volume 20 mL and hermetically sealed. After sealing, the vials were exposed to a compact fluorescent light source for approximately 4.5 hours. A ClO2 detector (PortaSens II, Analytical Technology Inc., Collegeville, Pa.) was used to measure the concentration of the gas generated (see results in Table 10). Subsequently, the samples were exposed to a UV light source (254 nm, Spectrolinker) for 15 seconds. Again, the concentration of ClO2 in the vials was measured and is reported in Table 10.

TABLE 10

Concentration of $ClO_2$ after fluorescent light and UV light exposure. The upper detection limit of the sensor was 240 ppm.

| Sample Reference | Sample mass (g) | $NaClO_2$ to $TiO_2$ to weight ratio | $ClO_2$ concentration after fluorescent light exposure | $ClO_2$ concentration after UV (254 nm) light exposure |
| --- | --- | --- | --- | --- |
| Sample 1 | 2.31 | 1:1 | >240 ppm | >240 ppm |
| Sample 2 | 1.83 | 2:1 | >240 ppm | >240 ppm |
| Sample 3 | 1.55 | 10:1 | 171 ppm | >240 ppm |
| Sample 4 | 1.50 | 20:1 | 196 ppm | >240 ppm |
| Sample 5 | 1.46 | 65:1 | 151 ppm | >240 ppm |
| Sample 6 | 1.39 | $NaClO_2$ only | 63 ppm | >240 ppm |

TABLE 8

Summary of gas flow cell experiments where release of $ClO_2$ was investigated.
Experiments in which $ClO_2$ was produced from PVA-$NaClO_2$ film deposited on a food cutting board

| Step# | Duration (min) | $N_2$ flow - dry/moist | UV light (on/off) | Remarks |
| --- | --- | --- | --- | --- |
| 1 Preparation | 15 | Dry (1000 cm³/min) | Off | Removal of residual moisture/gases from system |
| 2 activation | 15 | Dry (1000 cm³/min) | On (UV-Wavelength = 254 nm) | UV-activation |
| 3 delay | 15 | Dry (1000 cm³/min) | Off | Time gap between activation and $ClO_2$ release |
| 4 release | 15 | Moist (60% RH) (1000 cm³/min) | Off | Release of $ClO_2$ |

TABLE 9

Summary of the results of the experiments performed to show
$ClO_2$ production from PVA-$NaClO_2$ films
that were formed on a food cutting board.

| Sample Description | Microgram of $ClO_2$ produced |
| --- | --- |
| PVA-$NaClO_2$ film formed on food cutting board | 0.55 |

Example 6: Varying Amounts of Energy-Activated Catalyst

Equal parts of titanium dioxide (99.1% TiO2; Sigma-Aldrich, St. Louis, Mo.) and sodium chlorite (technical Self Sterilizing Pouch Example 1

A 35 weight percent aqueous sodium chlorite (technical grade; 80% NaClO2; Sigma-Aldrich, St. Louis, Mo.) solution was prepared and compounded into resin pellets of ExxonMobil EXACT® 3040 (ethylene-hexene copolymer; density=0.900 g/cm3; melt index=17 dg/min; ExxonMobil Chemical Company, Baytown, Tex.) using a 50 mm co-rotating twin screw extruder. The resulting resin had a sodium chlorite content of 7.4% by weight.

The sodium chlorite-containing resin was cast into a film via melt extrusion process using a 3 layer flat die extrusion system. Layers of EVOH and LDPE were extruded simultaneously with the sodium chlorite-containing resin in a co-extrusion process to produce a 25 cm wide, three-layer sheet such that the layers were arranged as follows: 1.5 mil LDPE/1.5 mil EVOH/1 mil LLDPE sodium chlorite. Monolayer films of EVA (DuPont Elvax® 3124 EVA) were also produced. These contained no sodium chlorite.

Self-sterilizing pouches were made from the film by heat-sealing the two edges of film specimens (30 cm length, 15 cm width) folded onto themselves with the sodium chlorite-containing resin layer on the inside. Self-Contained Biological indicators (SCBI) (NAMSA, Northwood, Ohio) containing $1.3 \times 10^6$ bacterial spores (*Bacillus atrophaeus*) were inserted in the pouches and heat-sealed, completing a hermetic package. Some pouches contained 0.2 ml of water to provide additional moisture. Some SCBIs were covered with aluminum foil to protect them from UV light. Some of the pouches were conditioned in a low RH environment to remove the residual moisture from the film. Using ASTM Method D6869-03(2011) Standard Test Method for Coulometric and Volumetric Determination of Moisture in Plastics Using the Karl Fischer Reaction (the Reaction of Iodine with Water), the films were found to have moisture levels of more than 4,000 ppm prior to removing residual moisture and less than 500 ppm after removing residual moisture. The variables with and without foil verify that the UV light itself is not affecting the bacterial spores in the SCBI. The pouches containing SCBIs were exposed to a total of 675 µJ/cm2 of UV radiation (λ: 254 nm) by exposing each pouch for 180 s (90 s—each side) to UV light inside a Spectrolinker XL-1500 (contains six Phillips G15T8 low-pressure mercury lamps; 0.66 W/cm/bulb; Spectronics Corporation, Westbury, N.Y.). The pouches were incubated in a laminar hood overnight. The SCBIs were taken out and 'activated' by pushing in their lids, thereby breaking the growth media-containing ampule inside. They were incubated at 35° C. and evaluated after 48 hours for color change from green to yellow. A color change to yellow indicates a change in pH caused by the growth of surviving bacterial spores. A color of green indicates that no bacterial spores survived. Table 11 summarizes the samples that were tested and the results.

were placed in a high humidity environment (35 C, 80% RH) for approximately 12 hours. Self-Contained Biological indicators (SCBI) were inserted in a pouch of interest along with vacutainers (small devices made of rigid plastics, used to draw a fixed amount of blood from a patient) and heat-sealed, completing a hermetic package. The pouches were exposed to 254 nm UV for 180 seconds. When the pouches were cut open, the ClO2 gas alert detector was used to see if any ClO2 remained in the packages.

SCBIs in pouches containing vacutainers (3 replicates) were sterilized, as indicated by a green color after breaking the ampule and incubating, after exposure to UV and moisture. Also, residual ClO2 was measured to be approximately 0.14 ppm in all pouches (with or without vacutainers) when they were opened after 24 hours.

Produce Packaging Example 1

A two layer cast film was extruded which consisted of an EVOH layer and a polyethylene layer containing 16% of the sodium chlorite additive. Pouches were made using this film (19 cm length, 19 cm width) with the PE layer as the interior food contact layer. The pouches were exposed to 80% RH at 35° C. for approximately 12 hours. After conditioning, the pouches were filled with 20 g baby spinach and sealed. Additional testing was done with empty pouches. The pouches were exposed to 254 nm UV for 3 s or 5 s (one side only). The concentration of chlorine dioxide generated in the pouches was recorded using a PortaSens II gas leak detector. The concentration measurement was taken approximately 1 minute after UV exposure. The results are in Table 12. The lower ClO2 readings for the pouches that contained spinach is theoretically due to degradation of the ClO2 as it is reduced by the pouch contents.

TABLE 11

Different samples tested in experiments to determine sterilizing efficacy of self-sterilizing pouches

| Pouch Spec. | Foil covering on SCBI | Residual Moisture Present? | Additional moisture in pouch (in ml) | Exposure to UV (254 nm) | Resulting SCBI color |
| --- | --- | --- | --- | --- | --- |
| LDPE/EVOH/LLDPE-NaClO2 | No | Yes | 0 | None | Yellow |
| LDPE/EVOH/LLDPE-NaClO2 | No | Yes | 0.2 | None | Yellow |
| EVA3124 monolayer | Yes | Yes | 0 | 180 sec. | Yellow |
| EVA3124 monolayer | No | Yes | 0 | 180 sec. | Yellow |
| LDPE/EVOH/LLDPE-NaClO2 | No | Yes | 0.2 | 180 sec. | Green |
| LDPE/EVOH/LLDPE-NaClO2 | No | Yes | 0 | 180 sec. | Green |
| LDPE/EVOH/LLDPE-NaClO2 | Yes | Yes | 0.2 | 180 sec. | Green |
| LDPE/EVOH/LLDPE-NaClO2 | Yes | Yes | 0 | 180 sec. | Green |
| LDPE/EVOH/LLDPE-NaClO2 | No | No | 0 | 180 sec. | Yellow |

Self Sterilizing Pouch Example 2

A sodium chlorite containing resin and film was produced using the same procedure as described in Self Sterilizing Pouch Example 1. The resulting film had a structure of 1.5 mil LDPE/1.5 mil EVOH/1.5 mil sodium chlorite (16% by weight) containing LLDPE.

Self-sterilizing pouches were made from the film by heat-sealing the two edges of film specimens (30 cm length, 15 cm width) folded onto themselves with the sodium chlorite-containing resin layer on the inside. These pouches

TABLE 12

Concentration of ClO2 in a sealed pouch with and without spinach.

| | ppm ClO$_2$ | |
| --- | --- | --- |
| UV Exposure time (254 nm) | No Spinach | With Spinach |
| 3 seconds | 45.55 | 11.6 |
| 5 seconds | 67.25 | 16.65 |

Produce Packaging Example 2

To verify its efficacy against pathogenic bacteria, pouch samples were sent to Institute of Food Safety and Health (IFSH) for a microbial study where they were filled with 30 grams of lettuce that was inoculated with the *L. monocytogenes* with an initial count of 7.6E+06 CFU/g. The pouches were the same structure and size as Produce Packaging Example 1. The pouches were exposed to 3 s or 5 s of 254 nm UV radiation and analyzed for the microbial kill at 1 and 5 days. It should be noted that the control sample did not contain any ClO2 additive (LDPE sealant laminated to OPP). The pouches containing the ClO2 additive were either pre humidified to 80% RH or left unconditioned. The moisture required for the chlorine dioxide production in the dry samples came from the lettuce. It was observed that chlorine dioxide was able to attain 4-5 log kill in 5 days post inoculation and packaging. The results are summarized in Table 13.

TABLE 13

Log count of *L. monocytogenes* inoculated lettuce

| | | Log Count | | |
|---|---|---|---|---|
| Test Time, post packaging | Conditioning environment | No $ClO_2$ Additive | $ClO_2$ Additive, 3 seconds UV exposure | $ClO_2$ Additive, 5 seconds UV exposure |
| 1 day | Ambient | 6.88 | 4.39 | 5.56 |
| 1 day | 80% RH | 6.88 | 4.63 | 3.54 |
| 5 days | Ambient | 6.74 | 2.4 | 2.38 |
| 5 days | 80% RH | 6.74 | 1 | 1.48 |

All publications and patents specifically mentioned herein are incorporated by reference for all purposes. Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. A method for generating chlorine dioxide from a composition comprising a polymer and a plurality of chlorite ions disposed in the polymer, the method comprising:
    exposing the composition to ultraviolet (UV) light; and
    exposing the composition to moisture, wherein exposing the composition to moisture comprises exposing the composition to humidified gas having a relative humidity within the range of 60% to 100%,
    wherein the composition does not generate a significant amount of chlorine dioxide when exposed to the UV light alone and does not generate a significant amount of chlorine dioxide when exposed to the humidified gas alone.

2. A method according to claim 1, wherein exposing the composition to ultraviolet light comprises exposing the composition to UV light having a wavelength in the range of about 240 nm to 280 nm.

3. A method according to claim 1, wherein the composition comprises less than 10% by weight of an energy-activated catalyst and comprises 2% or less by weight of an acid-releasing agent.

4. A method according to claim 1, wherein the composition comprises less than 5% by weight of an energy-activated catalyst and comprises 1% or less by weight of an acid-releasing agent.

5. A method according to claim 1, wherein the composition comprises less than 2% by weight of an energy-activated catalyst and comprises 1% or less by weight of an acid-releasing agent.

6. A method according to claim 1, wherein the plurality of chlorite ions are present in the composition in the form of a chlorite salt.

7. A method according to claim 6, wherein the chlorite salt is sodium chlorite or potassium chlorite.

8. A method according to claim 6, wherein the composition comprises a weight ratio of an energy-activated catalyst to chlorite salt of 1:5 or less and comprises a weight ratio of an acid-releasing compound to chlorite salt of 1:10 or less.

9. A method according to claim 6, wherein the composition comprises a weight ratio of an energy-activated catalyst to chlorite salt of 1:10 or less and comprises a weight ratio of an acid-releasing compound to chlorite salt of 1:50 or less.

10. A method according to claim 1, wherein the step of exposing the composition to UV light and the step of exposing the composition to moisture are performed simultaneously.

11. A method according to claim 1, wherein the step of exposing the composition to UV light is performed prior to the step of exposing the composition to moisture.

12. A method according to claim 11, wherein the step of exposing the composition to UV light and the step of exposing the composition to moisture are separated by an intervening period of time, wherein the intervening period of time is at least one minute.

13. A method according to claim 1, further comprising drying the composition so that the composition has the moisture content of less than 500 ppm.

14. A method according to claim 13, wherein the drying occurs prior to the step of exposing the composition to UV light.

15. The method of claim 1, wherein the amount of chlorine dioxide generated from the composition upon exposure to moisture alone or UV light alone is at least 20 times less than when the composition is exposed to both UV light and moisture.

16. The method of claim 1, wherein the amount of chlorine dioxide generated from the composition upon exposure to moisture alone or UV light alone is at least 50 times less than when the composition is exposed to both UV light and moisture.

17. The method of claim 1, wherein the amount of chlorine dioxide generated from the composition upon exposure to moisture alone or UV light alone is at least 100 times less than when the composition is exposed to both UV light and moisture.

* * * * *